US010473666B2

(12) United States Patent
Song et al.

(10) Patent No.: US 10,473,666 B2
(45) Date of Patent: Nov. 12, 2019

(54) DYE COMPOUNDS

(71) Applicant: SFC CO., LTD., Chungcheongbuk-do (KR)

(72) Inventors: Ju-man Song, Jeollanam-do (KR); Seon-Gi Min, Gyeonggi-do (KR); Seung-Soo Lee, Daejeon (KR); Do-min Lee, Chungcheongnam-do (KR); Kyung-Hwa Park, Gangwon-do (KR); Moon-Chan Hwang, Gyeongsangnam-do (KR); Bong-Ki Shin, Jeollabuk-do (KR); Jong-Tae Je, Chungcheongbuk-do (KR)

(73) Assignee: SFC CO., LTD., Chungcheongbuk-do (KR)

( * ) Notice: Subject to any disclaimer, the term of this patent is extended or adjusted under 35 U.S.C. 154(b) by 0 days.

(21) Appl. No.: 15/743,769

(22) PCT Filed: Jul. 18, 2016

(86) PCT No.: PCT/KR2016/007801
§ 371 (c)(1),
(2) Date: Jan. 11, 2018

(87) PCT Pub. No.: WO2017/010852
PCT Pub. Date: Jan. 19, 2017

(65) Prior Publication Data
US 2018/0203015 A1 Jul. 19, 2018

(30) Foreign Application Priority Data

Jul. 16, 2015 (KR) ............ 10-2015-0100820
Jul. 16, 2015 (KR) ............ 10-2015-0100821
Jul. 16, 2015 (KR) ............ 10-2015-0100822

(51) Int. Cl.
C09B 23/01 (2006.01)
C09B 57/00 (2006.01)
G01N 33/58 (2006.01)
A61K 49/00 (2006.01)

(52) U.S. Cl.
CPC ....... *G01N 33/582* (2013.01); *A61K 49/0021* (2013.01); *C09B 57/00* (2013.01)

(58) Field of Classification Search
CPC .......... C09B 23/01; C09B 57/00; G01N 33/58
See application file for complete search history.

(56) References Cited

U.S. PATENT DOCUMENTS

| 6,458,966 B1 | 10/2002 | Griffiths et al. | 548/511 |
| 2006/0075582 A1 | 4/2006 | Lagrange | 8/406 |
| 2014/0127737 A1 | 5/2014 | Kim | |
| 2018/0231471 A1* | 8/2018 | Hwang | C08B 37/0039 |

FOREIGN PATENT DOCUMENTS

| EP | 3235909 A1 | 10/2017 | |
| JP | 07-196930 | 8/1995 | ........... C07D 211/76 |
| KR | 10-2009-0066096 | 6/2009 | ......... A61K 49/0485 |
| KR | 10-2013-0017111 | 2/2013 | ........... C07D 403/06 |

OTHER PUBLICATIONS

International Search Report (ISR) from corresponding International Application No. PCT/KR2016/007801 dated Nov. 8, 2016 with its English translation.
Extended European Search Report from corresponding European Patent Application No. 16824767, dated Feb. 19, 2019.
Fujiya, A., et al.; "Sequential Photo-oxidative [3 + 2] Cycloaddition/Oxidative Aromatization Reactions for the Synthesis of Pyrrolo[2,1-a]isoquinolines Using Molecular Oxygen as the Terminal Oxidant", *The Journal of Organic Chemistry*, May 26, 2016, vol. 81, No. 16, pp. 7262-7270.

* cited by examiner

*Primary Examiner* — Laura L Stockton
(74) *Attorney, Agent, or Firm* — Harness, Dickey & Pierce, P.L.C.

(57) ABSTRACT

The present invention relates to dye compounds represented by Formulae I and II, which are described in the specification. The dye compounds of the present invention have markedly improved quantum yields and emit strong fluorescence compared to existing cyanine dyes. Due to these advantages, the dye compounds of the present invention can find applications in various fields, for example, as probes for various biological systems where optical imaging is required. Particularly, the dye compounds of the present invention can be used as mitotrackers capable of labeling and tracking mitochondria. Therefore, the dye compounds of the present invention can be used to quantitatively image mitochondria in live tissues and cells. Furthermore, the dye compounds of the present invention can be applied as pH probes for measuring the pH of live cells.

10 Claims, 16 Drawing Sheets

DYE COMPOUNDS

CROSS-REFERENCE TO RELATED APPLICATIONS

This application is a national phase application of PCT Application No. PCT/KR2016/007801, filed on Jul. 18, 2016, which claims the benefit and priority of Korean Patent Application Nos. 10-2015-0100820, filed on Jul. 16, 2015, 10-2015-0100821, filed on Jul. 16, 2015, and 10-2015-0100822, filed on Jul. 16, 2015. The entire disclosures of the applications identified in this paragraph are incorporated herein by reference.

TECHNICAL FIELD

The present invention relates to dye compounds, and more specifically to novel dye compounds that are excellent in optical properties such as quantum yield, fluorescence intensity and photostability, are highly soluble in water, and are able to bind to biomolecules or maintain their excellent optical properties in biomolecules.

This research was supported by a grant from the Advanced Technology Center (ATC) Program (10076988, Development of fluorescent materials and their application technologies for molecular diagnosis) funded by the Ministry of Trade, Industry & Energy of the Republic of Korea.

BACKGROUND ART

Fluorescence is the most commonly used nondestructive approach for tracking or analyzing biological molecules in the biosciences. Some luminescent proteins and molecules are known but labeling with luminescent dyes is generally required for optical tracking and analysis of proteins, nucleic acids, lipids, and small molecules. Useful information in the field of bioscience can be obtained by analyzing changes in various chemical and optical properties, including simple changes in luminescent properties, imaging based on changes in luminescent properties, energy transfer, changes in luminescent properties caused by changes in ambient environment, and changes in luminescent properties caused by structural changes via chemical reactions.

Analytical systems for such phenomena include fluorescence microscopes, confocal microscopes, flow cytometers, microarrays, and polymerase chain reaction systems for cell observation, electrophoresis systems for nucleic acid and protein isolation, real-time bioimaging systems, immunoassay systems, DNA sequencing systems, PCR assay systems, diagnostic kits and devices for nucleic acids and proteins, and diagnostic and therapeutic systems such as endoscopes for image-guided surgery. New applications and a number of systems for more accurate and easier analysis are currently under continuous development and improvement.

Suitable fluorescent dyes for use in analytical techniques are required to have high brightness in media, i.e. water-soluble media, where biomolecules exist, stability under various pH conditions, photostability, and excitation and emission wavelength characteristics matched to fluorescence systems. As fluorescent dyes meeting these requirements, Xanthane-based fluoresceins and rhodamines and polymethine-based cyanine derivatives are widely known. Particularly, fluorescent dyes having cyanine chromophores that are widely in use belong to the typical category of dyes.

Presently known carbocyanines with indocarbocyanine, indodicarbocyanine, and indotricarbocyanine skeletons have high molar extinction coefficients but low fluorescence quantum yields. Due to this disadvantage, these carbocyanines were reported to exhibit low brightness after coupled to biomolecules.

This problem needs to be solved to develop novel dyes that can emit stronger fluorescence to obtain effective optical images.

Since 1856, polymethine cyanine dyes have held an unchallenged position in various application fields of dyes. Numerous applications in various areas are being published every year on this subject.

The generic cyanine dyes consist of two nitrogen centers, one of which is positively charged and is linked by a conjugated chain of an odd number of carbon atoms to the other nitrogen. This has been studied as "Push-pull" alkenes and forms the basis of the polymethine dyes, which contain the streptopolymethine unit as the chromophore. Depending upon the charge of the streptomethine unit, these dyes are classified as follows: Cationic streptopolymethine-cyanine and hemicyanine dyes (1), anionic streptopolymethine-oxonol dyes (2), neutral streptopolymethine-merocyanine dyes (3), and zwitterionic squaraine-based cyanine dyes (4):

1

$X = Br, I, ClO$

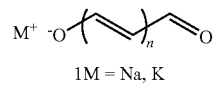

2

$1M = Na, K$

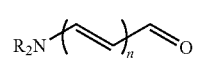

3

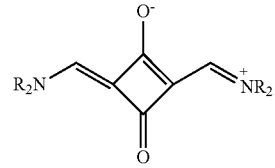

4

Generally, the dyes have all-trans geometry in their stable form. Occasionally, these dyes undergo photoisomerization. The formation of these species can be studied by using various techniques such as flash photolysis, transient absorption and picosecond time-resolved spectroscopy. These dyes have been employed extensively as spectral sensitizers in silver halide photography and band-gap semiconductor materials, as recording media in optical discs, in industrial paints for trapping of solar energy, as laser materials, in light-harvesting systems of photosynthesis, as photo-refractive materials, as antitumor agents, and as probes for biological systems.

Generally, the above dyes are deep in color, which is explained by their high molar extinction coefficients, but have the fatal disadvantage of low quantum yield. The reason is that the cyanine dyes in rotational, translational, and vibrational modes lose their excited-state energy by a non-radiative process rather than by a fluorescence process (D. F. O'Brien, T. M. Kelly, and L. F. Costa (1974). Excited state Properties of some Carbocyanine dyes and the energy transfer mechanism of spectral sensitisation. Photogr. Sci. Eng. 18(1), 76-84.). In an attempt to reduce such fluorescence loss, the inventors of the present invention designed cyanine dyes with a rigid polymethine chain to achieve greatly increased fluorescence quantum yield.

Commercially available mitotracker dyes are capable of selective binding to intracellular mitochondria because they are positively charged, are suitable for use as mitotrackers due to their high fluorescence brightness and outstanding photostability, and are sufficiently stained by a simple incubation for labeling of mitochondria.

However, an operation for fixing cells in a reagent, such as formaldehyde, is required in a subsequent experiment. In this operation, however, some commercially available mitotrackers fail to maintain their fluorescence.

The following mitotrackers are commercially available from Thermo Fisher Scientific:

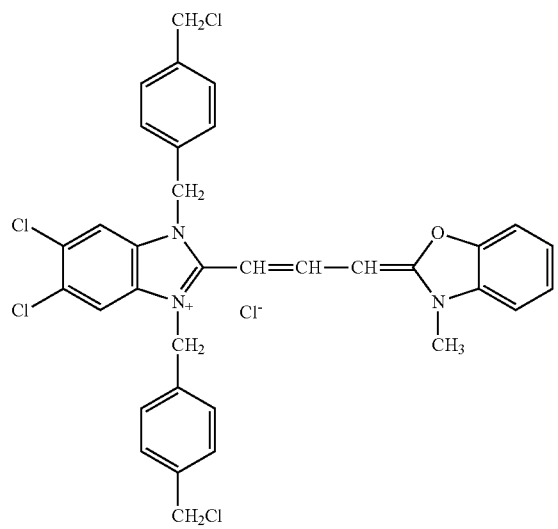

MitoTracker® Green FM
Thermo M7514

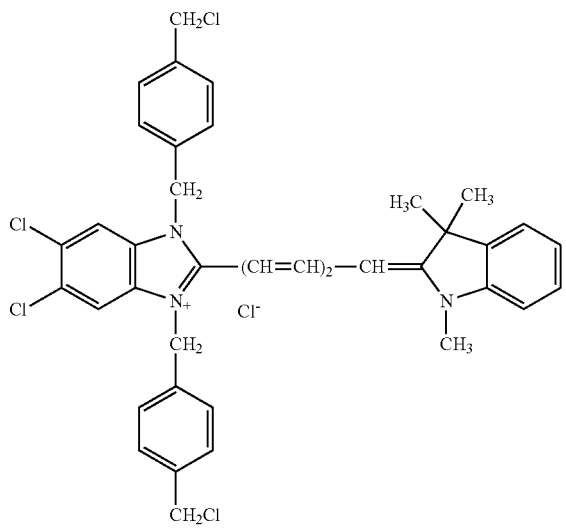

MitoTracker® Red FM
Thermo M22425

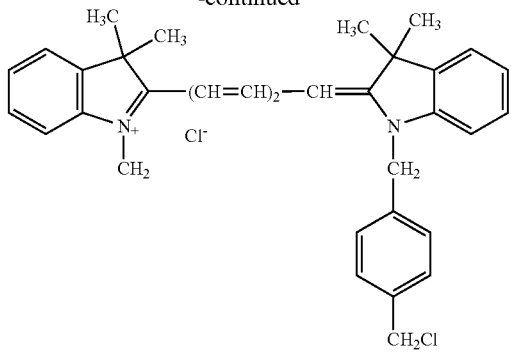

MitoTracker® Deep Red FM
Thermo M22426

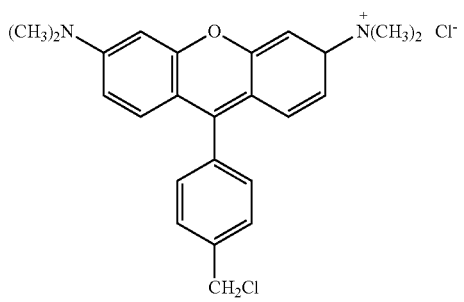

MitoTracker® Orange CMTMRos
Thermo M7510

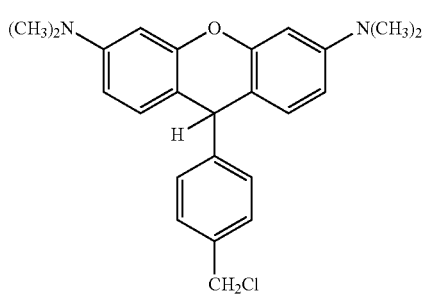

MitoTracker® Orange CM-H₂TMRos
Thermo M7511

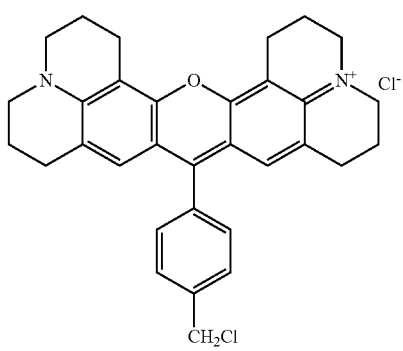

MitoTracker® Red CMXRos
Thermo M7512

-continued

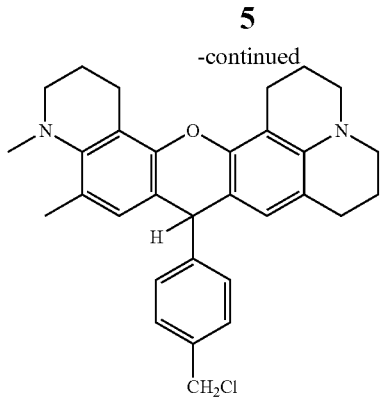

MitoTracker® Red CM-H₂Xros
Thermo M7513

The inventors of the present invention tried to develop dyes whose fluorescence is maintained stable even after fixation and to design dyes emitting fluorescence at various wavelengths so that that a user can choose mitotrackers emitting desired wavelengths.

Materials emitting fluorescence at various wavelengths with narrow bandwidths are considered as important factors because their fluorescence is difficult to analyze when overlapping with the fluorescence wavelengths of other probes. Thus, the inventors of the present invention intended to develop mitotrackers having various wavelengths.

The measurement of intracellular pH or cytosolic pH will greatly facilitate the identification of cellular functions (Methods Mol Biol 637, 311 (2010); Nanotechnology 24, 365 (2013)). On the other hand, many cellular functions, such as ionic homeostasis, reactive oxygen species balance, apoptosis, cell cycle, and cellular mobility, can measured through changes in intracellular pH (Circulation 124, 1806 (2011); Yonsei Med J 6, 473 (1995); J Bacteriol 185, 1190 (2003)).

pH detecting probes are used for the measurement of intracellular pH. Thus, the inventors of the present invention intended to develop dyes whose fluorescence intensity varies in response to pH change and to use the dyes as pH probes capable of measuring the pH of live cells based on this pH-dependent behavior.

DETAILED DESCRIPTION

Problems to be Solved by the Invention

The present invention is directed to providing novel dyes that can emit stronger fluorescence to obtain effective optical images.

The present invention is also directed to providing dyes whose fluorescence is maintained stable even after fixation and dyes designed to emit fluorescence at various wavelengths so that a user can choose mitotrackers emitting desired wavelengths.

The present invention is also directed to providing dyes whose fluorescence intensity varies in response to pH change and can be used as pH probes for measuring the pH of live cells.

Means for Solving the Problems

One aspect of the present invention provides a dye compound selected from compounds represented by Formulae I and II:

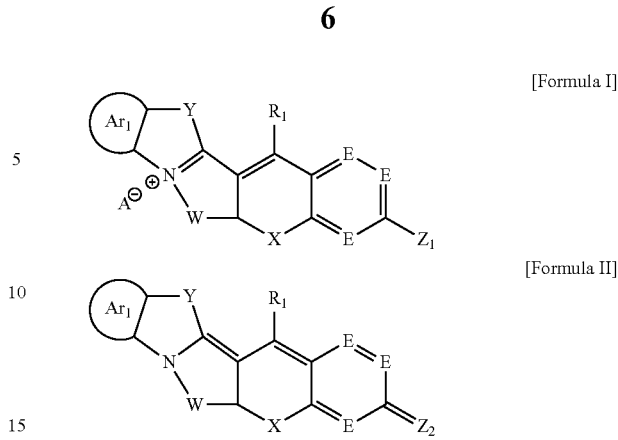

The definitions of the substituents in Formulae I and II are described in detail hereinafter.

A further aspect of the present invention provides a method for labeling a target substance with the dye compound, including binding the dye compound to the target substance.

Effects of the Invention

The dye compounds of the present invention have markedly improved quantum yields and emit strong fluorescence compared to existing cyanine dyes. Due to these advantages, the dye compounds of the present invention can find applications in various fields, for example, as probes for various biological systems where optical imaging is required.

Particularly, the dye compounds of the present invention can be used as mitotrackers capable of labeling and tracking mitochondria. Therefore, the dye compounds of the present invention can be used to quantitatively image mitochondria in live tissues and cells. Furthermore, the dye compounds of the present invention can be applied as pH probes for measuring the pH of live cells.

BEST MODE FOR CARRYING OUT THE INVENTION

Figure 1A:
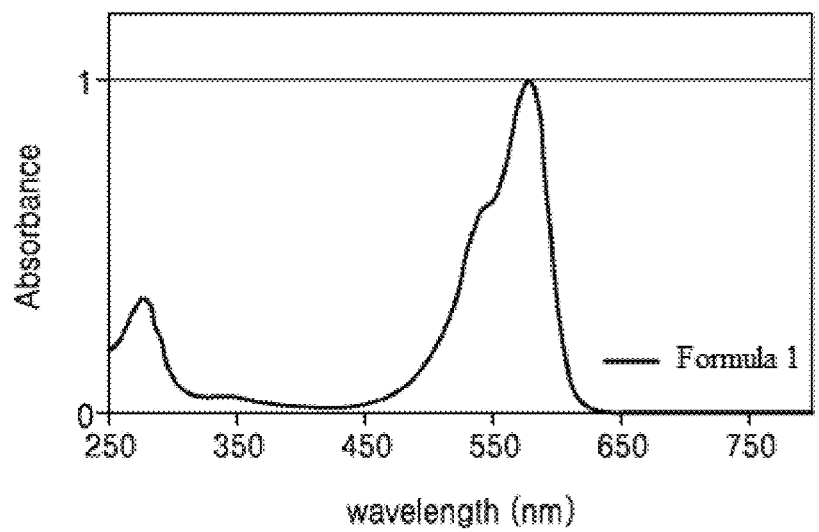
FIG. 1a is an absorption spectrum of goat anti-mouse IgG labeled with the compound of Formula 1.

The present invention will now be described in more detail.

The present invention is directed to dye compounds having novel structures that have markedly improved fluorescence quantum yields and are designed to emit strong fluorescence to obtain effective optical images, thus being useful as probes for various biological systems.

One aspect of the present invention is directed to novel dye compounds represented by Formulae I and II:

[Formula I]

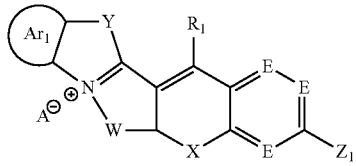

wherein $Ar_1$ is $C_6$-$C_{20}$ aryl or $C_2$-$C_{20}$ heteroaryl which is optionally substituted with one or more substituents selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxyl, aldehyde, amino, amide, hydrazine, thiol, acetal, ketal, phosphoryl, phosphate, phosphonate, sulfohydroxyl, sulfonyl, sulfonate, sulfate, carboxylate, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, the alkyl, alkenyl, alkynyl, aryl, heteroaryl, arylalkyl, aryloxy, aryloxyalkyl, alkoxy, and alkoxyalkyl being optionally further substituted with one or more substituents selected from halogen, cyano, nitro, amine, hydroxyl, aldehyde, amino, amide, hydrazine, thiol, acetal, ketal, phosphoryl, phosphate, phosphonate, sulfohydroxyl, sulfonyl, sulfonate, sulfate, carboxylate, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, each E is $CR_1$ or N, $Z_1$ is $NR_2R_3$, $OR_4$ or $SR_5$, X is O, S, $NR_8R_9$, $SiR_{10}R_{11}$, $CR_{12}R_{13}$ or Se, Y is $CR_{14}R_{15}$, $NR_{16}$, O, S, Se, $SiR_{17}R_{18}$ or $CR_{19}R_{20}$=$CR_{21}R_{22}$)

W is $CR_{23}R_{24}$, $CR_{25}R_{26}$=$CR5_{27}R_{28}$, O, —[$CR_{29}R_{30}$—$CR_{31}R_{32}$]— or —[$CR_{33}R_{34}$—O]—, $R_{23}$ to $R_{34}$ are identical to or different from each other and are each independently hydrogen, deuterium, alkyl or acryloxy, and two adjacent substituents are optionally linked to each other to form an alicyclic hydrocarbon, two of $R_1$ to $R_3$ optionally form an alicyclic hydrocarbon ring or a monocyclic or polycyclic aromatic hydrocarbon ring with two of the adjacent substituents, and carbon atom of the alicyclic or aromatic hydrocarbon ring is optionally replaced by a substituent selected from N, S, O, Se, Te, Po, $NR_{35}$, $SiR_{36}R_{37}$, $GeR_{38}R_{39}$, $PR_{40}$, and $BR_{41}$, $R_1$ to $R_{22}$ and $R_{35}$ to $R_{41}$ are identical to or different from each other and are each independently selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxyl, aldehyde, amino, amide, hydrazine, thiol, acetal, ketal, phosphoryl, phosphate, phosphonate, sulfohydroxyl, sulfonyl, sulfonate, sulfate, carboxylate, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, the alkyl, alkenyl, alkynyl, aryl, heteroaryl, arylalkyl, aryloxy, aryloxyalkyl, alkoxy, and alkoxyalkyl being optionally further substituted with one or more substituents selected from halogen, cyano, nitro, amine, hydroxyl, aldehyde, amino, amide, hydrazine, thiol, acetal, ketal, phosphoryl, phosphate, phosphonate, sulfohydroxyl, sulfonyl, sulfonate, sulfate, carboxylate, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, and A⁻ is an organic or inorganic ion; and

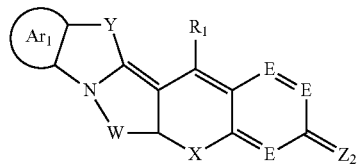

[Formula II]

wherein Ar₁, E, X, Y, W, and R₁ are as defined in Formula I, Z₂ is NR₆, O, S or O⁺R₇, and R₆ and R₇ are as defined in Formula I.

A⁻ in Formulae I and II is not particularly limited and is suitably chosen depending on the desired application taking into consideration the solubility and stability of the dyes in organic solvents. A⁻ in Formulae I and II may be an organic or inorganic cation represented by A⁺.

Generally, A⁻ in Formulae I and II may be an inorganic acid anion selected from phosphoric acid hexafluoride ion, halogen ion, phosphoric acid ion, perchloric acid ion, periodic acid ion, antimony hexafluoride ion, tartaric acid hexafluoride ion, fluoroboric acid ion, and tetrafluoroborate ion, an organic acid ion selected from thiocyanic acid ion, benzenesulfonic acid ion, naphthalenesulfonic acid ion, p-toluenesulfonic acid ion, alkylsulfonic acid ion, benzenecarboxylic acid ion, alkylcarboxylic acid ion, trihaloalkylcarboxylic acid ion, alkylsulfonic acid ion, trihaloalkylsulfonic acid ion, and nicotinic acid, or an ion of a metal compound selected from bisphenyldithiol, thiobisphenol chelate, and bisdiol-α-diketone. Alternatively, A⁻ in Formulae I and II may be also be a metal ion selected from sodium and potassium ions or a quaternary ammonium ion.

According to one embodiment of the present invention, A⁻ in Formulae I and II may be selected from halogen ion, $-SO_4^{2-}$, $-S_2O_3^{2-}$, $-SO^{3-}$, $-ClO^{4-}$, $-BF^{4-}$, $-PF^{6-}$, $-SbF^{6-}$, $-BiCl^{5-}$, $-AsF^{6-}$, $-SbCl^{6-}$, $-SnCl^{6-}$, $-HSO^{4-}$, $-SO_3CH^{3-}$, Na⁺, K⁺, quaternary ammonium ion, acetate ion, propionate ion, cyanate ion, and combinations thereof. A⁻ in Formulae I and II may be present or absent depending on the ionic valence of the anion substituted with the cation.

Each of the dye compounds represented by Formulae I and II may include one or more reactive substituents that can bind to a target substance. Each of the dye compounds represented by Formulae I and II may include one or more polar charged substituents. The presence of the polar charged substituents increases the solubility of the dye compounds in water, prevents the interaction between the fluorescent dye molecules, and prevents unwanted labeling of various markers with the dyes.

According to one preferred embodiment, at least one of the substituents may be conjugated to a target substance having one or more substituents, such as amine, thiol, alcohol, aldehyde, and ketone groups.

The target substance may be, for example, selected from biomolecules, nanoparticles, and organic compounds but is not limited thereto. Specifically, the target substance may be selected from the group consisting of: antibodies; antigens; lipids; proteins; peptides; carbohydrates; dextrans; fatty acids; phospholipids; lipopolysaccharides; nucleotides or oligonucleotides including or derivatized to include one or more amino, sulfhydryl, carbonyl, hydroxyl, carboxyl, thiol, phosphoric acid, and thiophosphoric acid groups; oxypolynucleotides or deoxypolynucleotides including or derivatized to include one or more amino, sulfhydryl, carbonyl, hydroxyl, carboxyl, thiol, phosphate, and thiophosphate groups; microbes; drugs; hormones; cells; cell membranes; toxins; and combinations thereof.

Specific examples of the reactive substituents include activated esters, carboxyl, amides, acrylamides, azides, acyl azides, acyl halides, alkynes, amines, aldehydes, ketones, alkyl halides, alkyl sulfonates, aryl halides, aziridines, boronates, diazoalkanes, epoxides, haloplatinates, halotriazines, imidoesters, isocyanates, silyl halides, sulfonate esters, sulfonyl halides, succinimidyl esters, sulpho-succinimidyl esters, anhydrides, acid halides, isothiocyanates, vinylsulphones, dichlorotriazines, haloacetamides, maleimides, carbodiimides, phosphoramidites, hydrazines, and hydrazides. Preferably, the reactive substituents are succinimidyl esters of carboxylic acids, isothiocyanates, maleimides, and haloacetamides.

The activated esters are represented by —COR' where R' represents a good leaving group for substitution reactions known in the art and may be, for example, succinimidyloxy ($-OC_4H_4O_2$), sulfosuccinimidyloxy ($-OC_4H_3O_2-SO_3H$), -1-oxybenzotriazolyl ($-OC_6H_4N_8$), aryloxy optionally containing one or more electron withdrawing groups such as nitro, halogen, cyano, and haloalkyl, or a carboxylic acid activated by a carbodiimide to form an anhydride ($-OCOR_a$ or $-OCNR_aNHR_b$, where $R_a$ or $R_b$ is $C_1$-$C_6$ alkyl, $C_1$-$C_6$ alkoxy, cyclohexyl, 3-dimethylaminopropyl or N-morpholinoethyl.

The reactive substituents $R_x$ may be covalently bonded to various linkers L to form $R_x$-L-structures.

The linkers may be single bonds or are preferably straight or branched chains containing 1 to 20 linked atoms selected from the group consisting of carbon (C), nitrogen (N), oxygen (O), and sulfur (S) atoms. The linkers may also be aliphatic hydrocarbon rings, aromatic hydrocarbon rings, heteroaliphatic rings or heteroaromatic rings. The linkers may be positively (+) or negatively (−) charged.

According to the present invention, the dye compounds represented by Formulae I and II may be selected from the compounds of Formulae 1 to 113:

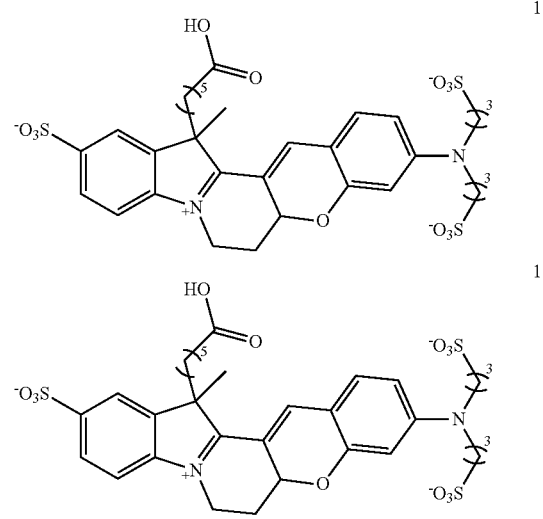

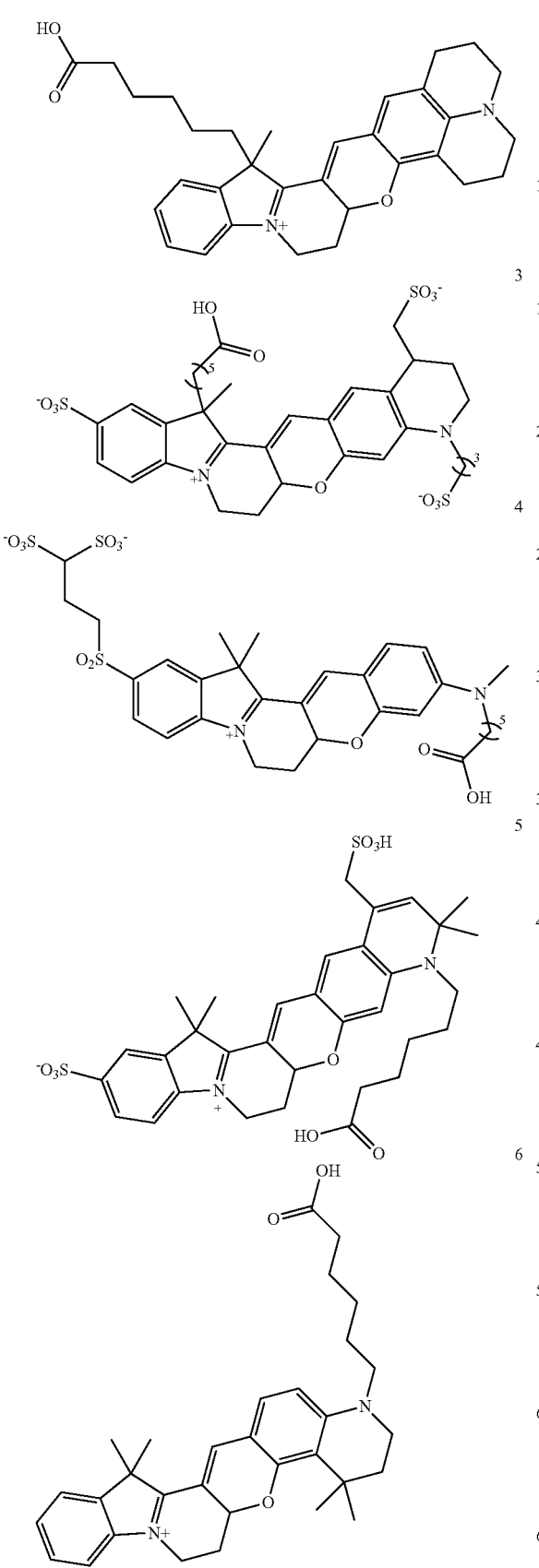
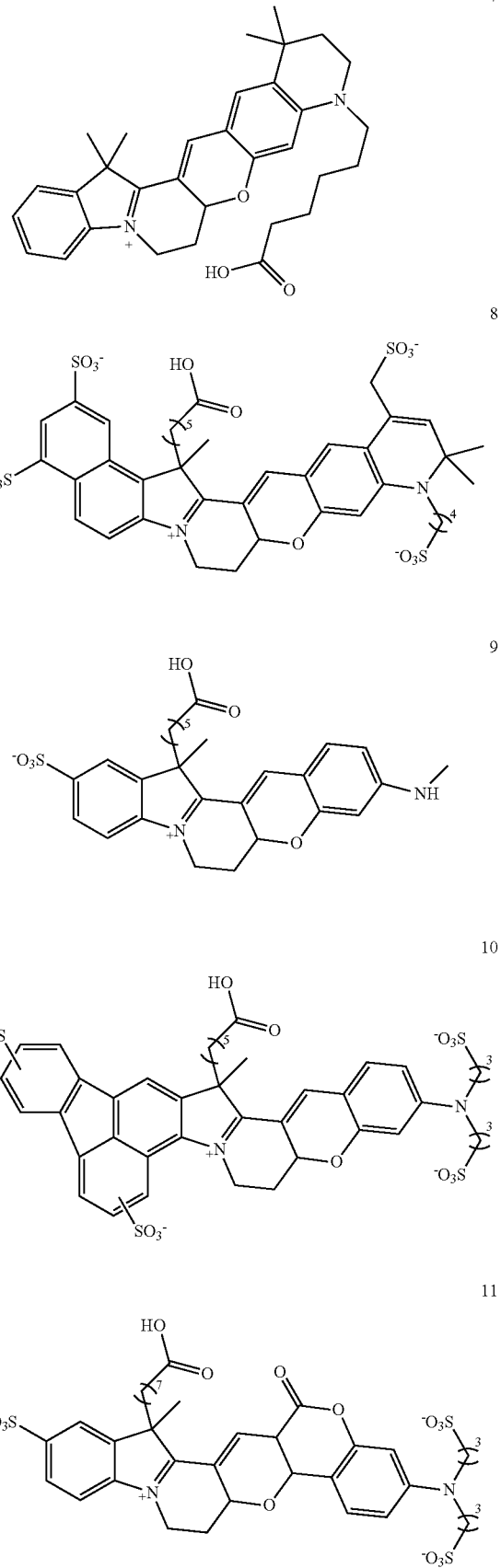

12
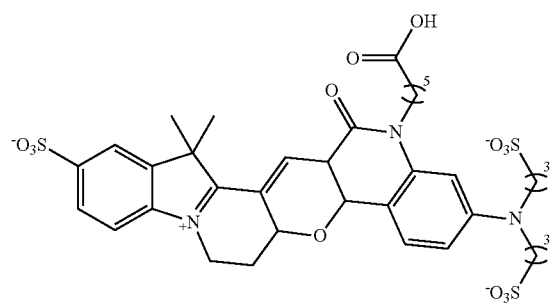
13
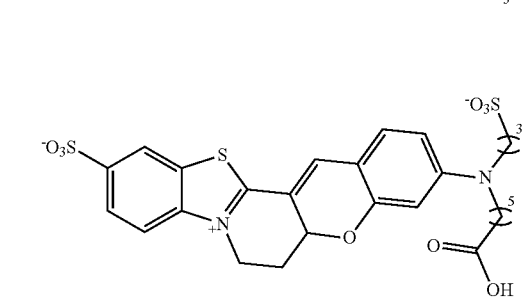
14
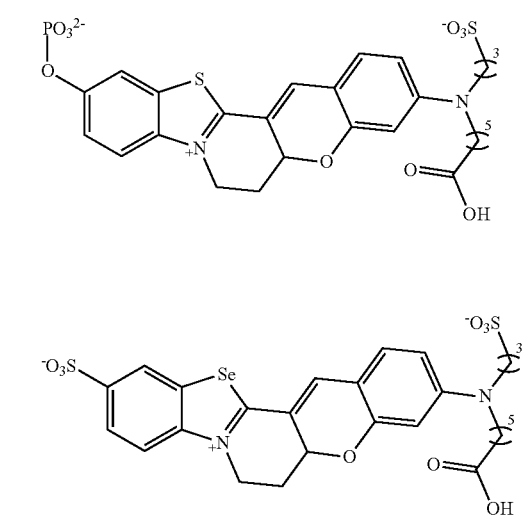
15
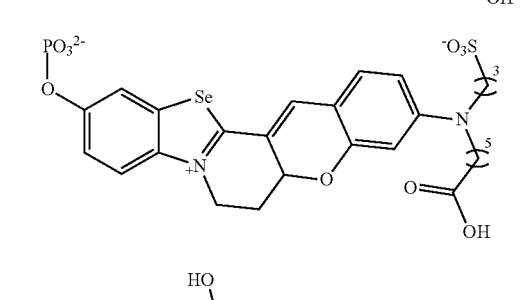
16
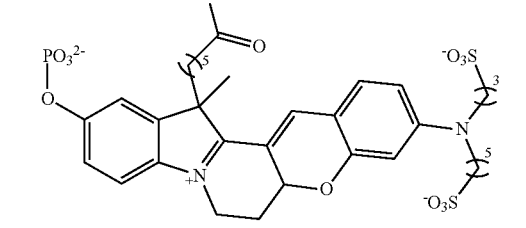
17
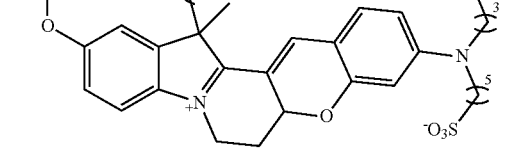
18
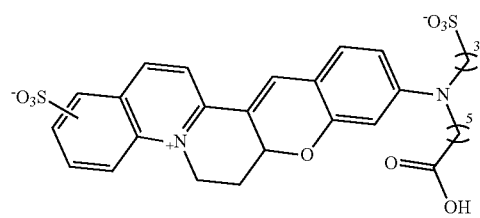
19
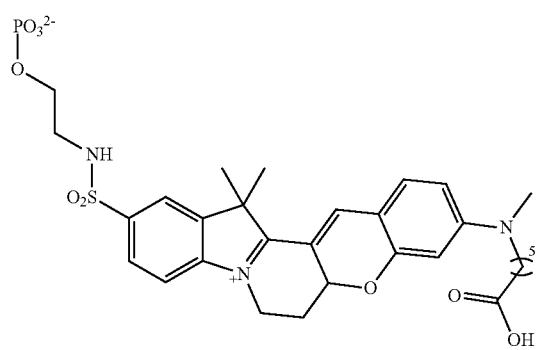
20
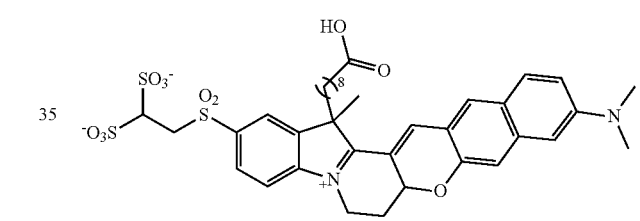
21
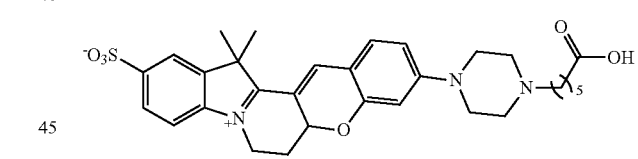
22
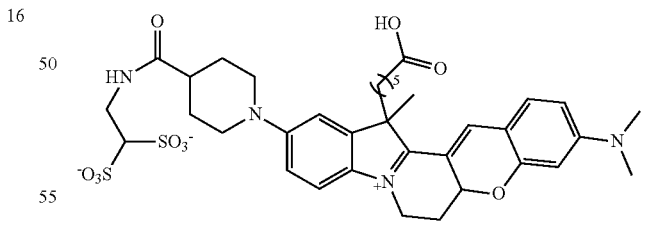
23
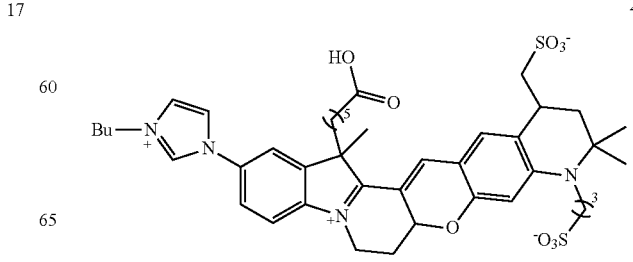

24
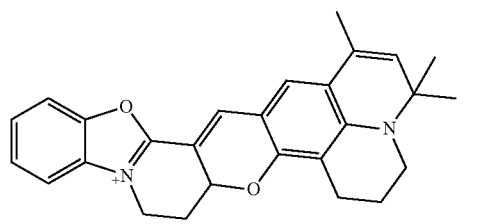
25
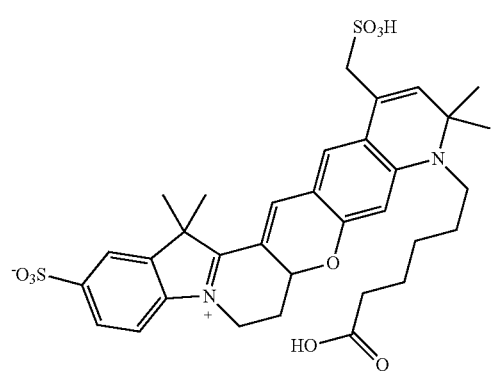
26
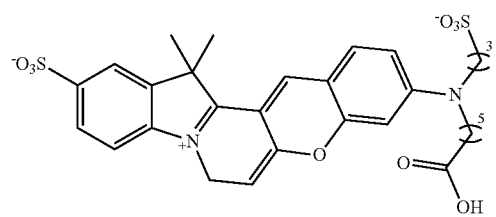
27
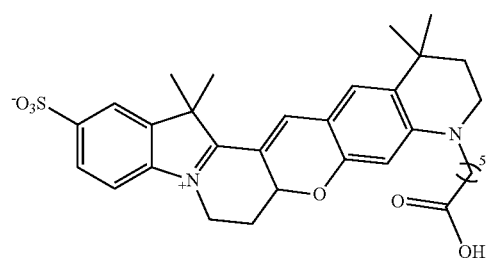
28
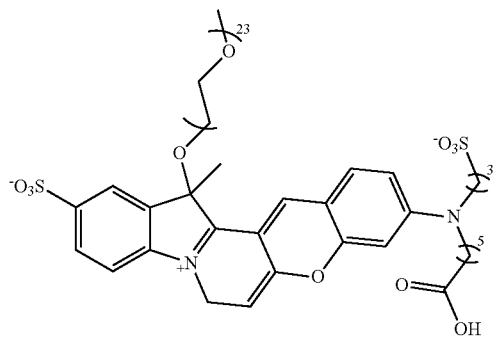
29
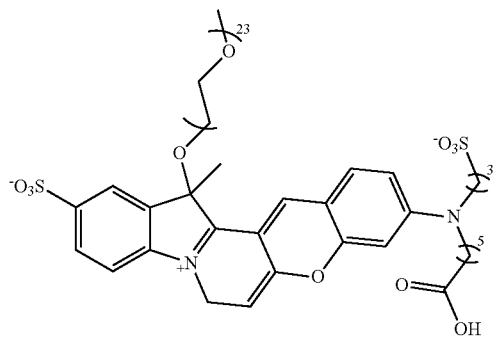
30
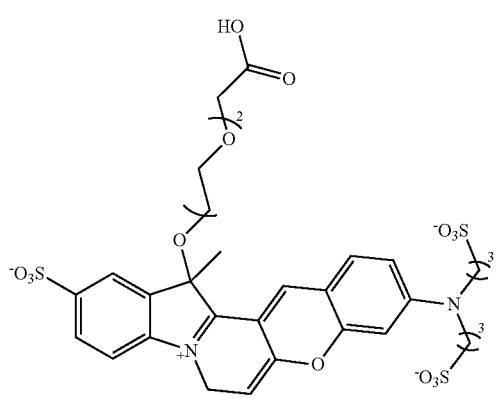
31
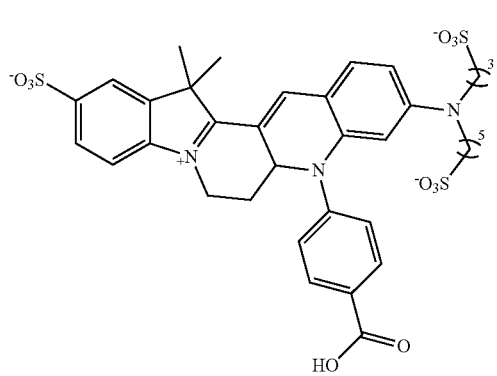
32
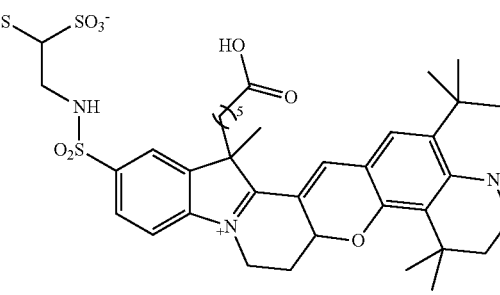

33
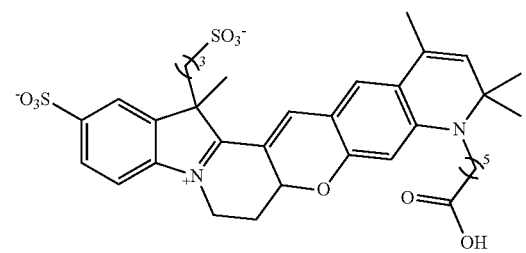
34
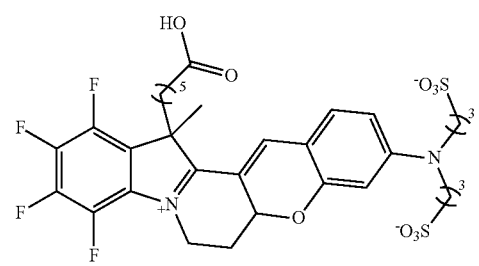
35
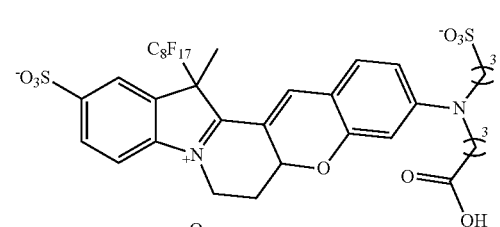
36
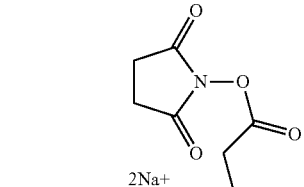
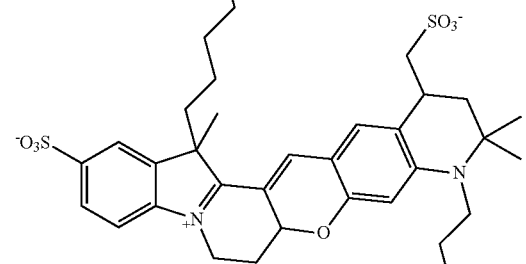
37
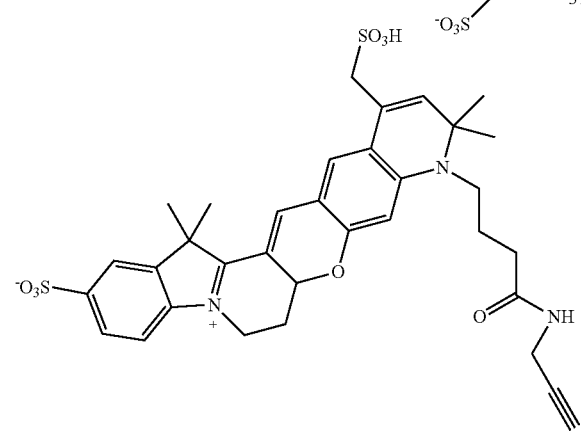
38
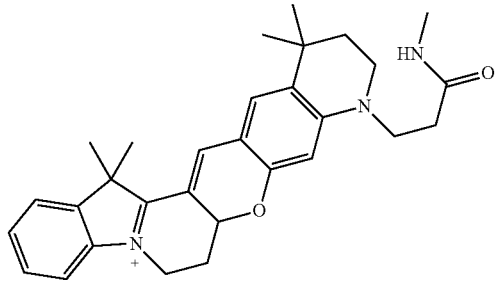
39
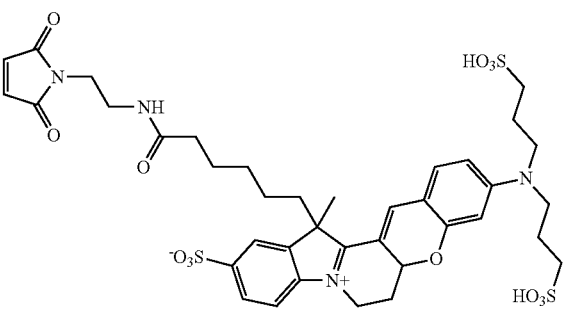
40
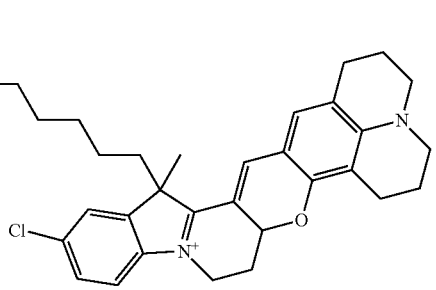
41
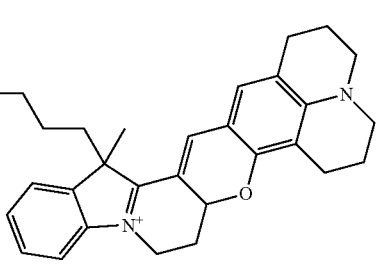

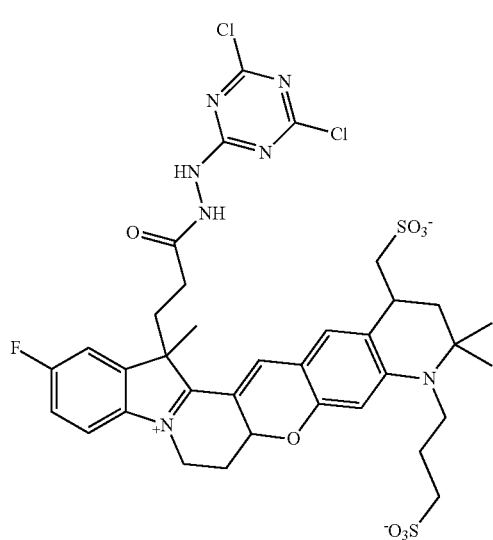
42
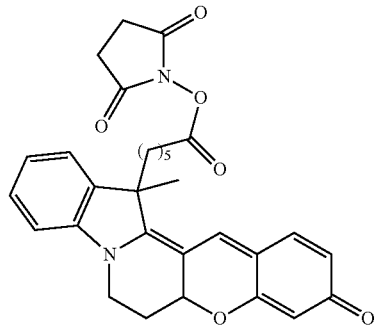
46
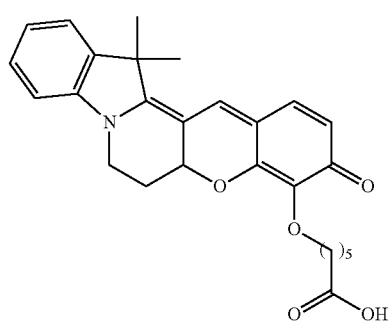
47
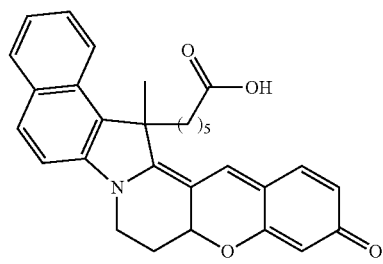
48
43
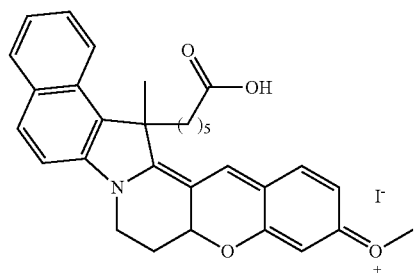
49
44
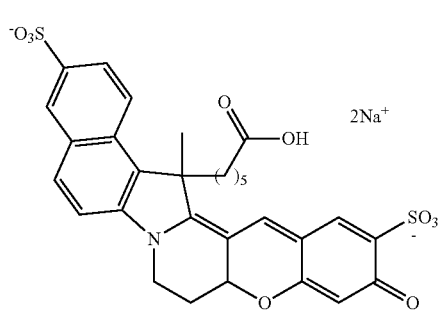
50
45

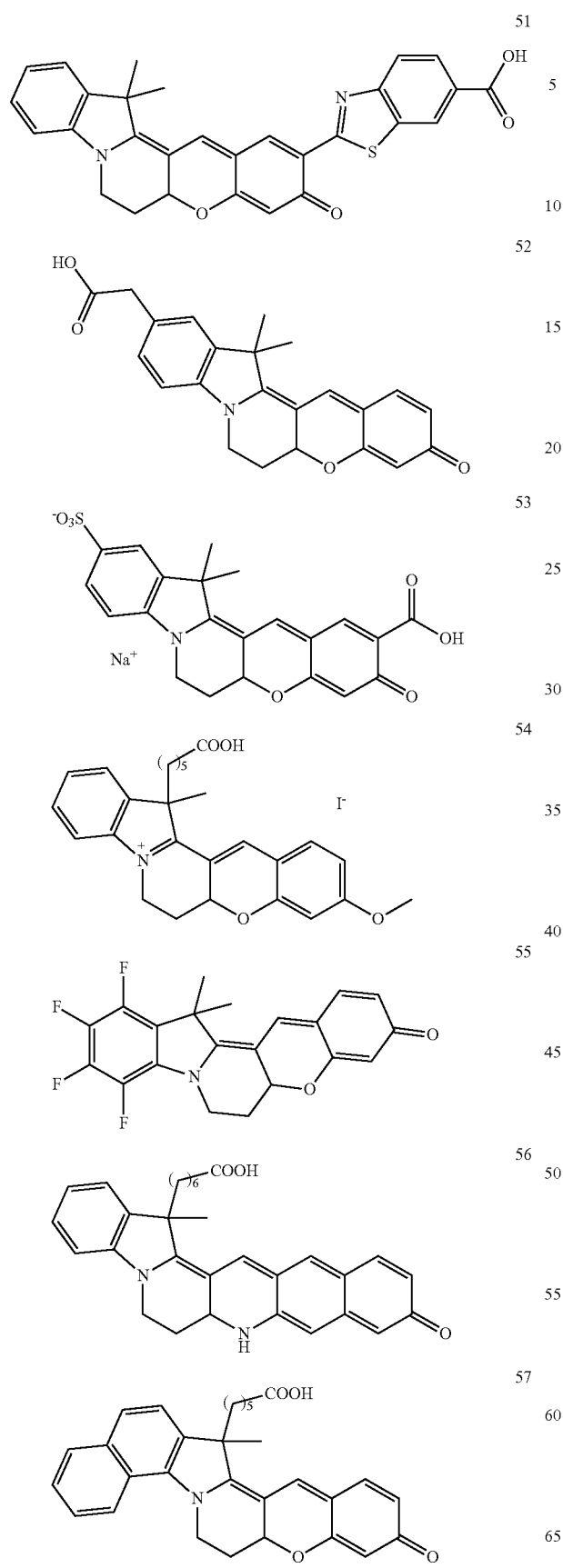
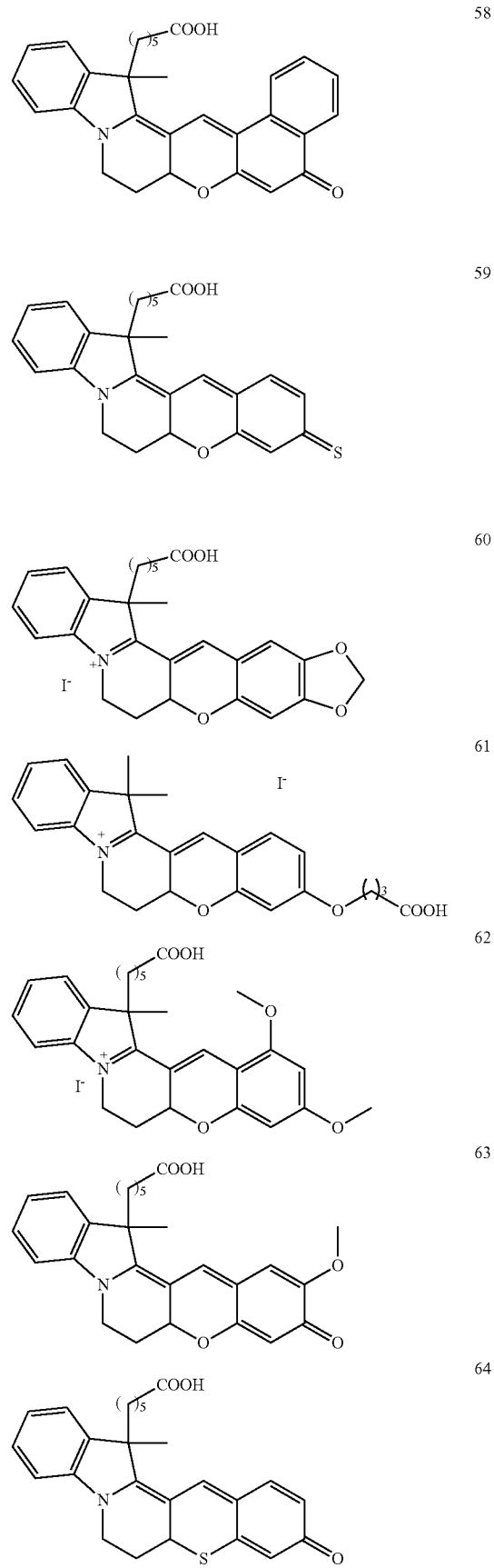

65
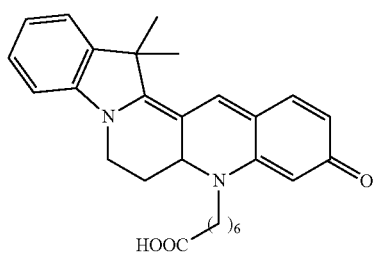
66
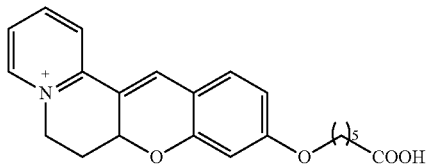
67
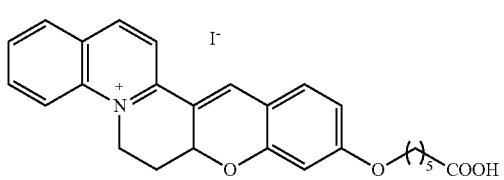
68
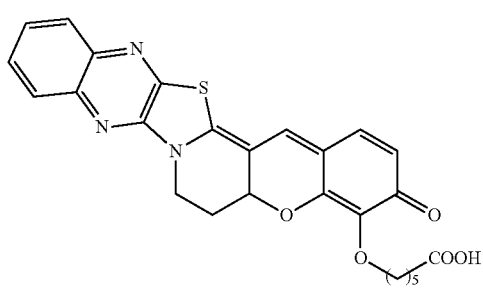
69
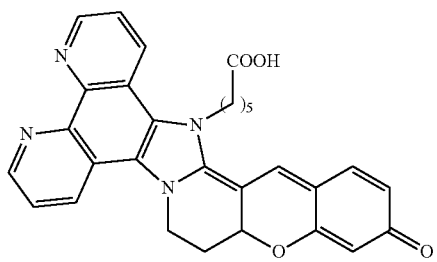
70
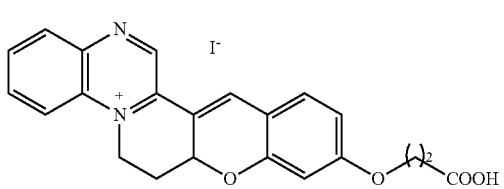
71
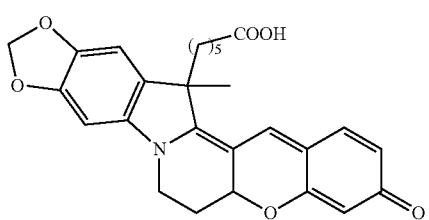
72
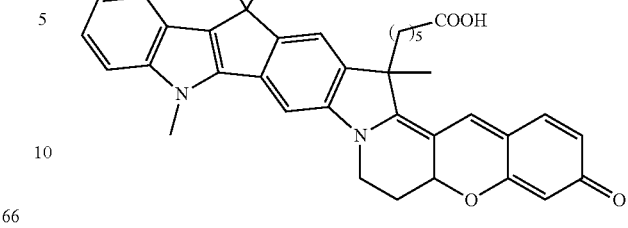
73
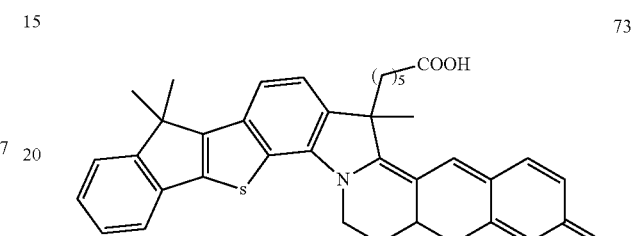
74
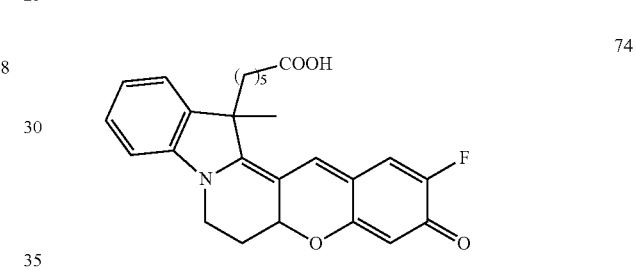
75
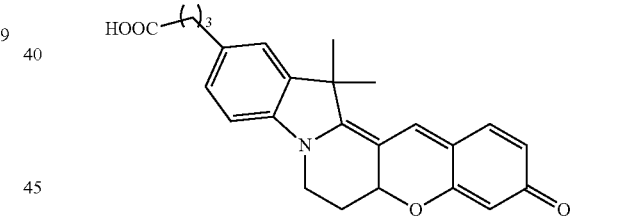
76
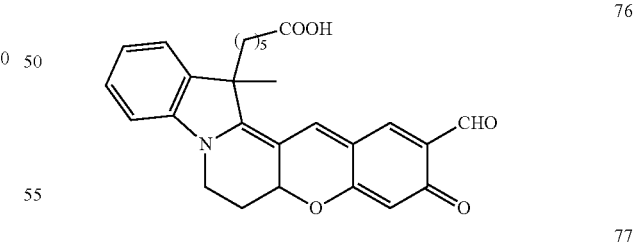
77
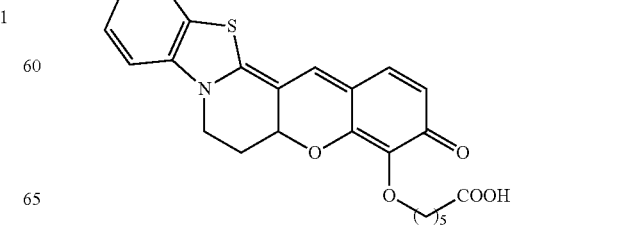

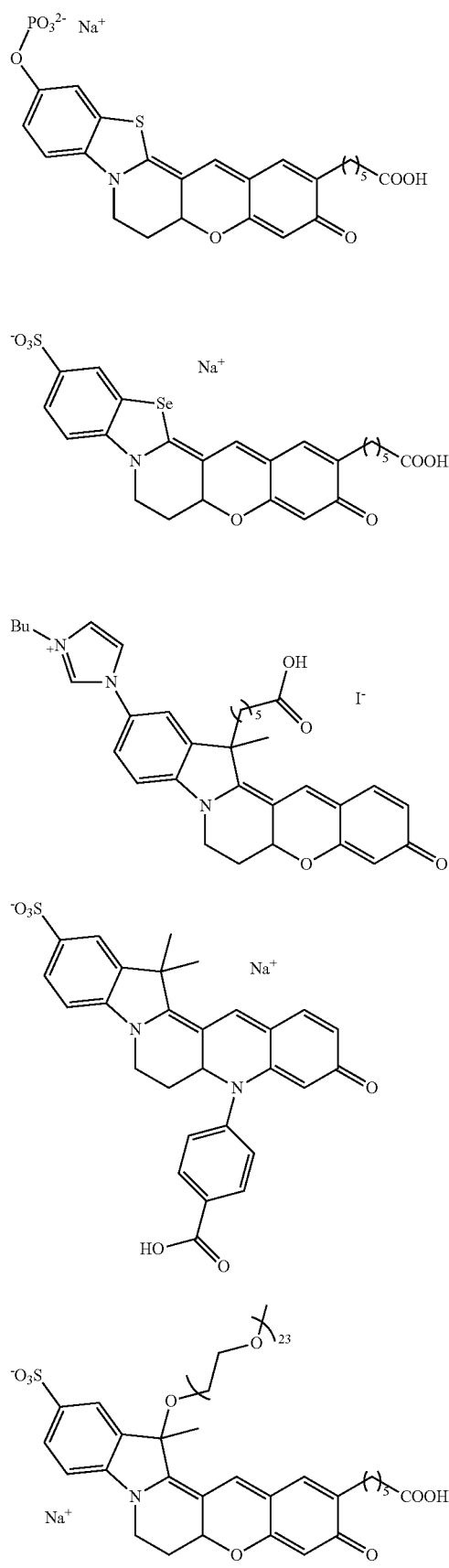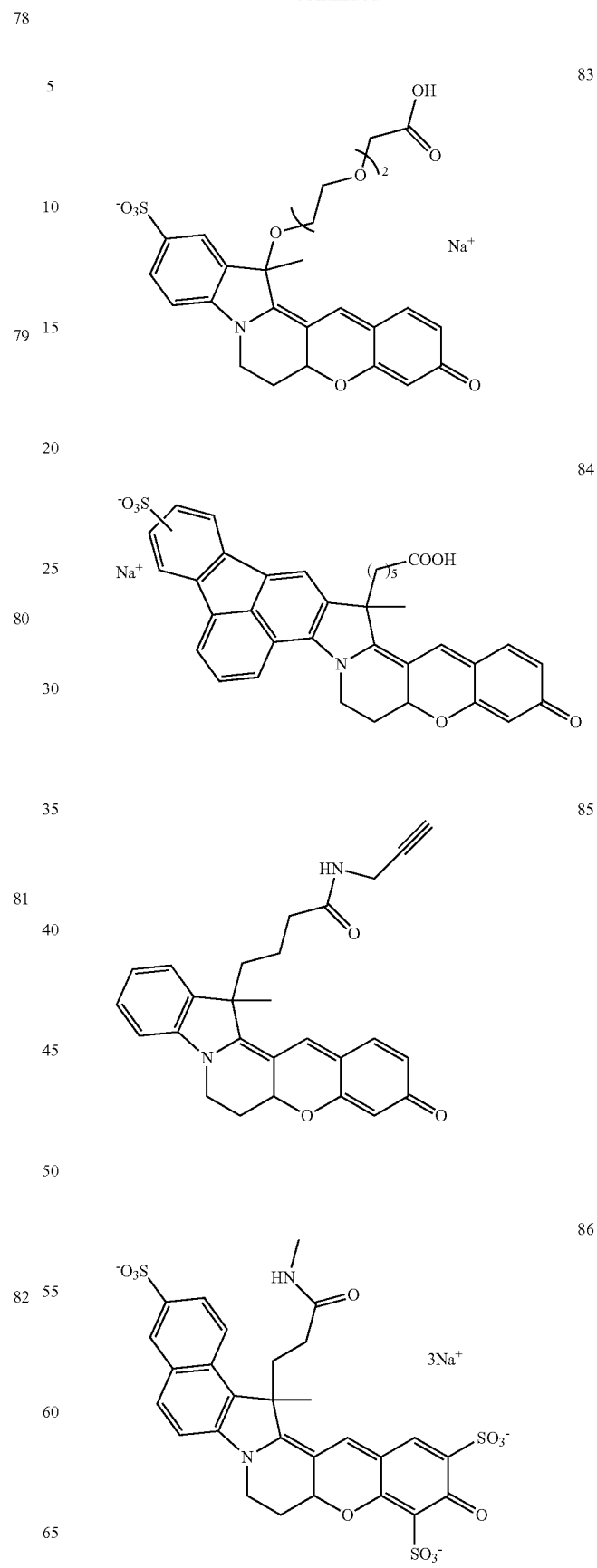

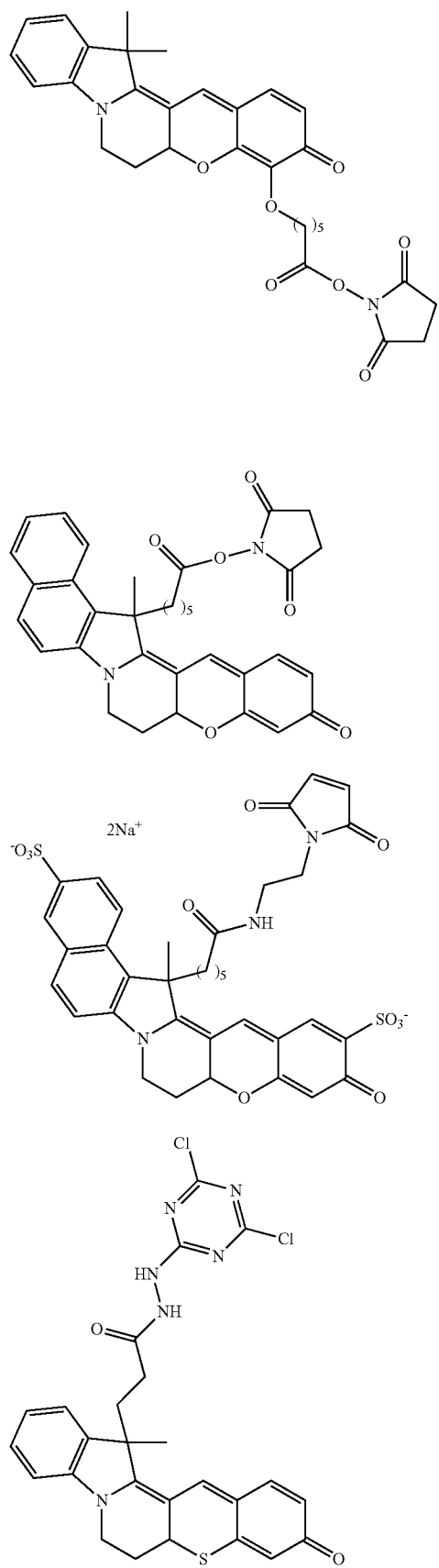
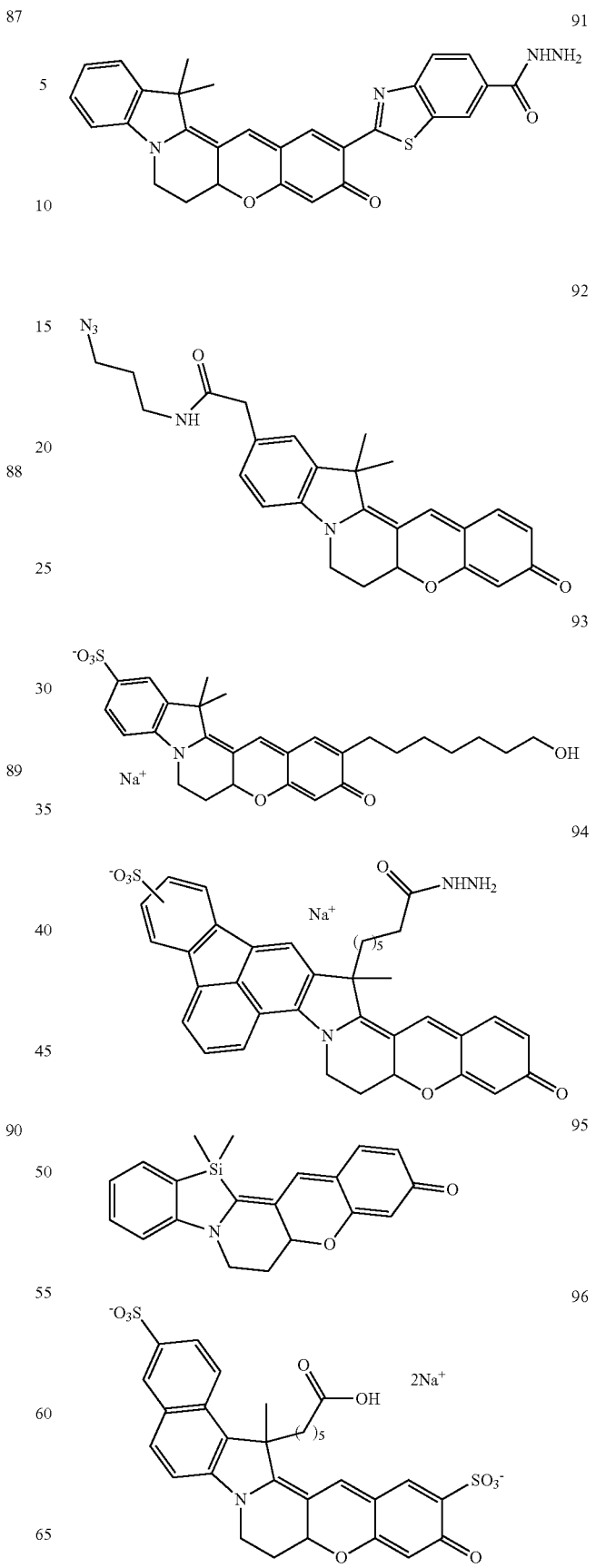

-continued
97
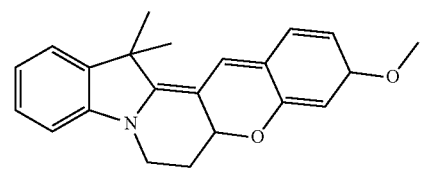
98
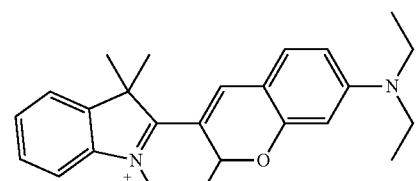
99
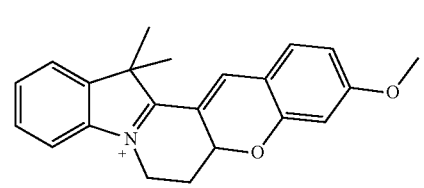
100
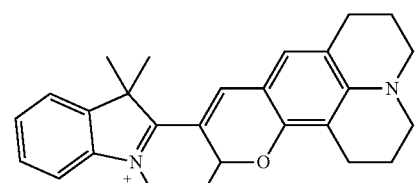
101
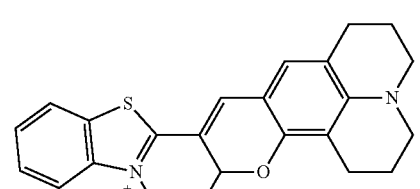
102
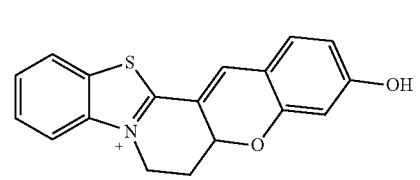
103
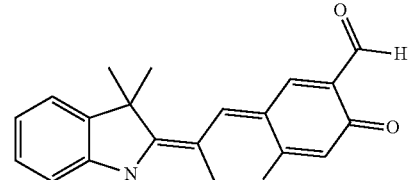
104
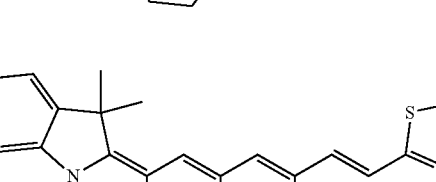
-continued
105
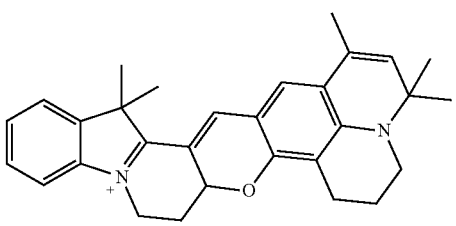
106
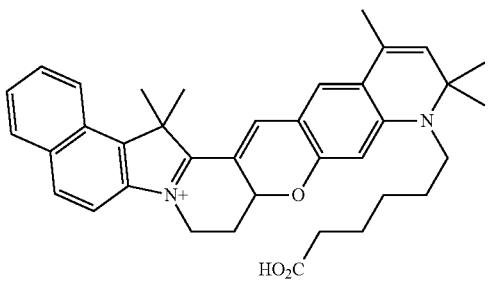
107
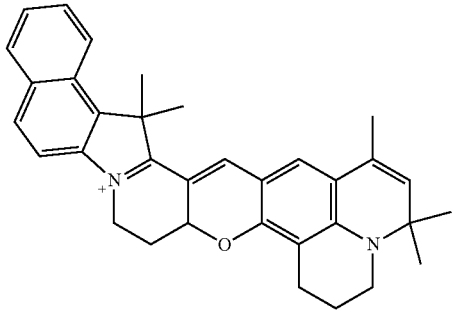
108
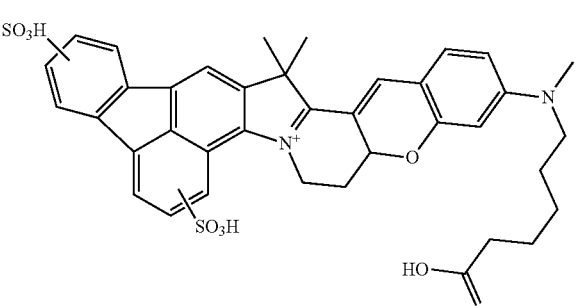
109
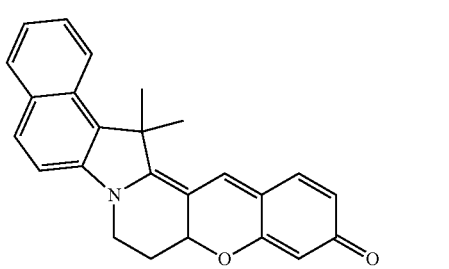
110
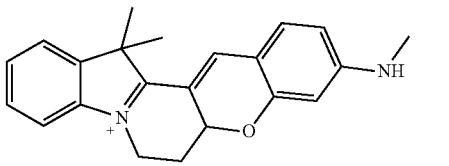

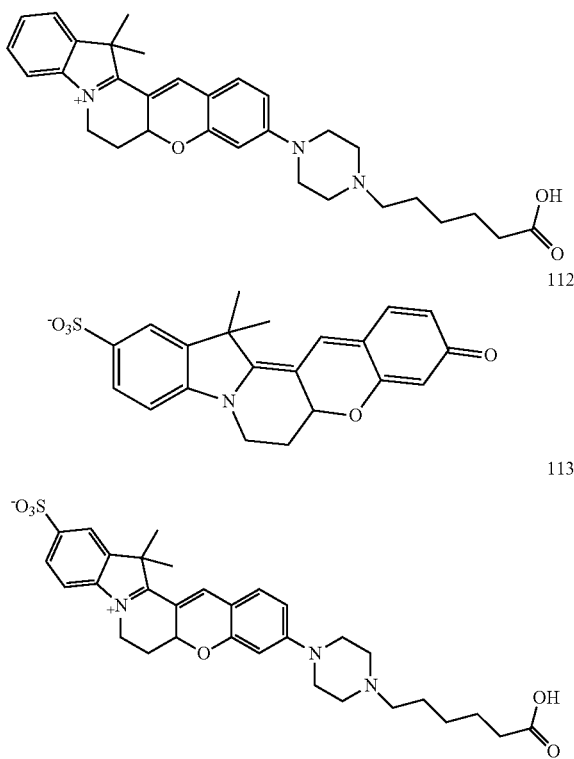

However, the scope of the dye compounds of Formulae I and II according to present invention is not limited to the compounds of Formulae 1 to 113.

The dye compounds of the present invention have the ability to selectively stain and image intracellular mitochondria. Due to this ability, the dye compounds of the present invention can be used as probes capable of labeling and tracking mitochondria (i.e. mitotrackers).

Particularly, the dye compounds of the present invention can be designed to emit fluorescence at various wavelengths so that a user can choose and use any of the dye compounds emitting fluorescence at a desired wavelength as a mitotracker. The reason why mitotrackers having various wavelengths are necessary is that selective design of mitotrackers emitting fluorescence at various wavelengths with narrow bandwidths is considered as a commercially very important factor because their fluorescence is difficult to analyze when overlapping with the fluorescence wavelengths of other probes.

The fluorescence intensities of the dye compounds according to the present invention vary in response to intracellular pH change. Based on this pH-dependent behavior, the dye compounds of the present invention can be utilized as pH probes and even in intracellular pH sensors for measuring intracellular pH.

The measurement of intracellular pH and cytosolic pH using the dye compounds of the present invention enables direct or indirect identification of cellular functions such as ionic homeostasis, reactive oxygen species balance, apoptosis, cell cycle, and cellular mobility.

Particularly, the dye compounds of the present invention can be selected to emit strong fluorescence under acidic conditions at pH 2-6 or under basic conditions at pH 8-12. This selective use makes the dye compounds more useful as pH probes.

The dye compounds of the present invention can be used in various application fields where pH measurement is required, including not only methods for pH measurement through cell staining but also recent methods for cellular pH measurement using plate readers.

MODE FOR CARRYING OUT THE INVENTION

Hereinafter, specific methods for synthesizing dye compounds of the present invention will be explained. The present invention will be explained in more detail with reference the following examples and comparative experiments. However, these examples are merely illustrative and are not intended to limit the scope of the invention.

Synthesis Example 1: Synthesis of the Compound Represented by Formula 1

(1) Synthesis of the Compound Represented by Formula 1-a

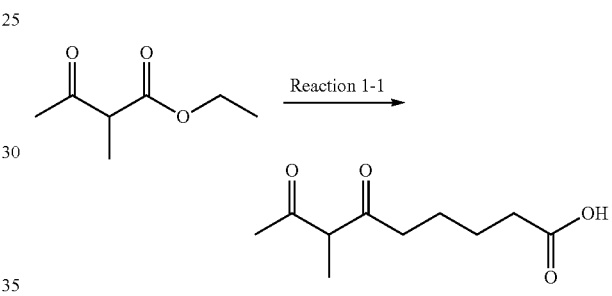

The compound represented by Formula 1-a was synthesized by Reaction 1-1.

Ethyl 2-methylacetatoacetate (23.5 g, 163 mmol) and ethyl 6-bromohexanoate (40.0 g, 179 mmol) were stirred in 200 mL of ethanol. To the mixture was added dropwise liquid sodium ethoxide. The resulting mixture was stirred at 80° C. for 10 h. After completion of the reaction, the solid was filtered off and the filtrate was distilled under reduced pressure. The residue was extracted with dichloromethane and a 2 N solution of hydrochloric acid. The organic layer was treated with anhydrous sodium sulfate, filtered, and distilled under reduced pressure (47.7 g). After removal of the solvent, 300 mL of water was added. The mixture was stirred under reflux for 10 h. After completion of the reaction, the reaction solution was extracted with dichloromethane, treated with sodium sulfate, filtered, and distilled under reduced pressure (25 g, 71%).

LC-MS: m/z=185.84[M+]

(2) Synthesis of the Compound Represented by Formula 1-b

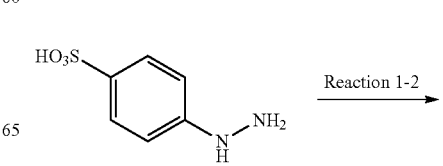

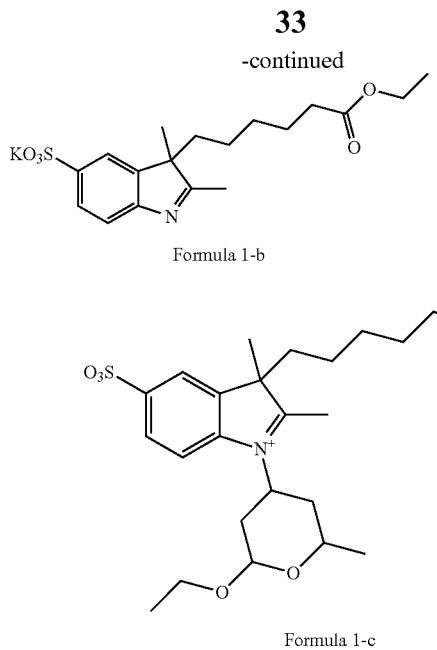

Formula 1-b

Formula 1-c

The compound represented by Formula 1-b was synthesized by Reaction 1-2.

p-Hydrazinobenzenesulfonic acid (20 g, 106 mmol) and the compound represented by Formula 1-a (59.4 g, 319 mmol), which was synthesized by Reaction 1-1, were added to a mixture of a 6 N solution of hydrochloric acid (30 mL) and ethanol (60 mL). The resulting mixture was stirred under reflux for 12 h. The reaction mixture was cooled to room temperature and the resulting solid was filtered. The solid was washed with ethyl acetate and dried under reduced pressure. A solution of the solid (5.1 g, 21.2 mmol) in 35 mL of methanol was added dropwise to a solution of potassium hydroxide (1.4 g, 25.4 mmol) in 35 mL of propanol. Thereafter, the resulting solution was stirred at room temperature for 12 h. The solid was filtered, dried, and purified by C18 reverse-phase chromatography using water/methanol (11.1 g, 30%).

LC-MS: m/z=404.86[M+]

(3) Synthesis of the Compound Represented by Formula 1-c

The compound represented by Formula 1-c was synthesized by Reaction 1-3.

The compound represented by Formula 1-b (3.0 g, 7.4 mmol), which was synthesized by Reaction 1-2, and was stirred in ethanol in a reactor under a stream of nitrogen at room temperature. To the mixture was added dropwise a 48% solution of hydrochloric acid (10.0 mL). After 1 h, the reaction solution was distilled under reduced pressure. Acetonitrile (120.0 mL), acetic acid (3.0 mL), and acrolein diethyl acetal (17.3 g, 133.0 mmol) were added to the reactor. The mixture was allowed to react at 70° C. for 2 h. The reaction solution was distilled under reduced pressure and purified by HPLC (Rainin Dynamax C18, 8 μm column) using water/acetonitrile (0.1% trifluoroacetic acid) as the developing solution at a rate of 20 mL/min to 10-100% for 60 min (1.2 g, 30%).

LC-MS: m/z=496.96[M+]

(4) Synthesis of the Compound Represented by Formula 1-d

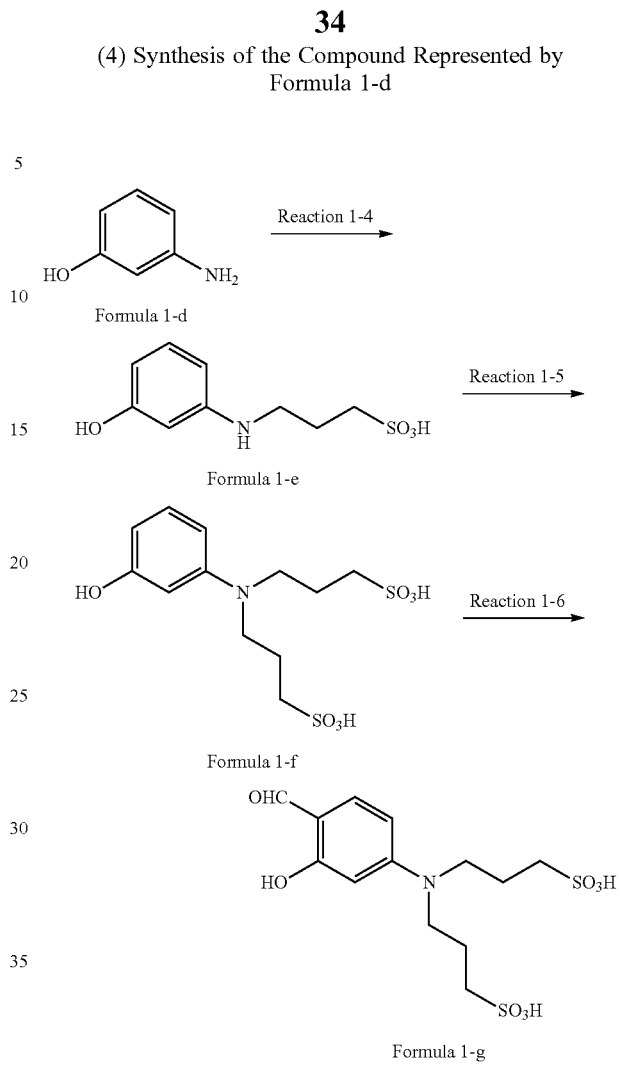

Formula 1-d

Formula 1-e

Formula 1-f

Formula 1-g

The compound represented by Formula 1-3 was synthesized by Reaction 1-4.

3-Aminophenol (5.0 g, 4.5 mmol) and 1,3-propanesultone (0.56 g, 4.6 mmol) were stirred under reflux in n-butanol for 30 min. The reaction solution was cooled to room temperature and stirred overnight. The resulting reaction solution was filtered to separate a gray solid. The solid was washed with methanol (0.8 g, 80%).

LC-MS: m/z=231.30[M+]

(5) Synthesis of the Compound Represented by Formula 1-e

The compound represented by Formula 1-e was synthesized by Reaction 1-5.

The compound represented by Formula 1-d (1 g, 4.3 mmol), which was synthesized by Reaction 1-4, and 1,3-propanesultone (0.54 g, 4.4 mmol) were stirred in 5 mL of N,N-dimethylformamide at 130° C. for 2 h. The reaction solution was cooled to room temperature, distilled under reduced pressure, and purified by reverse-phase chromatography (1.48 g, 95%)

LC-MS: m/z=353.19[M+]

(5) Synthesis of the Compound Represented by Formula 1-f

The compound represented by Formula 1-f was synthesized by Reaction 1-6.

The compound represented by Formula 1-3 (3.0 g, 8.0 mmol), which was synthesized by Reaction 1-5, was put into N,N-dimethylformamide (1.3 g, 8.0 mmol) in a reactor. The reaction was allowed to proceed at 50° C. for 12 h. After completion of the reaction, the reaction mixture was diluted with water and neutralized. After removal of the solvent, the reaction mixture was purified by reverse-phase chromatography (0.8 g, 25%)

LC-MS: m/z=380.84[M+]

(5) Synthesis of the Compound Represented by Formula 1

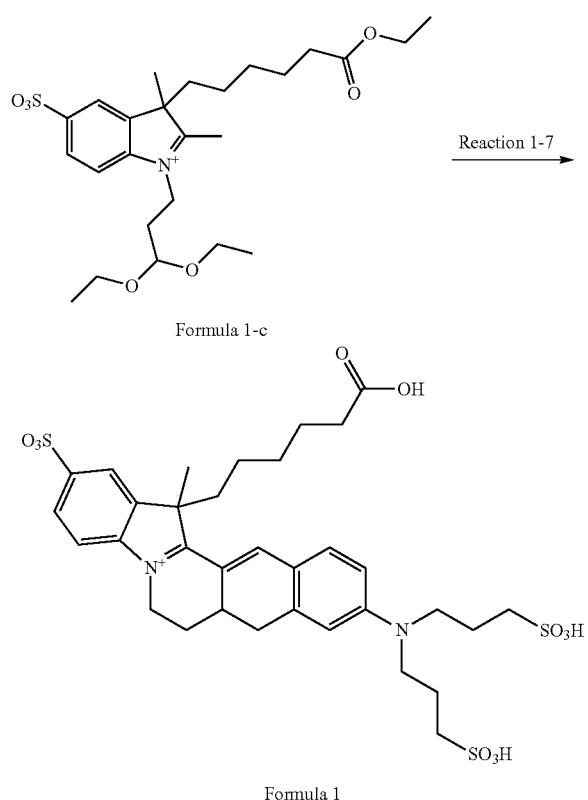

Formula 1-c

Formula 1

The compound represented by Formula 1 was synthesized by Reaction 1-7.

The compound represented by Formula 1-3 (1.0 g, 1.9 mmol), which was synthesized by Reaction 1-3, and the compound represented by Formula 1-f (0.8 g, 1.9 mmol), which was synthesized by Reaction 6, were dissolved in 20 mL ethanol 20 mL. The solution was stirred at 80° C. for 8 h. After completion of the reaction, the reaction mixture was concentrated under reduced pressure to remove the solvent. The concentrate was dissolved in 50 mL of chloroform and 1 mL of 50% sulfuric acid was added dropwise thereto. The mixture was diluted with dichloromethane and extracted with water. The organic layer was concentrated under reduced pressure and purified by HPLC (Rainin Dynamax C18, 8 μm column) using water/acetonitrile (0.1% trifluoroacetic acid) as the developing solution at a rate of 20 mL/min to 10-100% for 60 min (0.4 g, 51%).

LC-MS: m/z=739.79[M+]

Synthesis Example 2: Synthesis of the Compound Represented by Formula 2

(1) Synthesis of the Compound Represented by Formula 2-a

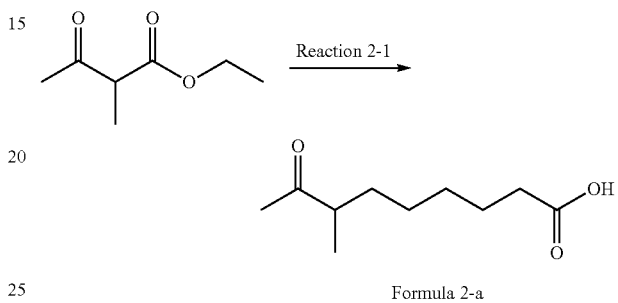

Formula 2-a

The compound represented by Formula 2-a was synthesized by Reaction 2-1.

Ethyl 2-methylacetatoacetate (23.5 g, 163 mmol) and ethyl 6-bromohexanoate (40.0 g, 179 mmol) were stirred in 200 mL of ethanol and liquid sodium ethoxide was added dropwise thereto. The mixture was stirred at 80° C. for 10 h. After completion of the reaction, the solid was filtered off and the filtrate was distilled under reduced pressure. The residue was extracted with dichloromethane and a 2 N solution of hydrochloric acid. The organic layer was treated with anhydrous sodium sulfate, filtered, and distilled under reduced pressure (47.7 g). After removal of the solvent, 300 mL of water was added, followed by reflux for 10 h. After completion of the reaction, the reaction solution was extracted with dichloromethane. The extract was treated with sodium sulfate, filtered, and distilled under reduced pressure (25 g, 71%).

LC-MS: m/z=185.84[M+]

(2) Synthesis of the Compound Represented by Formula 2-b

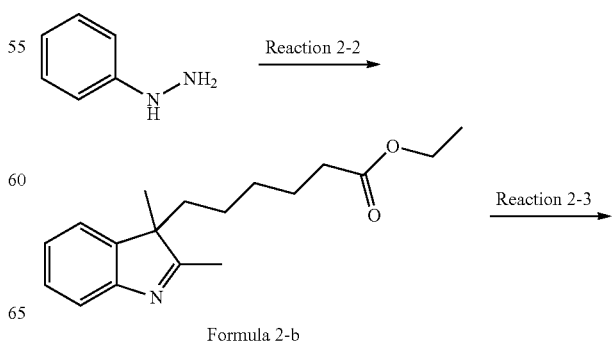

Formula 2-b

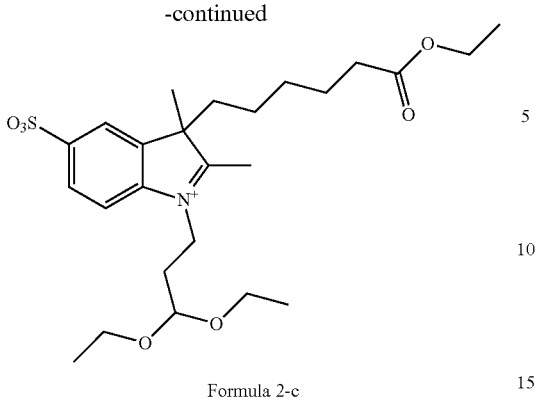

Formula 2-c

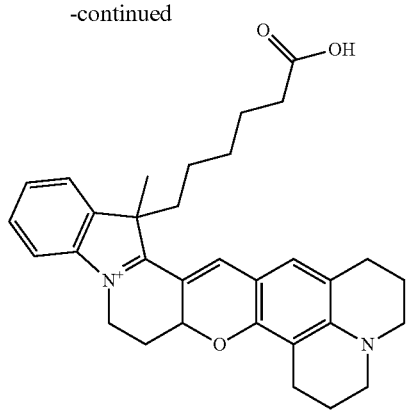

Formula 2

The compound represented by Formula 2-b was synthesized by Reaction 2-2.

Phenylhydrazine hydrochloride (5.0 g, 34.6 mmol) and the compound represented by Formula 2-a (32.2 g, 173 mmol), which was synthesized by Formula 2-1, were added to a mixture of a 6 N solution of hydrochloric acid (30 mL) and ethanol (60 mL). The resulting mixture was stirred under reflux for 12 h. After cooling to room temperature, to the reaction solution was added dropwise ethyl acetate. The precipitated solid was filtered off. The filtrate was distilled under reduced pressure and purified by silica gel column chromatography to afford the desired compound as a liquid (3.2 g, 61%).

LC-MS: m/z=296.89[M+]

(3) Synthesis of the Compound Represented by Formula 2-c

The compound represented by Formula 2-c was synthesized by Reaction 2-3.

The compound represented by Formula 2-b (3.0 g, 7.4 mmol), which was synthesized by Reaction 2-2, was stirred in ethanol in a reactor at room temperature under a stream of nitrogen and a 48% solution of hydrochloric acid (10.0 mL) was added dropwise thereto. After 1 h, the reaction solution was distilled under reduced pressure. Acetonitrile (120.0 mL), acetic acid (3.0 mL), and acrolein diethyl acetal (17.3 g, 133.0 mmol) were added to the reactor. The mixture was allowed to react at 70° C. for 2 h. The reaction solution was distilled under reduced pressure and purified by HPLC (Rainin Dynamax C18, 8 μm column) using water/acetonitrile (0.1% trifluoroacetic acid) as the developing solution at a rate of 20 mL/min to 10-100% for 60 min (1.2 g, 30%).

LC-MS: m/z=418.01[M+]

(4) Synthesis of the Compound Represented by Formula 2

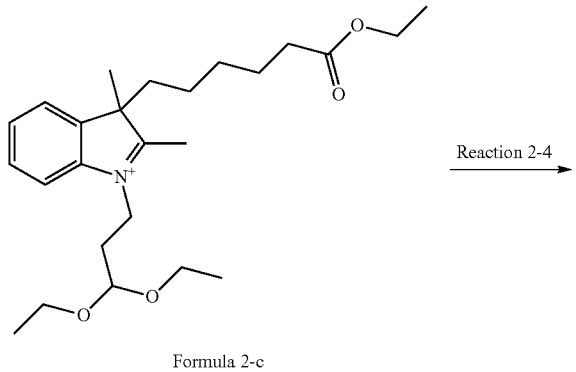

Formula 2-c

Reaction 2-4 →

The compound represented by Formula 2 was synthesized by Reaction 2-4.

The compound represented by Formula 2-c (1.0 g, 1.9 mmol), which was synthesized by Reaction 2-3, and 9-formyl-8-hydroxyjulolidine (0.8 g, 1.9 mmol) were dissolved in 20 mL of ethanol. The solution was stirred at 80° C. for 8 h. After completion of the reaction, the reaction solution was concentrated under reduced pressure to remove the solvent. The concentrate was dissolved in 50 mL of chloroform and 1 mL of 50% sulfuric acid was added dropwise thereto. The mixture was diluted with dichloromethane and extracted with water. The extract was distilled under reduced pressure and the residue was purified by silica gel column chromatography (0.3 g, 40%).

LC-MS: m/z=496.91[M+]

Synthesis Example 3: Synthesis of the Compound Represented by Formula 3

(1) Synthesis of the Compound Represented by Formula 3-a

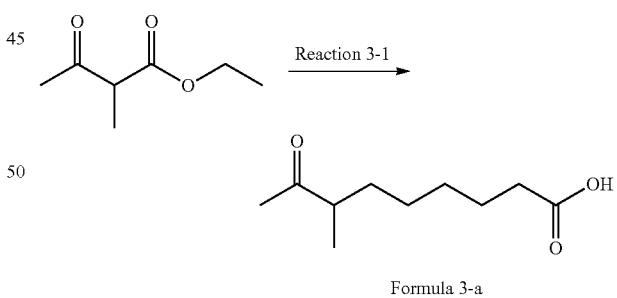

Formula 3-a

The compound represented by Formula 3-a was synthesized by Reaction 3-1.

Ethyl 2-methylacetatoacetate (23.5 g, 163 mmol) and ethyl 6-bromohexanoate (40.0 g, 179 mmol) were stirred in 200 mL of ethanol and liquid sodium ethoxide was added dropwise thereto. The mixture was stirred at 80° C. for 10 h. After completion of the reaction, the solid was filtered off and the filtrate was distilled under reduced pressure. The residue was extracted with dichloromethane and a 2 N aqueous solution of hydrochloric acid. The organic layer was treated with anhydrous sodium sulfate, filtered, and distilled under reduced pressure (47.7 g) to remove the solvent. 300 mL of water was added to the residue, followed by stirring under reflux for 10 h. After completion of the reaction, the reaction solution was extracted with dichloromethane, treated with sodium sulfate, filtered, and distilled under reduced pressure (25 g, 71%)

LC-MS: m/z=185.84[M+]

(2) Synthesis of the Compound Represented by Formula 3-b

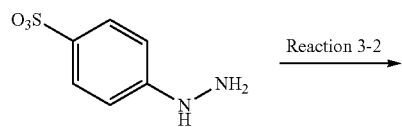

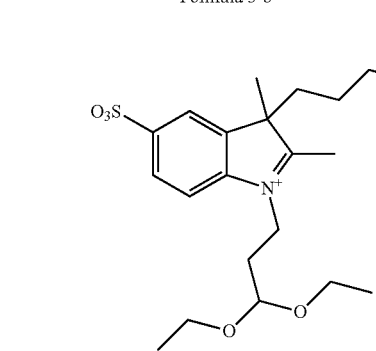

Formula 3-c

The compound represented by Formula 3-b was synthesized by Reaction 3-2.

p-Hydrazinobenzenesulfonic acid (20 g, 106 mmol) and the compound represented by Formula 3-a (59.4 g, 319 mmol), which was synthesized in Reaction 3-1, were added to a mixture of a 6 N aqueous solution of hydrochloric acid (30 mL) and ethanol (60 mL). The resulting mixture was stirred under reflux for 12 h. The reaction solution was cooled to room temperature. The resulting solid was filtered, washed with ethyl acetate, and dried under reduced pressure. A solution of the solid (5.1 g, 21.2 mmol) in 30 mL of methanol was added dropwise to a solution of potassium hydroxide (1.4 g, 25.4 mmol) in 35 ml of propanol. Thereafter, the resulting solution was stirred at room temperature for 12 h. The solid was filtered, dried, and purified by C18 reverse-phase chromatography using water/methanol (11.1 g, 30%).

LC-MS: m/z=404.86[M+]

(3) Synthesis of the Compound Represented by Formula 3-c

The compound represented by Formula 3-c was synthesized by Reaction 3-3.

The compound represented by Formula 3-b (3.0 g, 7.4 mmol), which was synthesized by Reaction 3-2, was stirred in ethanol in a reactor at room temperature under a stream of nitrogen and a 48% aqueous solution of hydrochloric acid (10.0 mL) was added dropwise thereto. After 1 h, the reaction solution was distilled under reduced pressure. Acetonitrile (120.0 mL), acetic acid (3.0 mL), and acrolein diethyl acetal (17.3 g, 133.0 mmol) were added to the reactor. The reaction was allowed to proceed at 70° C. for 2 h. The reaction solution was distilled under reduced pressure and purified by HPLC (Rainin Dynamax C18, 8 μm column) using water/acetonitrile (0.1% trifluoroacetic acid) as the developing solution at a rate of 20 mL/min to 10-100% for 60 min (1.2 g, 30%).

LC-MS: m/z=496.96[M+]

(4) Synthesis of the Compound Represented by Formula 3-d

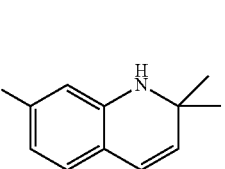

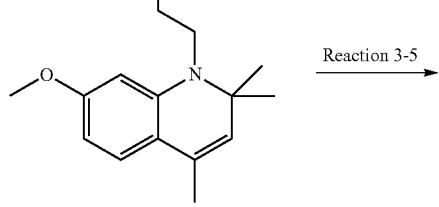

Formula 3-d

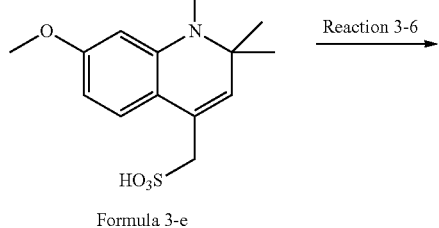

Formula 3-e

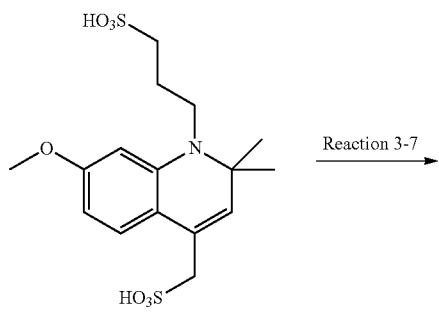

Formula 3-f

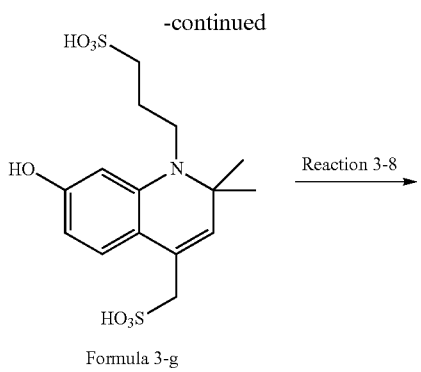

Formula 3-g

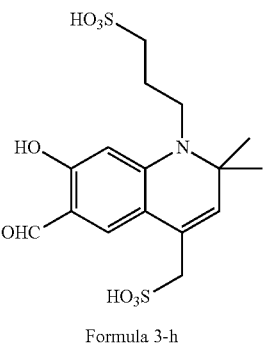

Formula 3-h

The compound represented by Formula 3-d was synthesized by Reaction 3-4.

7-Methoxy-2,2,4-trimethyl-1,2-hydroquinoline (10.0 g, 49 mmol) and 1,3-propanesulfone (6.6 g, 54 mmol) were stirred at 145° C. for 3 h. After completion of the reaction, the reaction mixture was purified by column chromatography using dichloromethane and methanol (10.0 g, 63%).

LC-MS: m/z=325.01[M+]

(5) Synthesis of the Compound Represented by Formula 3-e

The compound represented by Formula 3-e was synthesized by Reaction 3-5.

The compound represented by Formula 3-d (10.0 g, 31 mmol), which was synthesized by Reaction 3-4, was placed in a reactor and sulfonic acid (9.8 mL) was added dropwise thereto. The mixture was stirred for 30 min. To the reaction mixture was added dropwise 20.0% oleum (3.9 mL) at 0° C. The reaction was allowed to proceed for 48 h. After completion of the reaction, the reaction mixture was added to cold water, neutralized with sodium hydroxide, and recrystallized from ethanol (11.0 g, 88%).

LC-MS: m/z=404.88[M+]

(6) Synthesis of the Compound Represented by Formula 3-f

The compound represented by Formula 3-f was synthesized by Reaction 3-6.

The compound represented by Formula 3-e (12.0 g, 30.0 mmol), which was synthesized by Reaction 3-5, 10% Pd/C (0.9 g), and 120 mL of methanol were stirred under a hydrogen atmosphere at room temperature for 12 h. The resulting solid was filtered off. The filtrate was distilled under reduced pressure and recrystallized from ethanol (11.5 g, 95%).

LC-MS: m/z=406.78[M+]

(7) Synthesis of the Compound Represented by Formula 3-g

The compound represented by Formula 3-g was synthesized by Reaction 3-7.

The compound represented by Formula 3-f (12.0 g, 29.0 mmol), which was synthesized by Reaction 3-6, sodium iodide (11.0 g, 74.0 mmol), and hydrogen bromide (72.0 g, 174.0 mmol) were stirred in a reactor at 105° C. for 12 h. After completion of the reaction, the reaction mixture was neutralized with an aqueous solution of sodium bicarbonate. The solvent was removed and a crystal was precipitated with water/acetone/ethanol. The crystal was recrystallized from methanol/acetone and washed with acetone (3.0 g, 27%).

LC-MS: m/z=392.93[M+]

(8) Synthesis of the Compound Represented by Formula 3-h

The compound represented by Formula 3-h was synthesized by Reaction 3-8.

The compound represented by Formula 3-g (3.0 g, 8.0 mmol), which was synthesized by Reaction 3-7, was put into N,N-dimethylformamide (1.3 g, 8.0 mmol) in a reactor. The reaction was allowed to proceed at 50° C. for 12 h. After completion of the reaction, the reaction mixture was diluted with water and neutralized. After removal of the solvent, a crystal was precipitated with methanol/acetone. The crystal was recrystallized from ethanol (0.8 g, 25%).

LC-MS: m/z=420.74[M+]

(9) Synthesis of the Compound Represented by Formula 3

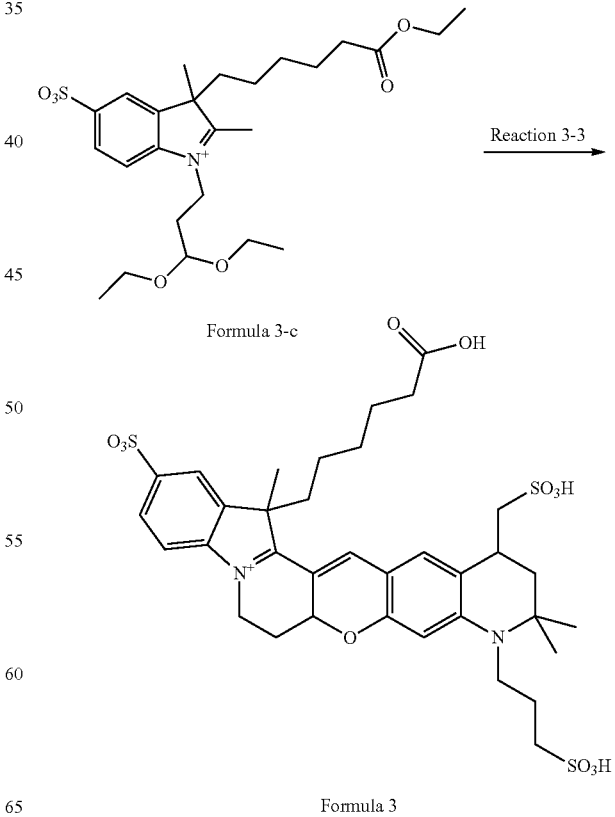

Formula 3-c

Formula 3

The compound represented by Formula 3 was synthesized by Reaction 3-9.

The compound represented by Formula 3-c (1.0 g, 1.9 mmol), which was synthesized by Reaction 3-3, and the compound represented by Formula 3-h (0.8 g, 1.9 mmol), which was synthesized by Reaction 8, were dissolved in 20 mL of ethanol. The solution was stirred at 80° C. for 8 h. After completion of the reaction, the reaction solution was concentrated under reduced pressure to remove the solvent. The concentrate was dissolved in 50 mL of chloroform and 1 mL of 50% sulfuric acid was added dropwise thereto. The mixture was diluted with dichloromethane and extracted with water. The organic layer was concentrated under reduced pressure and purified by HPLC (Rainin Dynamax C18, 8 μm column) using water/acetonitrile (0.1% trifluoroacetic acid) as the developing solution at a rate of 20 mL/min to 10-100% for 60 min (0.4 g, 51%).

LC-MS: m/z=780.01[M+]

(10) Synthesis of the Compound Represented by Formula 36 (3-NHS)

The compound represented by Formula 3-NHS was synthesized by the above reaction.

The compound represented by Formula 3 (0.24 g, 0.5 mmol), which was synthesized by Reaction 3-9, N-hydroxysuccinimide (0.03 g, 0.03 mmol), and N,N-dicyclohexylcarbodiimide (0.054 g, 0.03 mmol) were dissolved in N,N-dimethylformamide (1 ml). The solution was stirred at room temperature for 1 h. After completion of the reaction, the reaction solution was purified by HPLC (Rainin Dynamax C18, 8 μm column) using water/acetonitrile (0.1% trifluoroacetic acid) as the developing solution at a rate of 20 mL/min to 10-100% for 60 min (0.15 g, 56.6%).

Synthesis Example 4: Synthesis of the Compound Represented by Formula 4

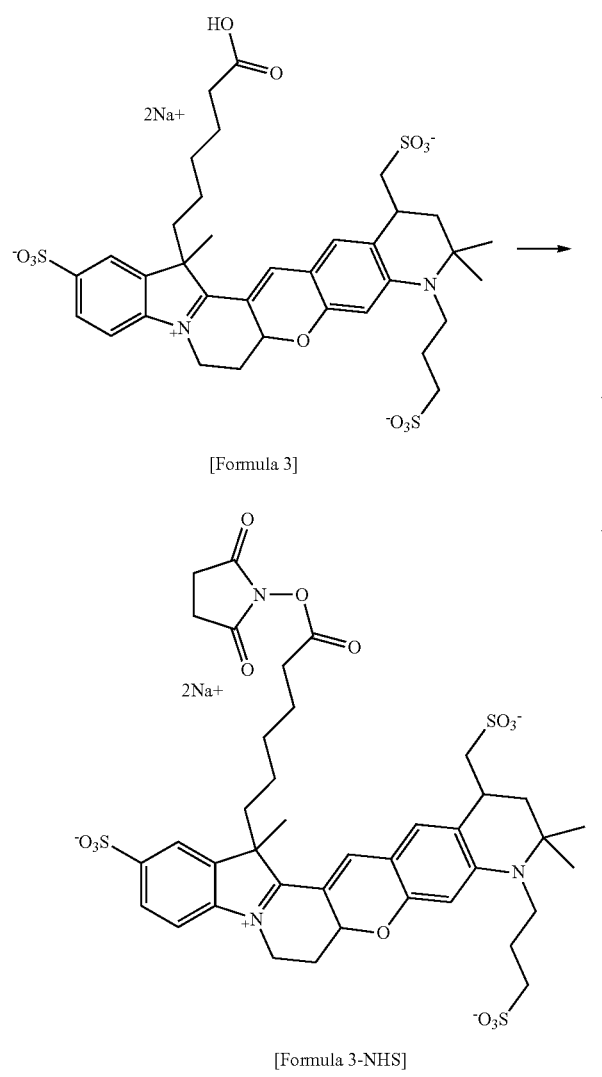

[Formula 3]

[Formula 3-NHS]

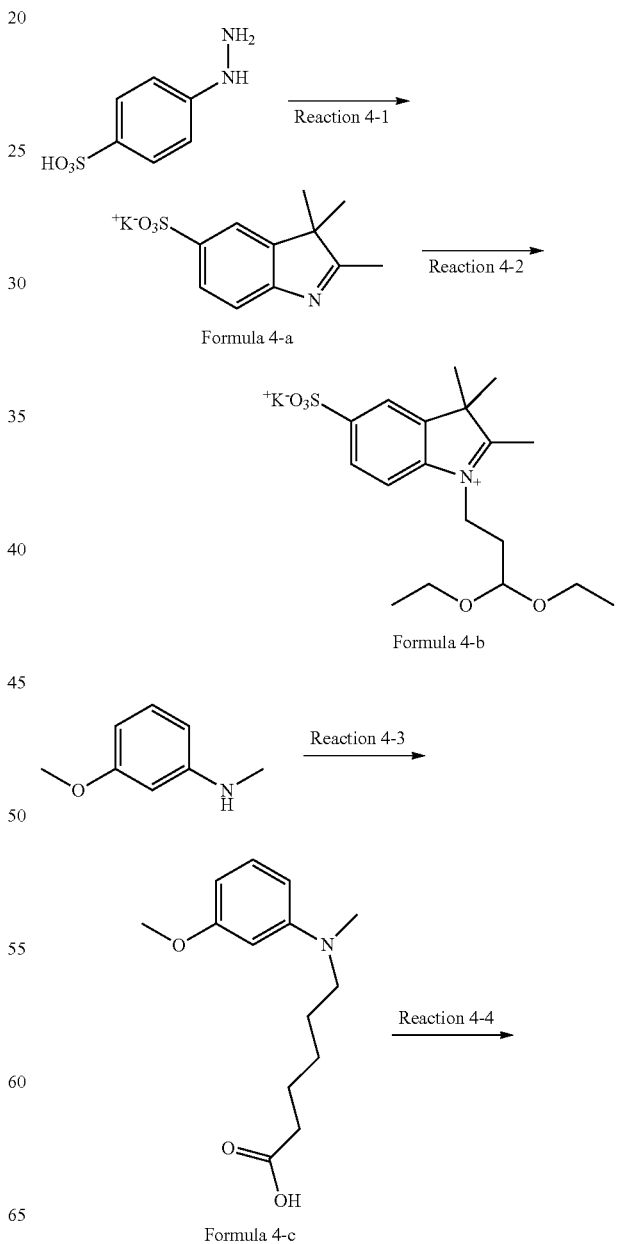

Formula 4-a

Formula 4-b

Formula 4-c

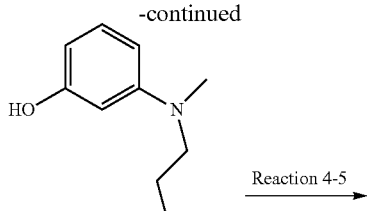

Formula 4-d

Reaction 4-5 →

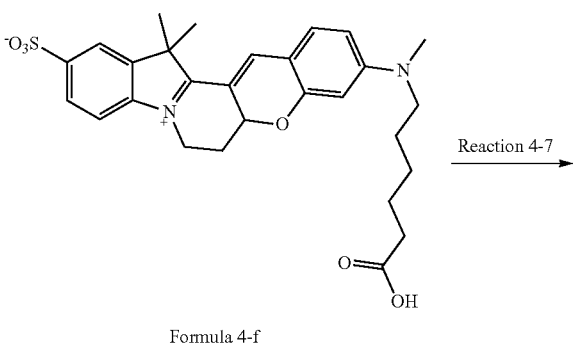

Formula 4-e

Reaction 4-6 →

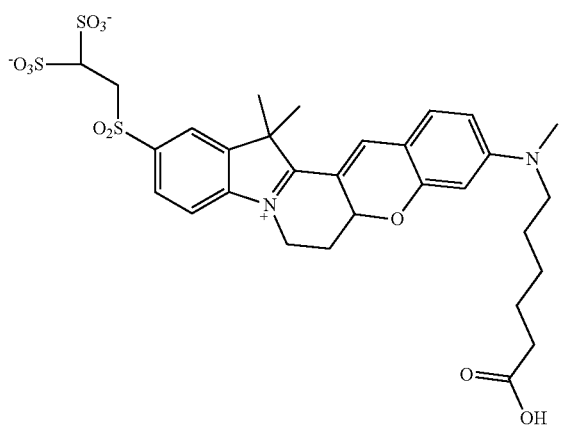

Formula 4-f

Reaction 4-7 →

(1) Synthesis of the Compound Represented by Formula 4-a

The compound represented by Formula 4-a was synthesized by Reaction 4-1.

As in Reaction 1-2, the compound represented by Formula 4-a (11.1 g, 30%) was synthesized using p-hydrazinobenzenesulfonic acid (20 g, 106 mmol) and 3-methyl-2-butanone (27.48 g, 319 mmol).

LC-MS: m/z=277.02[M+]

(2) Synthesis of the Compound Represented by Formula 4-b

The compound represented by Formula 4-b was synthesized by Reaction 4-2.

As in Reaction 1-3, the compound represented by Formula 4-2 (5.0 g, 34.0%) was synthesized using the compound represented by Formula 4-a, which was synthesized by Reaction 4-1.

LC-MS: m/z=408.12[M+]

(3) Synthesis of the Compound Represented by Formula 4-c

The compound represented by Formula 4-c was synthesized by Reaction 4-3.

3-Methoxy-N-methylaniline (10.0 g, 73.0 mmol) and 6-bromohexanoic acid (17.1 g, 87.5 mmol) were stirred under reflux in 100 mL of N,N-dimethylformamide. After completion of the reaction, the reaction solution was purified by column chromatography (13.6 g, 74.3%).

LC-MS: m/z=252.15[M+]

(4) Synthesis of the Compound Represented by Formula 4-d

The compound represented by Formula 4-d was synthesized by Reaction 4-4.

As in Reaction 3-7, the compound represented by Formula 4-d (5.1 g, 45.6%) was synthesized using the compound represented by Formula 4-d, which was synthesized by Reaction 4-4.

LC-MS: m/z=238.14[M+]

(5) Synthesis of the Compound Represented by Formula 4-e

The compound represented by Formula 4-e was synthesized by Reaction 4-5.

As in Reaction 1-6, the compound represented by Formula 4-e (2.0 g, 35.1%) was synthesized using the compound represented by Formula 4-d, which was synthesized by Reaction 4-5.

LC-MS: m/z=266.13[M+]

(6) Synthesis of the Compound Represented by Formula 4-f

The compound represented by Formula 4-f was synthesized by Reaction 4-6.

As in Reaction 1-7, the compound represented by Formula 4-f (0.46 g, 23.5%) was synthesized using the compound represented by Formula 4-b, which was synthesized by Reaction 4-2, and the compound represented by Formula 4-e, which was synthesized by Reaction 4-5.

LC-MS: m/z=525.20[M+]

(7) Synthesis of the Compound Represented by Formula 4

The compound represented by Formula 4 was synthesized by Reaction 4-7.

The compound represented by Formula 4-b (1.0 g, 1.9 mmol), which was synthesized by Reaction 4-2, was dissolved in 1.0 ml of N,N-dimethylformamide, 0.5 ml of phosphonyl chloride was added thereto, followed by heating. To the mixture was added 2-aminoethane-1,1-disulfonic acid. After stirring at room temperature, the reaction mixture was purified by column chromatography (0.2 g, 15.2%).

LC-MS: m/z=696.14[M+]

Synthesis Example 5: Synthesis of the Compound Represented by Formula 5

(1) Synthesis of the Compound Represented by Formula 5-a

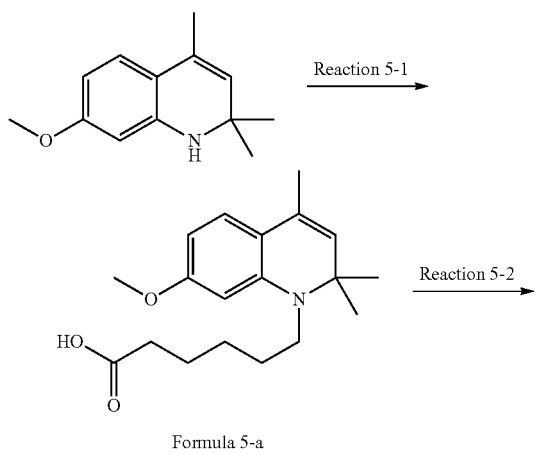

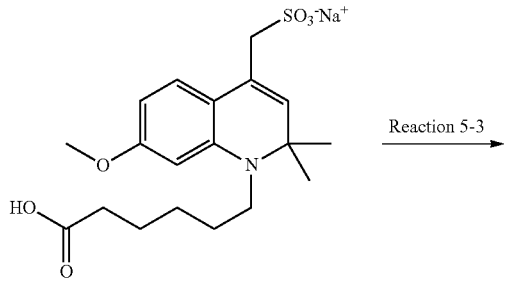

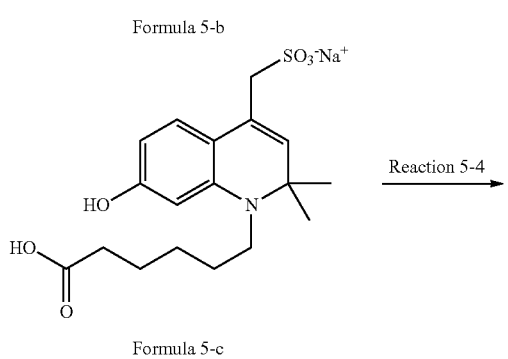

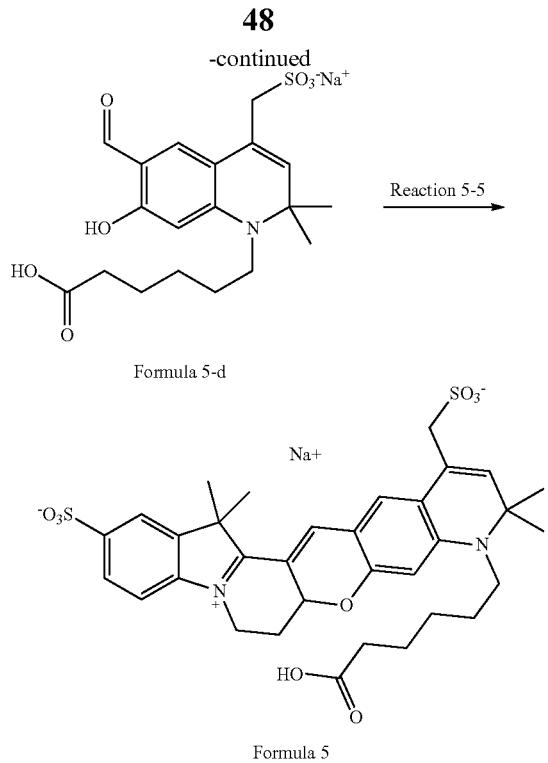

The compound represented by Formula 5-1 was synthesized by Reaction 5-1.

As in Reaction 4-3, the compound represented by Formula 5-1 (15.0 g, 52.6%) was synthesized using 7-methoxy-2,2-4-trimethyl-1,2-dihydroquinoline.

LC-MS: m/z=318.20[M+]

(2) Synthesis of the Compound Represented by Formula 5-b

The compound represented by Formula 5-b was synthesized by Reaction 5-2.

As in Reaction 5-1, the compound represented by Formula 5-b (13.0 g, 65.0%) was synthesized using the compound represented by Formula 5-a, which was synthesized by Reaction 5-1.

LC-MS: m/z=420.14[M+]

(3) Synthesis of the Compound Represented by Formula 5-c

The compound represented by Formula 5-c was synthesized by Reaction 5-3.

As in Reaction 3-7, the compound represented by Formula 5-c (7.2 g, 56.0%) was synthesized using the compound represented by Formula 5-b, which was synthesized by Reaction 5-2.

LC-MS: m/z=406.12[M+]

(4) Synthesis of the Compound Represented by Formula 5-d

The compound represented by Formula 5-d was synthesized by Reaction 5-4.

As in Reaction 3-8, the compound represented by Formula 5-d (2.5 g, 30%) was synthesized using the compound represented by Formula 5-c, which was synthesized by Reaction 5-3.

LC-MS: m/z=434.12[M+]

(5) Synthesis of the Compound Represented by Formula 5

The compound represented by Formula 5 was synthesized by Reaction 5-5.

As in Reaction 4-6, the compound represented by Formula 5 (0.51 g, 32.0%) was synthesized using the compound represented by Formula 4-b, which was synthesized by Reaction 4-2, and the compound represented by Formula 5-d, which was synthesized by Reaction 5-4.

LC-MS: m/z=693.18[M+]

Synthesis Example 6: Synthesis of the Compound Represented by Formula 6

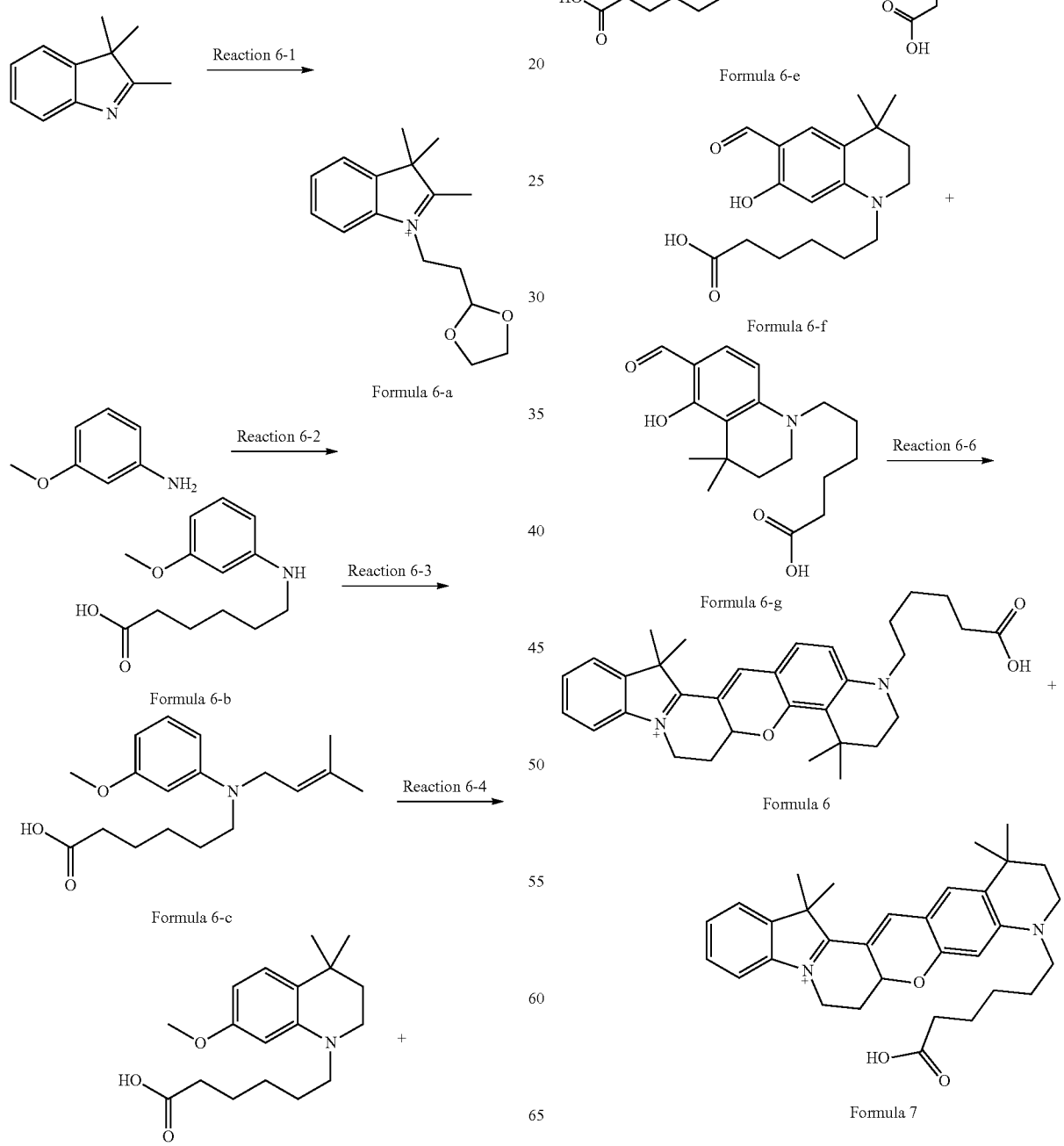

(1) Synthesis of the Compound Represented by Formula 6-a

The compound represented by Formula 6-a was synthesized by Reaction 6-1.

As in Reaction 1-3, the compound represented by Formula 6-a (10.0 g, 62.5%) was synthesized using 2,3,3-triethylindolenine.

LC-MS: m/z=261.16[M+]

(2) Synthesis of the Compound Represented by Formula 6-b

The compound represented by Formula 6-b was synthesized by Reaction 6-2.

As in Reaction 4-3, the compound represented by Formula 6-b (8.1 g, 42.1%) was synthesized using m-anisidine.

LC-MS: m/z=238.14[M+]

(3) Synthesis of the Compound Represented by Formula 6-c

The compound represented by Formula 6-c was synthesized by Reaction 6-3.

The compound represented by Formula 6-b (5.0 g, 21.0 mmol), which was synthesized by Reaction 6-2, 1-chloro-3-methyl-2-butane (5.2 g, 25.3 mmol), potassium carbonate (3.5 g, 25.3 mol), and 5 mL of acetonitrile were stirred under reflux. After completion of the reaction, the reaction solution was purified by column chromatography (4.0 g, 62.0%).

LC-MS: m/z=306.20[M+]

(4) Synthesis of the Compound Represented by Formula 6-d

The compound represented by Formula 6-d was synthesized by Reaction 6-4.

The compound represented by Formula 6-c (4.0 g, 13.1 mmol), which was synthesized by Reaction 6-3, and 4.0 ml of methanesulfonic acid were stirred under reflux. After completion of the reaction, the reaction solution was neutralized, extracted, and purified by column chromatography (3.0 g, 75.2%).

LC-MS: m/z=306.20[M+]

(5) Synthesis of the Compound Represented by Formula 6-e

The compound represented by Formula 6-e was synthesized by Reaction 6-4.

As in Reaction 3-7, the compound represented by Formula 6-e (2.5 g, 87.3%) was synthesized using the compound represented by Formula 6-3, which was synthesized by Reaction 6-4.

LC-MS: m/z=292.18[M+]

(6) Synthesis of the Compound Represented by Formula 6-f

The compounds represented by Formulae 6-f and 6-g were synthesized by Reaction 6-5.

As in Reaction 3-8, the compounds represented by Formulae 6-f (0.84 g, 31.8%) and 6-g (0.56 g, 21.2%) were synthesized using the compound synthesized by Reaction 6-4.

LC-MS: m/z=320.4[M+]

(7) Synthesis of the Compound Represented by Formula 6

The compound represented by Formula 6 was synthesized by Reaction 6-6.

As in Reaction 1-7, the compound represented by Formula 6 (0.35 g, 32.0%) was synthesized using the compound represented by Formula 6-a, which was synthesized by Reaction 6-1, and the compound represented by Formula 6-f, which was synthesized by Reaction 6-5.

LC-MS: m/z=500.30[M+]

Synthesis Example 7: Synthesis of the Compound Represented by Formula 7

(1) Synthesis of the Compound Represented by Formula 7

The compound represented by Formula 7 was synthesized by Reaction 6-6.

As in Reaction 1-7, the compound represented by Formula 7 (0.24 g, 35.0%) was synthesized using the compound represented by Formula 6-a, which was synthesized by Reaction 6-1, and the compound represented by Formula 6-g, which was synthesized by Reaction 6-5.

LC-MS: m/z=500.30[M+]

Synthesis Example 8: Synthesis of the Compound Represented by Formula 44

(1) Synthesis of the Compound Represented by Formula 8-a

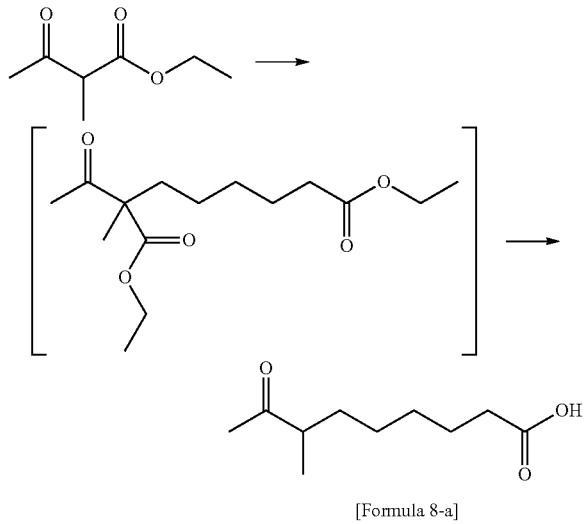

[Reaction 8-1]

[Formula 8-a]

The compound represented by Formula 8-a was synthesized by Reaction 8-1.

Ethyl 2-methylacetatoacetate (23.5 g, 163 mmol) and ethyl 6-bromohexanoate (40.0 g, 179 mmol) were stirred in 200 ml of ethanol and liquid sodium ethoxide was added dropwise thereto. The mixture was stirred at 80° C. for 10 h. After completion of the reaction, the solid was filtered off.

The filtrate was distilled under reduced pressure and extracted with dichloromethane and a 2 N aqueous solution of hydrochloric acid. The organic layer was treated with anhydrous sodium sulfate and distilled under reduced pressure (47.7 g). After removal of the solvent, 300 ml of water was added, followed by stirring under reflux for 10 h. After completion of the reaction, the reaction solution was extracted with dichloromethane, treated with sodium sulfate, and distilled under reduced pressure (25 g, 71%).

$^1$H NMR (400 MHz, CDCl$_3$): δ=10.85 (1H, s), 2.52 (1H, m), 2.36 (2H, m) 2.30 (3H, s), 1.65 (4H, m), 1.35 (4H, m), 1.09 (3H, d)

(2) Synthesis of the Compound Represented by Formula 8-b

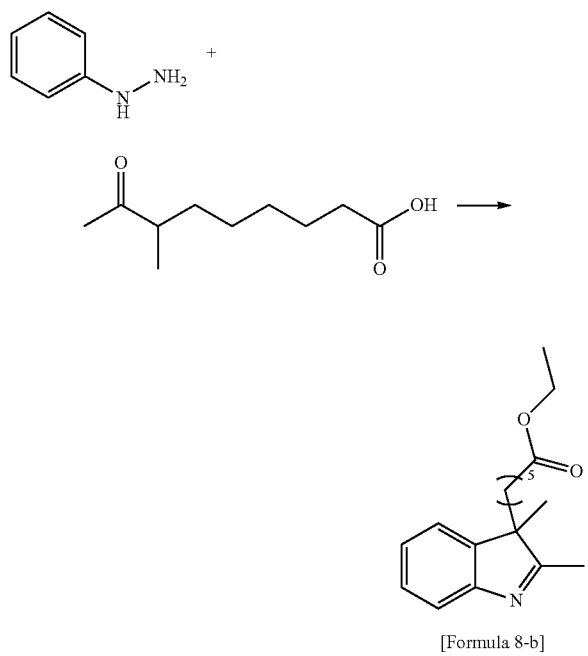

[Formula 8-b]

The compound represented by Formula 8-b was synthesized by Reaction 8-2.

Phenylhydrazine hydrochloride (8.6 g, 75 mmol) and the compound represented by Formula 8-a (42 g, 225 mmol) were added to 86 ml of ethanol and 21.5 ml of hydrochloric acid was added thereto. The mixture was stirred under reflux for 12 h. The reaction mixture was cooled to room temperature and 50 ml of ethyl acetate was added thereto. The resulting solid was filtered, washed with ethyl acetate, and dried under reduced pressure. The residue was extracted with dichloromethane and a 2 N aqueous solution of sodium hydroxide. The organic layer was dried under reduced pressure and purified by silica gel column chromatography (8.5 g, 40%).

$^1$H NMR (400 MHz, CDCl$_3$): δ=7.92 (1H, q), 7.51 (2H, m), 7.42 (1H, q), 4.09 (2H, q), 2.82 (3H, s), 2.18 (2H, t), 2.12 (2H, m), 1.97 (2H, m), 1.49 (3H, s), 1.46 (2H, m), 1.26 (2H, m), 1.23 (3H, t), 0.73 (2H, m).

(3) Synthesis of the Compound Represented by Formula 8-c

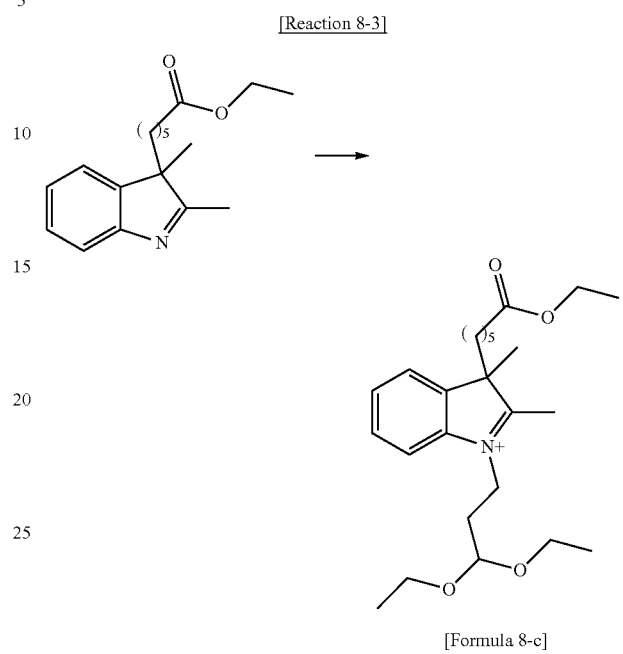

[Formula 8-c]

The compound represented by Formula 8-c was synthesized by Reaction 8-3.

8 g (28 mmol) of the compound represented by Formula 8-b, which was synthesized by Reaction 8-2, was stirred in 400 ml of ethanol in a reactor at room temperature under a stream of nitrogen and a 48% aqueous solution of hydrochloric acid (80 ml) was added dropwise thereto. After 1 h, the reaction solution was distilled under reduced pressure. Acetonitrile (320 ml), acetic acid (8 ml), and acrolein diethyl acetal (65.72 g, 505 mmol) were added to the reactor. The mixture was allowed to react at 70° C. for 2 h. The reaction solution was distilled under reduced pressure and purified by HPLC (Rainin Dynamax C18, 8 μm column) using water/acetonitrile (0.1% trifluoroacetic acid) as the developing solution at a rate of 20 mL/min to 10-100% for 60 min.

(4) Synthesis of the Compound Represented by Formula 8-d

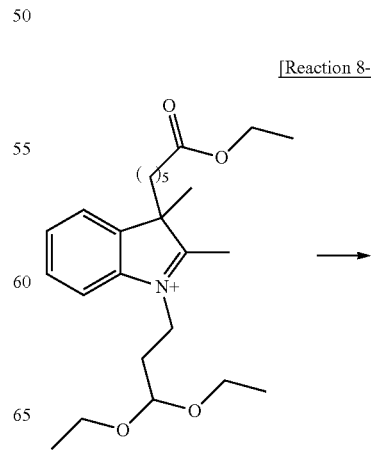

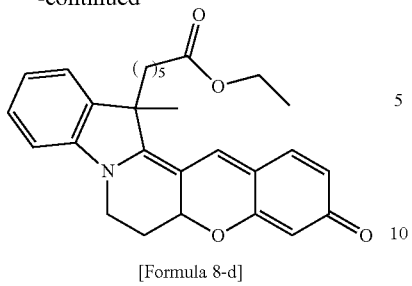

[Formula 8-d]

The compound represented by Formula 8-d was synthesized by Reaction 8-4.

2 g (4.7 mmol) of the compound represented by Formula 8-c, which was synthesized by Reaction 8-3, and 0.58 g (4.7 mmol) of 2,4-dihydroxybenzaldehyde were stirred under reflux in 20 ml of ethanol for 3 h. The reaction solution was cooled to room temperature, distilled under reduced pressure, and purified by silica gel column chromatography. To the crude product were added 10 ml of chloroform and 1 ml of a 50% aqueous solution of sulfuric acid. The mixture was stirred at room temperature for 20 min. The reaction mixture was adjusted to pH 7-8 with a 2 N solution of sodium hydroxide, extracted with methylene chloride, and purified by silica gel column chromatography (0.3 g, 15%).

(5) Synthesis of the Compound Represented by Formula 44

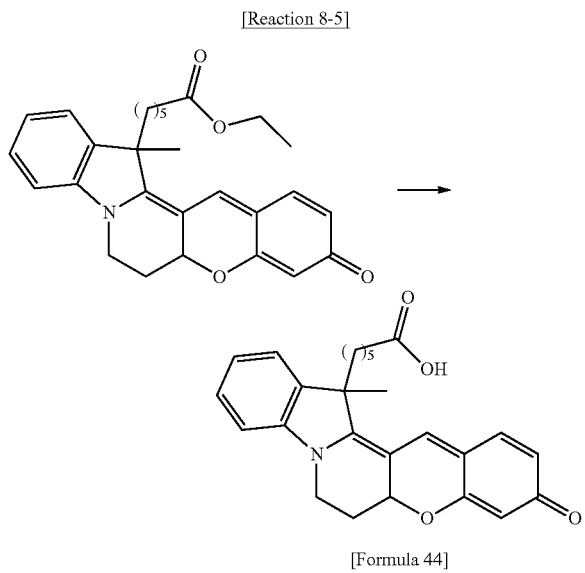

[Formula 44]

The compound represented by Formula 44 was synthesized by Reaction 8-5.

0.3 g (0.67 mmol) of the compound represented by Formula 8-d, which was synthesized by Reaction 8-4, was added to 1.3 ml of acetonitrile and 1.3 ml of a 6 N hydrochloric acid solution was added thereto. The mixture was stirred for 12 h. The reaction solution was adjusted to pH 7-8 with a 2 N sodium hydroxide solution, distilled under reduced pressure, and purified by HPLC (Rainin Dynamax C18, 8 μm column) using water/acetonitrile (0.1% trifluoroacetic acid) as the developing solution (90 mg, 32%).

$^1$H NMR (400 MHz, MeOD): δ=8.28 (1H, s), 7.68 (2H, m), 7.61 (2H, m), 7.48 (1H, d), 6.58 (1H, d), 6.40 (1H, s), 5.42 (1H, m), 6.70 (1H, m), 4.30 (1H, m), 2.87 (1H, m), 2.54 (1H, m), 2.14 (2H, m), 1.80 (2H, m), 1.29 (3H, s), 0-3 (6H, m)

Synthesis Example 9: Synthesis of the Compound Represented by Formula 45

(1) Synthesis of the Compound Represented by Formula 9-a

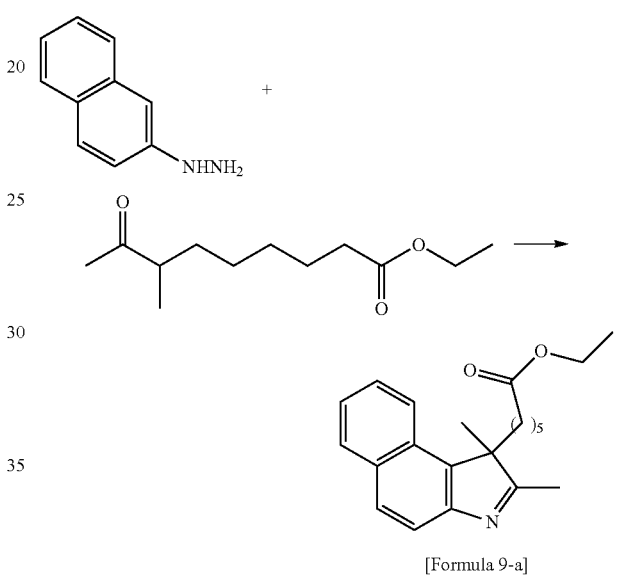

[Formula 9-a]

In a similar manner to Reaction 8-2, the compound represented by Formula 9-a was synthesized by Reaction 9-1.

$^1$H NMR (400 MHz, CDCl$_3$): δ=7.92 (2H, dd), 7.81 (1H, d), 7.76 (1H, d), 7.49 (1H, t), 7.39 (1H, t), 4.01 (2H, q), 2.38 (1H, m) 2.32 (3H, s), 2.04 (2H, t), 1.97 (1H, m), 1.47 (3H, s), 1.35 (2H, m), 1.16 (3H, t), 1.07 (2H, m), 0.58 (1H, m), 0.39 (1H, m)

(2) Synthesis of the Compound Represented by Formula 9-b

[Reaction 9-2]

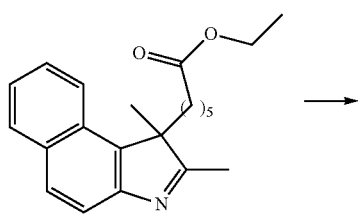

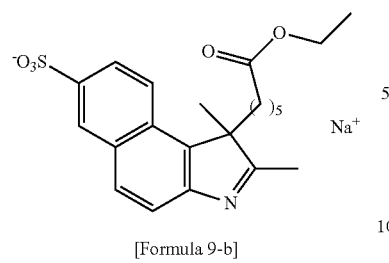

[Formula 9-b]

The compound represented by Formula 9-b was synthesized by Reaction 9-2.

10 g (30 mmol) of the compound represented by Formula 9-a, which was synthesized by Reaction 9-1, was stirred in 5 ml of a sulfuric acid solution at 180° C. for 2 h. After cooling to room temperature, the reaction solution was poured into ice and 5 ml of a 50% sodium hydroxide solution was slowly added dropwise thereto. After stirring at room temperature for 24 h, the resulting precipitate was filtered off and 5 ml of a saturated aqueous solution of sodium sulfate was added to the filtrate. The resulting precipitate was filtered and recrystallized twice from water. The resulting solid was dried under vacuum (8 g, 60%).

(3) Synthesis of the Compound Represented by Formula 9-c

[Reaction 9-3]

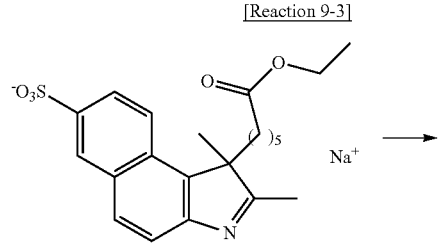

[Formula 9-c]

In a similar manner to Reaction 8-3, the compound represented by Formula 9-c was synthesized by Reaction 9-3.

(4) Synthesis of the Compound Represented by Formula 9-d

[Reaction 9-4]

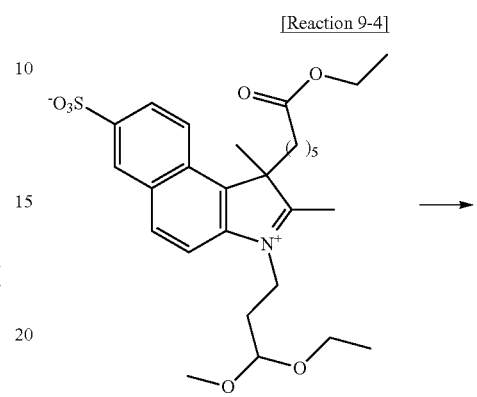

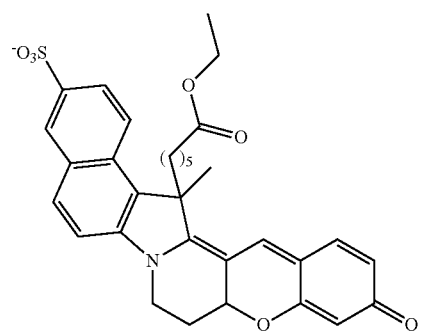

[Formula 9-d]

In a similar manner to Reaction 8-4, the compound represented by Formula 9-d was synthesized by Reaction 9-4.

(5) Synthesis of the Compound Represented by Formula 45

[Reaction 9-5]

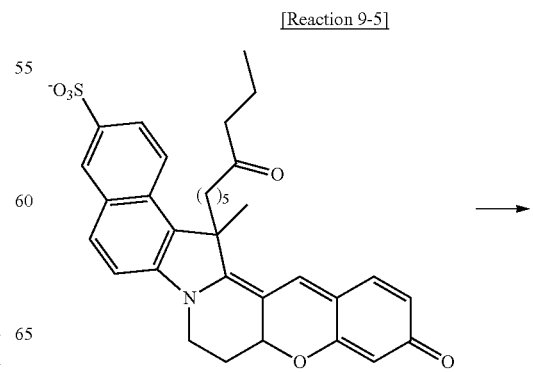

-continued

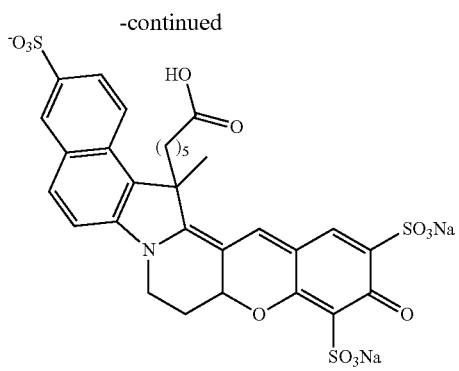

[Formula 45]

The compound represented by Formula 45 was synthesized by Reaction 9-5.

0.3 g (30 mmol) of the compound represented by Formula 9-d, which was synthesized by Reaction 9-4, was stirred in 1 ml of a solution of sulfuric acid at 40° C. for 2 h. The reaction solution was cooled to room temperature and poured into ice. To the reaction solution was slowly added dropwise a 50% sodium hydroxide solution until neutrality. The mixture was purified by HPLC (Rainin Dynamax C18, 8 μm column) using water/acetonitrile (0.1% trifluoroacetic acid) as the developing solution at a rate of 20 mL/min to 10-100% for 60 min.

$^1$H NMR (400 MHz, MeOD): δ=8.13 (2H, m), 7.97 (3 h, m), 7.72 (2H, m), 5.48 (1H, m), 4.65 (1H, m) 4.43 (1H, m), 2.98 (1H, m), 2.61 (1H, m), 2.44 (1H, m), 2.24 (1H, m), 1.77 (3H, d), 1.70 (2H, m), 0.85 (4H, m) 0.46 (1H, m), −0.01 (1H, m)

Synthesis Example 10: Synthesis of the Compound Represented by Formula 46

The compound represented by Formula 46 was synthesized by the following reaction:

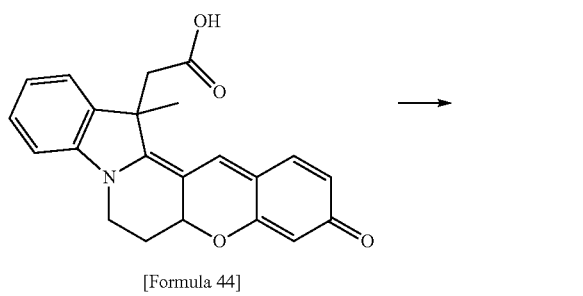

[Formula 46]

The compound represented by Formula 44 (0.5 g, 0.138 mmol), which was synthesized by Reaction 8-5, N-hydroxysuccinimide (0.08 g, 0.069 mmol), and N,N-dicyclohexylcarbodiimide (0.142 g, 0.069 mmol) were dissolved in N,N-dimethylformamide (1 ml). The solution was stirred at room temperature for 1 h. After completion of the reaction, the reaction solution was purified by HPLC (Rainin Dynamax C18, 8 μm column) using water/acetonitrile (0.1% trifluoroacetic acid) as the developing solution at a rate of 20 mL/min to 10-100% for 60 min (0.38 g, 60.0%).

Synthesis Example 11: Synthesis of the Compound Represented by Formula 47

(1) Synthesis of the Compound Represented by Formula 11-a

[Reaction 11-1]

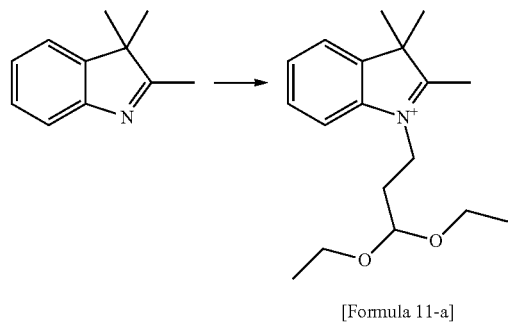

[Formula 11-a]

In a similar manner to Reaction 8-3, the compound represented by Formula 11-a was synthesized by Reaction 11-1.

(2) Synthesis of the Compound Represented by Formula 11-b

[Reaction 11-2]

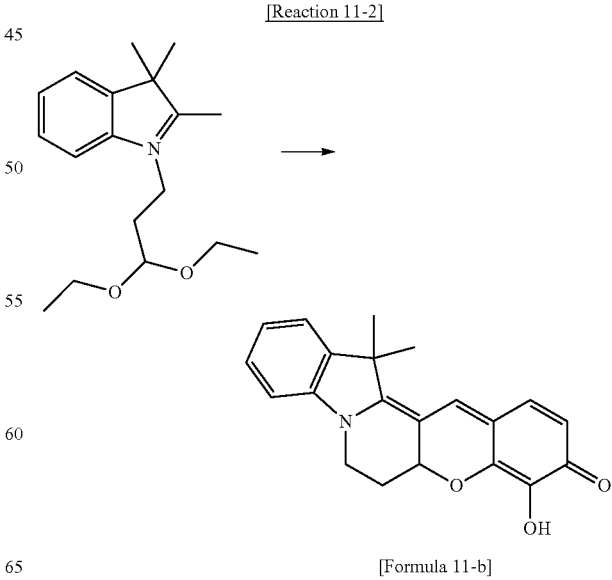

[Formula 11-b]

In a similar manner to Reaction 8-4, the compound represented by Formula 11-b was synthesized by Reaction 11-2.

$^1$H NMR (400 MHz, MeOD): δ=7.90 (1H, s), 7.45 (2H, m), 7.25 (2H, m), 7.00 (1H, d), 6.31 (1H, d), 5.15 (1H, m), 4.36 (1H, m), 3.92 (1H, m), 2.78 (1H, m), 2.41 (1H, m), 1.73 (6H, d)

(3) Synthesis of the Compound Represented by Formula 47

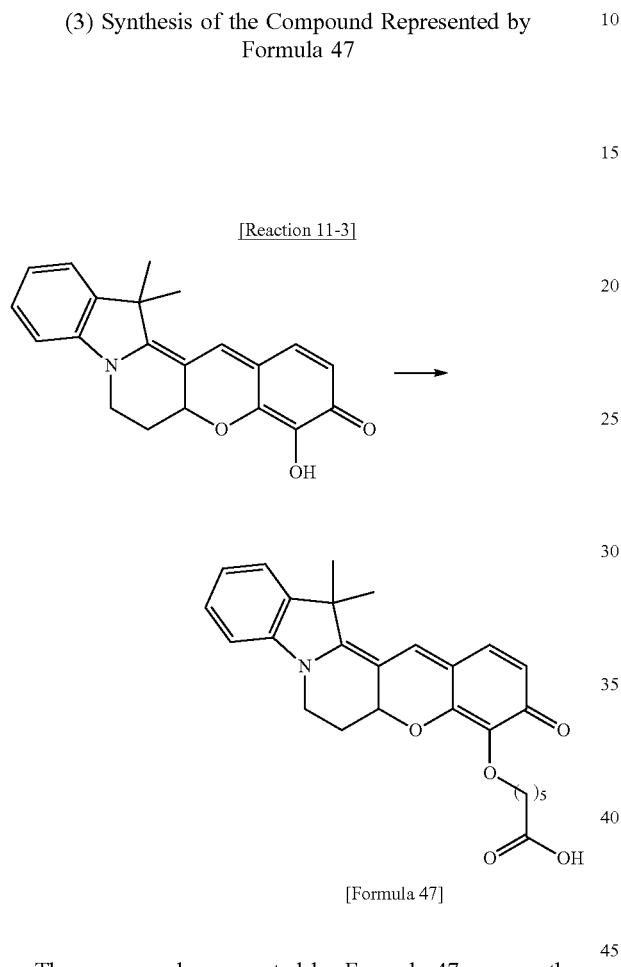

[Formula 47]

The compound represented by Formula 47 was synthesized by Reaction 11-3.

0.3 g (1 mmole) of the compound represented by Formula 11-b, which was synthesized by Reaction 11-2 and 0.1 g (2 mmole) of potassium hydroxide were stirred in 3 ml of ethanol at 50° C. under a stream of nitrogen for 30 min. To the reaction mixture was added 0.3 g (1 mmole) of ethyl 5-iodopentanoate. The resulting mixture was stirred under reflux for 3 h. After completion of the reaction, the reaction solution was concentrated under reduced pressure and purified by HPLC (Rainin Dynamax C18, 8 μm column) using water/acetonitrile (0.1% trifluoroacetic acid) as the developing solution at a rate of 20 mL/min to 10-100% for 60 min.

M+=448.2, $^1$HNMR (400 MHz, D$_2$O): δ=8.28 (1H, s), 7.55-7.80 (4H, m), 7.31 (1H, s), 6.60 (1H, s), 5.51 (1H, s), 4.74 (1H, m), 4.08 (1H, m), 2.94 (1H, m), 2.66 (1H, m), 1.82 (6H, d), 1-4.5 (10H, m)

Synthesis Example 12: Synthesis of the Compound Represented by Formula 48

(1) Synthesis of the Compound Represented by Formula 12-a

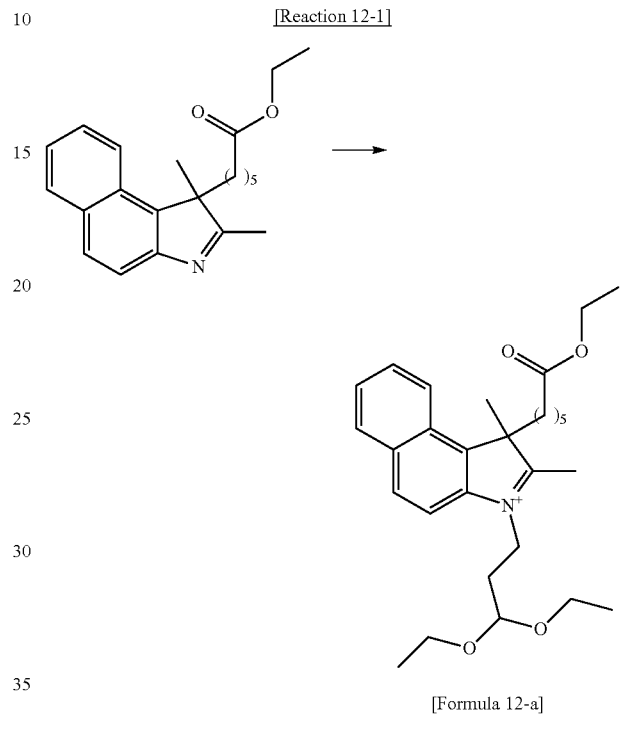

[Formula 12-a]

In a similar manner to Reaction 8-3, the compound represented by Formula 12-a was synthesized by Reaction 12-1.

(2) Synthesis of the Compound Represented by Formula 48

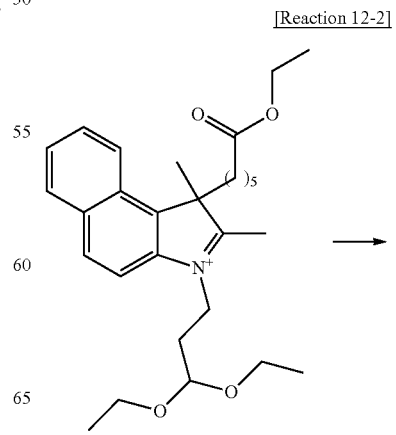

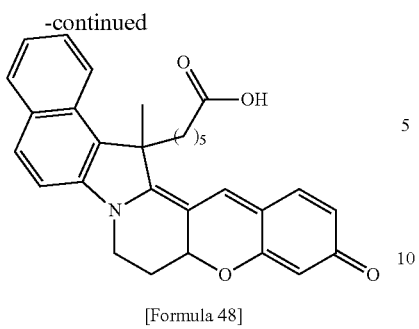

[Formula 48]

In a similar manner to Reaction 8-4, the compound represented by Formula 48 was synthesized by Reaction 12-2.

$^1$H NMR (400 MHz, MeOD): δ=7.40 (1H, s), 8.37 (1H, d), 8.20 (1H, d), 8.13 (1H, d), 7.84 (1H, d), 7.77 (1H, t), 7.67 (1H, t), 7.49 (1H, dd), 6.59 (1H, dt), 6.41 (1H,$), 5.46 (1H, m), 4.82 (1H, m), 4.42 (1H, m), 2.92 (1H, m), 2.60 (1H, m), 2.10 (2H, m), 2.01 (2H, t), 1.29 (3H, s), 1.33 (2H, m), 1.11 (2H, m), 0.84 (1H, m), 0.43 (1H, m)

Synthesis Example 13: Synthesis of the Compound Represented by Formula 49

(1) Synthesis of the Compound Represented by Formula 49

[Reaction 13-1]

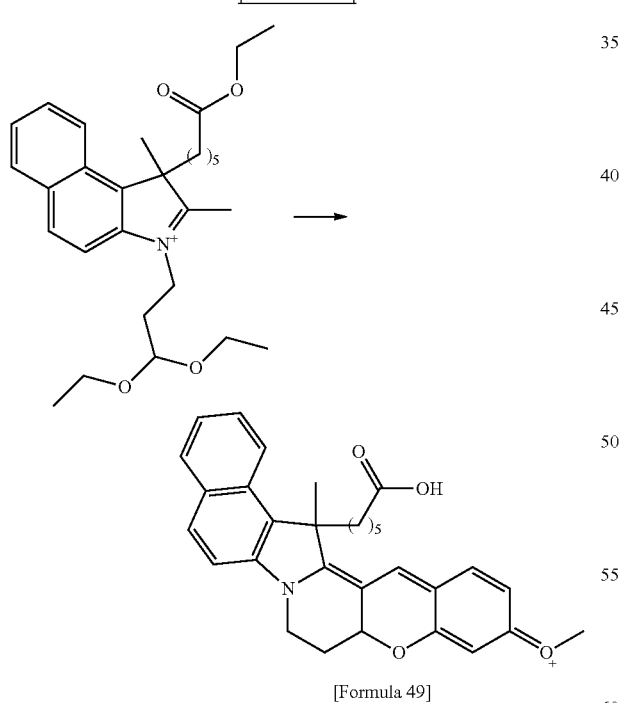

[Formula 49]

In a similar manner to Reaction 8-4, the compound represented by Formula 49 was synthesized by Reaction 13-1.

$^1$H NMR (400 MHz, MeOD): δ=8.39 (1H, s), 8.33 (1H, d), 8.17 (1H, dd), 8.09 (1H, d), 7.83 (1H, dd), 7.74 (1H, t), 7.64 (1H, t), 7.54 (1H, dd), 6.70 (1H, dt), 6.56 (1H, m), 5.46 (1H, m), 4.84 (1H, m), 4.41 (1H, m), 3.86 (3H, s), 3.70 (1H, m), 2.90 (2H, m), 2.63 (3H, m), 1.94 (2H, t), 1.25 (3H, s), 1.07 (2H, t), 0.80 (1H, m), 0.40 (1H, m)

Synthesis Example 14: Synthesis of the Compound Represented by Formula 50

(1) Synthesis of the Compound Represented by Formula 50

[Reaction 14-1]

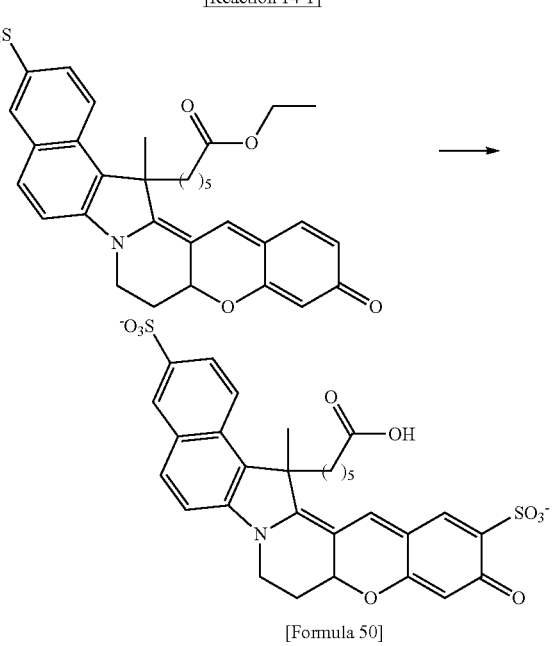

[Formula 50]

In a similar manner to Reaction 9-5, the compound represented by Formula 50 was synthesized by Reaction 14-1.

$^1$H NMR (400 MHz, DMSO): δ=8.62 (1H, s), 8.40 (1H, m), 8.31 (1H, m), 8.37 (1H, d), 7.99 (1H, dd), 7.92 (1H, d), 8.05 (1H, s), 6.43 (1H, s), 5.48 (1H, m), 4.84 (1H, m), 4.42 (1H, m), 2.80 (5H, m), 2.58 (1H, m), 1.98 (3H, s), 1.95 (2H, t), 1.20 (1H, m), 1.04 (1H, m), 0.76 (1H, m), 0.25 (1H, m)

Synthesis Example 15: Synthesis of the Compound Represented by Formula 51

(1) Synthesis of the Compound Represented by Formula 15-a

[Reaction 15-1]

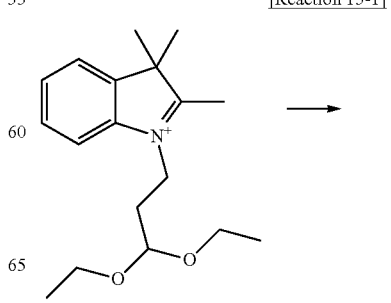

-continued

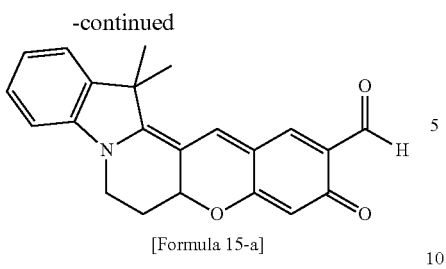

[Formula 15-a]

In a similar manner to Reaction 8-4, the compound represented by Formula 50-a was synthesized by Reaction 15-1.

$^1$H NMR (400 MHz, CDCl$_3$): δ=10.15 (1H, s), 7.80 (1H, s), 7.66 (1H, s), 7.36 (2H, m), 7.28 (1H, d), 7.12 (1H, d), 5.97 (1H, s), 5.12 (1H, m), 4.25 (1H, m), 3.93 (1H, m), 2.73 (1H, m), 2.33 (1H, m), 1.68 (3H, s), 1.63 (3H, s)

(2) Synthesis of the Compound Represented by Formula 15-b

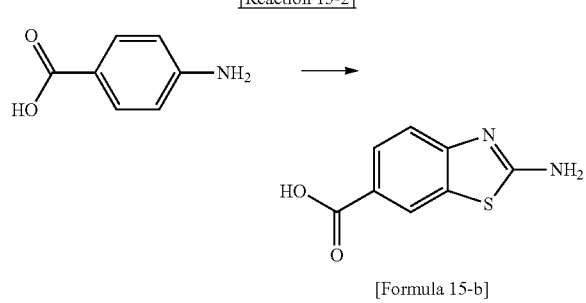

[Formula 15-b]

The compound represented by Formula 15-b was synthesized by Reaction 15-2.

5 g (36 mmole) of 4-aminobenzoic acid and 19.03 g (195 mmole) of potassium thiocyanate were stirred in 70 ml of acetic acid at room temperature for 50 min. To the mixture was slowly added dropwise 2.06 ml (40 mmole) of bromine at 0° C. The resulting mixture was stirred at room temperature for 24 h. The reaction solution was stirred in 200 ml of water at 70-80° C. for 1.5 h. The reaction mixture was filtered under reduced pressure. The filtrate was adjusted to pH 6 by the addition of an ammonium solution at 0° C. and filtered under reduced pressure. The filtered solid was dried.

(3) Synthesis of the Compound Represented by Formula 15-c

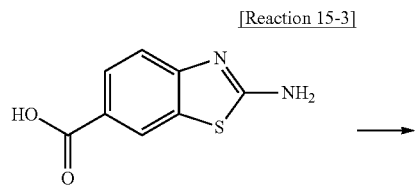

-continued

[Formula 15-c]

The compound represented by Formula 15-c was synthesized by Reaction 15-3.

20 g of potassium hydroxide was stirred in 60 ml of water at room temperature for 30 min. To the reaction mixture was added 9.4 g of the compound represented by Formula 15-b, which was synthesized by Reaction 15-2. The resulting mixture was stirred under reflux at 120° C. in the dark for 24 h. The reaction mixture was adjusted to pH 4 by the addition of hydrochloric acid and filtered. The resulting solid was washed several times with water and dried.

(4) Synthesis of the Compound Represented by Formula 51

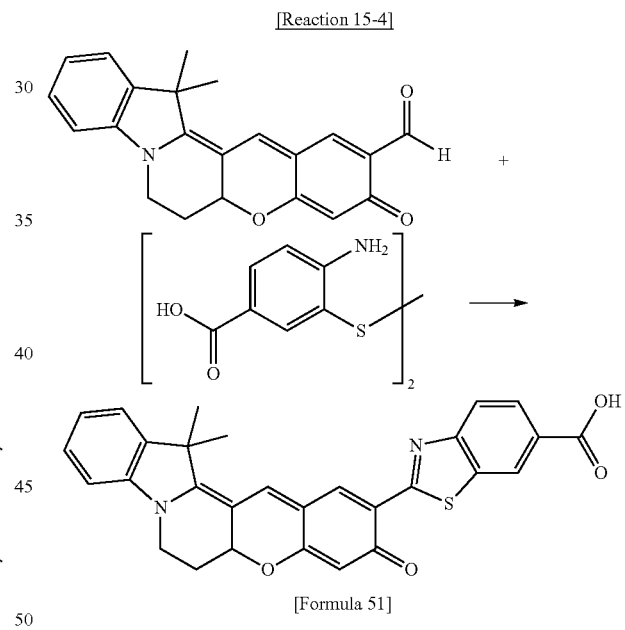

[Formula 51]

The compound represented by Formula 51 was synthesized by Reaction 15-4.

0.2 g (0.58 mmole) of the compound represented by Formula 15-a, which was synthesized by Reaction 15-1, 0.69 g (0.69 mmole) of the compound represented by Formula 15-c, which was synthesized by Reaction 15-3, and 0.011 g (0.058 mmole) of p-toluenesulfonic acid were stirred in dimethylformamide at 80-90° C. for 24 h. After the reaction was finished, water was added. The resulting mixture was filtered under reduced pressure, washed several times with water, and dried.

$^1$H NMR (400 MHz, DMSO): δ=12.85 (1H, s), 8.78 (1H, s), 8.74 (1H, s), 8.04 (1H, s), 7.80 (1H, q), 7.57 (1H, m), 7.44 (1H, d), 7.08 (1H, d), 6.59 (1H, s), 5.44 (1H, q), 4.68 (1H, q), 4.23 (1H, m), 2.78 (1H, m), 2.26 (1H, m), 1.78 (6H, d).

Synthesis Example 16: Synthesis of the Compound Represented by Formula 52

(1) Synthesis of the Compound Represented by Formula 16-a

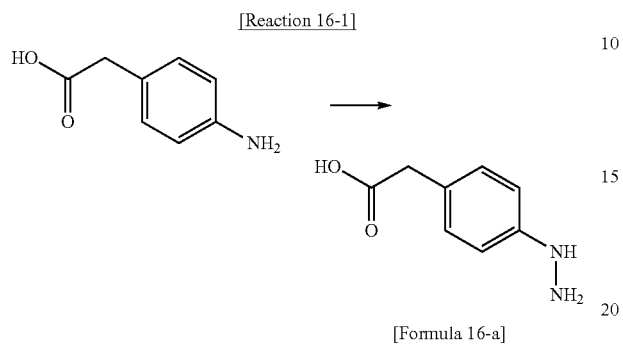

[Formula 16-a]

The compound represented by Formula 16-a was synthesized by Reaction 16-1.

15.1 g (0.1 mole) of 4-aminophenylacetic acid and 10.5 g (0.1 mol) of sodium carbonate were stirred in 120 ml of water for 10 min. To the reaction solution was slowly added dropwise a solution of 6.9 g (0.1 mole) of sodium nitrile in 30 ml of water. Heat was released and bubbles were formed. After stirring for 10 min, 140 ml of hydrochloric acid was slowly added dropwise. The mixture was stirred for 30 min. A solution of 45.1 g (0.2 mole) of tin chloride dihydrate in hydrochloric acid was slowly added dropwise, followed by stirring at room temperature. After the reaction was finished, the reaction mixture was filtered under reduced pressure and washed with cold water and ethanol (22 g).

(2) Synthesis of the Compound Represented by Formula 16-b

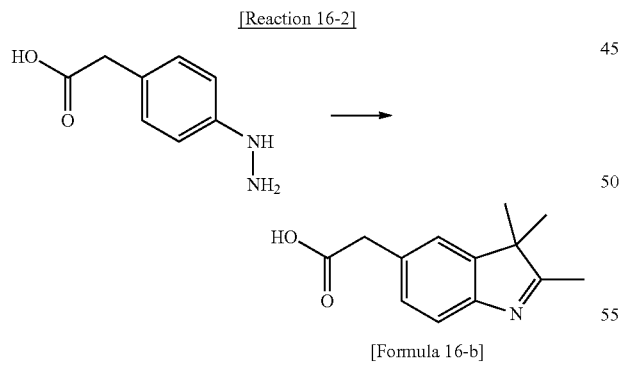

[Formula 16-b]

The compound represented by Formula 16-b was synthesized by Reaction 16-2.

22 g (0.132 mole) of the compound represented by Formula 15-a, which was synthesized by Reaction 15-1, was stirred in 220 ml of acetic acid. To the reaction mixture was added 27.4 g (0.318 mole) of 3-methyl-2-butanone. The resulting mixture was stirred at room temperature for 30 min. Stirring was continued under reflux for complete dissolution. The reaction solution was cooled to room temperature and extracted with methylene chloride and water. The extract was concentrated under reduced pressure and dried to obtain 10 g of a brown solid.

(3) Synthesis of the Compound Represented by Formula 16-c

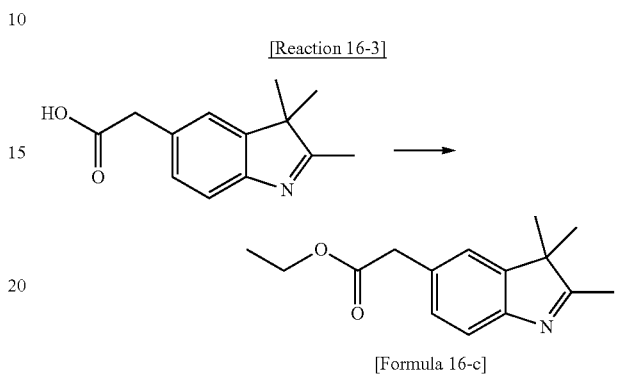

[Formula 16-c]

The compound represented by Formula 16-c was synthesized by Reaction 16-3.

7 ml of thionyl chloride was slowly added dropwise to 100 ml of ethanol cooled to 0° C. The mixture was stirred for 10 min. To the reaction mixture was slowly added dropwise a solution of 10 g (0.05 mole) of the compound represented by Formula 15-a, which was synthesized by Reaction 15-1, in ethanol. The resulting mixture was stirred at room temperature, concentrated under reduced pressure, and dried to obtain 13 g of a violet liquid.

(4) Synthesis of the Compound Represented by Formula 16-d

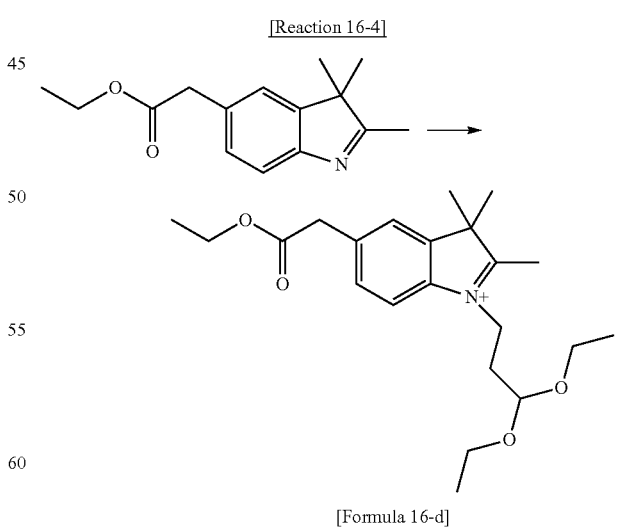

[Formula 16-d]

In a similar manner to Reaction 8-3, the compound represented by Formula 16-d was synthesized by Reaction 16-4.

(4) Synthesis of the Compound Represented by Formula 16-e

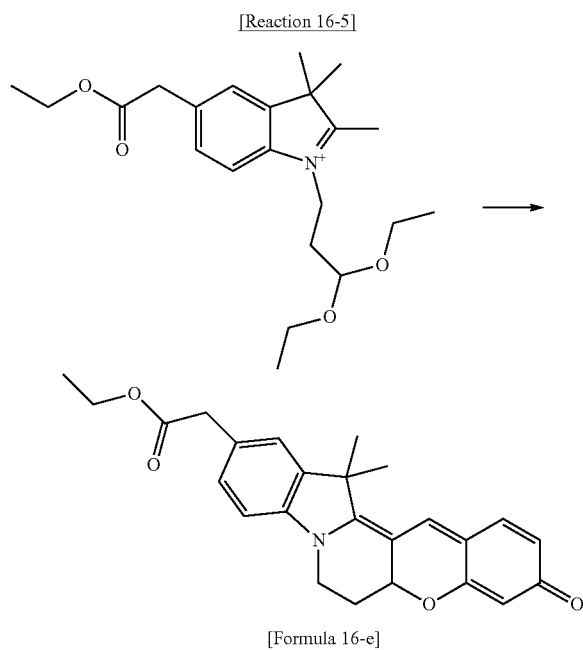

[Formula 16-e]

In a similar manner to Reaction 8-4, the compound represented by Formula 16-e was synthesized by Reaction 16-5.

(5) Synthesis of the Compound Represented by Formula 52

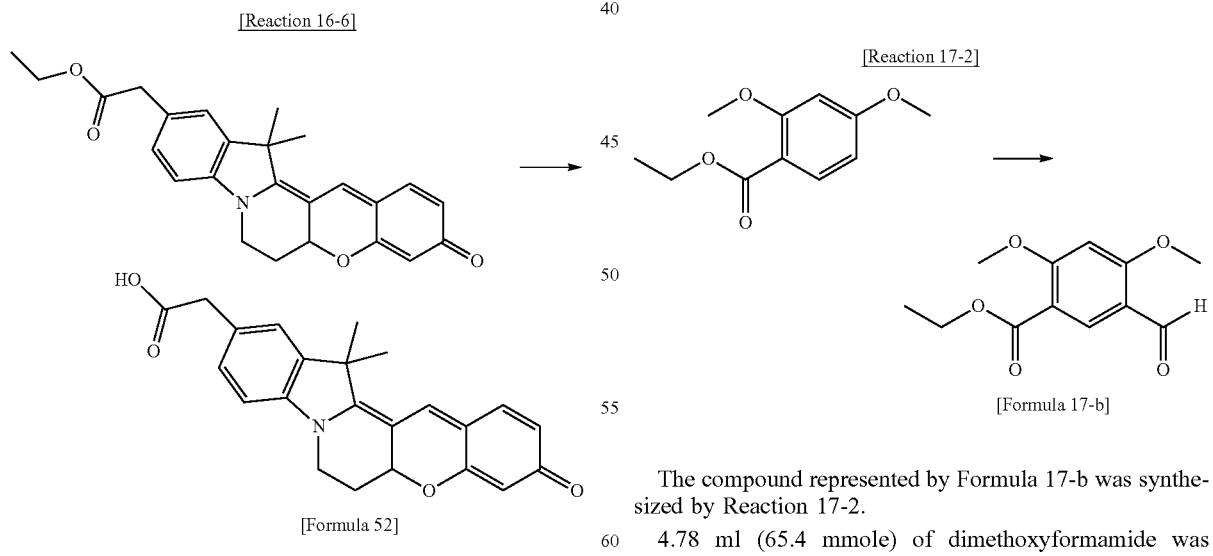

[Formula 52]

The compound represented by Formula 52 was synthesized by Reaction 16-6.

0.6 g (1 mmole) of the compound represented by Formula 16-e, which was synthesized by Reaction 16-5, was stirred in a mixture of methanol, tetrahydrofuran, and water (11 ml each). To the reaction mixture was added 3.8 g (9 mmole) of lithium hydroxide monohydrate. The resulting mixture was stirred for 24 h. The reaction mixture was adjusted to pH 4 with a 1 N aqueous solution of hydrochloric acid and extracted with methylene chloride. The extract was distilled under reduced pressure and purified by silica gel column chromatography (0.5 g).

Synthesis Example 17: Synthesis of the Compound Represented by Formula 53

(1) Synthesis of the Compound Represented by Formula 17-a

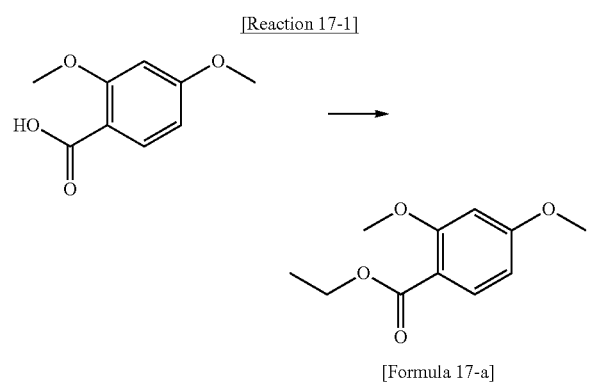

[Formula 17-a]

In a similar manner to Reaction 16-3, the compound represented by Formula 17-a was synthesized by Reaction 17-1.

(2) Synthesis of the Compound Represented by Formula 17-b

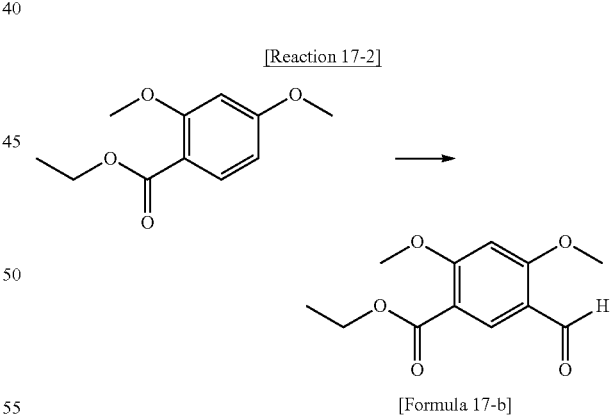

[Formula 17-b]

The compound represented by Formula 17-b was synthesized by Reaction 17-2.

4.78 ml (65.4 mmole) of dimethoxyformamide was slowly added dropwise to 4.01 ml (26 mmole) of phosphoryl chloride. The mixture was stirred for 2 h. To the reaction solution was slowly added dropwise a solution of 5 g (24 mmole) of the compound represented by Formula 17-a, which was synthesized by Reaction 17-1, in 12.5 ml of dimethoxyformamide. The resulting mixture was stirred for 24 h. The reaction solution was slowly added dropwise to excess water. The precipitated solid was filtered under reduced pressure and purified by silica gel column chromatography.

(3) Synthesis of the Compound Represented by Formula 17-c

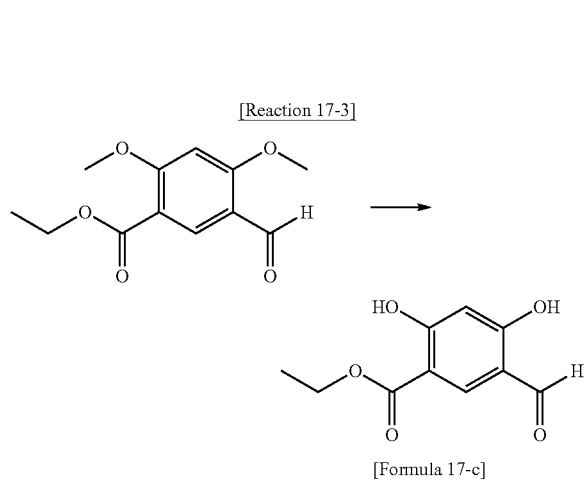

[Formula 17-c]

The compound represented by Formula 17-c was synthesized by Reaction 17-3.

8 g (34 mmole) of the compound represented by Formula 17-b, which was synthesized by Reaction 17-2, was stirred in 200 ml of dichloromethane. To the reaction mixture was slowly added dropwise 13.44 g (101 mmole) of aluminum chloride. The resulting mixture was stirred at 40° C. for 24 h. After cooling to room temperature, the reaction mixture was added dropwise with 100 ml of a 6 N solution of hydrochloric acid, extracted, and purified by silica gel column chromatography (4.3 g, 59%).

(4) Synthesis of the Compound Represented by Formula 17-d

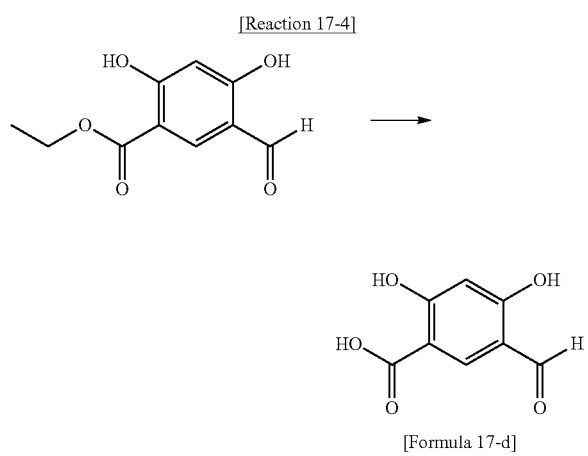

[Formula 17-d]

In a similar manner to Reaction 16-6, the compound represented by Formula 17-d was synthesized by Reaction 17-4.

(5) Synthesis of the Compound Represented by Formula 17-e

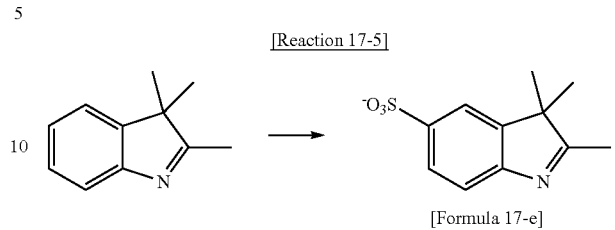

[Formula 17-e]

In a similar manner to Reaction 9-3, the compound represented by Formula 17-e was synthesized by Reaction 17-5.

(6) Synthesis of the Compound Represented by Formula 17-f

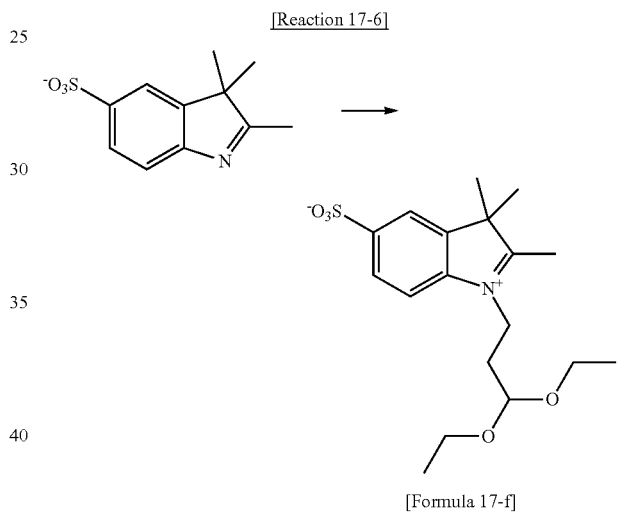

[Formula 17-f]

In a similar manner to Reaction 9-4, the compound represented by Formula 17-f was synthesized by Reaction 17-6.

(7) Synthesis of the Compound Represented by Formula 53

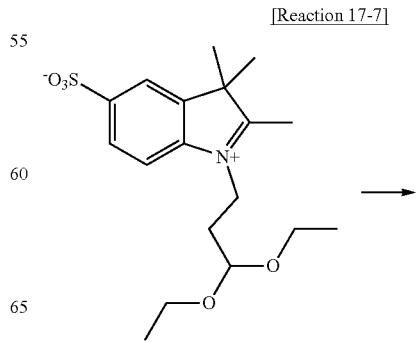

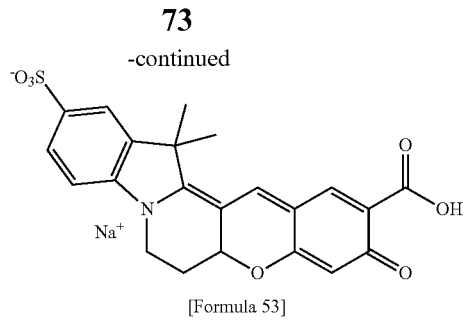

[Formula 53]

In a similar manner to Reaction 8-4, the compound represented by Formula 53 was synthesized by Reaction 17-7.

Synthesis Example 18: Synthesis of the Compound Represented by Formula 97

(1) Synthesis of the Compound Represented by Formula 18-a

[Reaction 18-1]

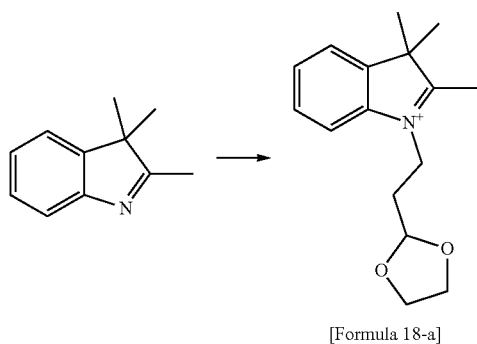

[Formula 18-a]

The compound represented by Formula 18-a was synthesized by Reaction 18-1.

2-(2-Bromoethyl)-1,3-dioxolane (22 mL, 0.188 mol) and potassium iodide (63 g, 0.376 mol) were stirred in 300 ml of acetonitrile at 50° C. for 1 h. To the reaction mixture was added dropwise 2,3,3-triethylindolenine (30 g, 0.188 mol). The resulting mixture was stirred under reflux for 12 h. After cooling, the solid was filtered off. The filtrate was distilled under reduced pressure and purified by silica gel column chromatography (25 g, 34%).

[Reaction 18-2]

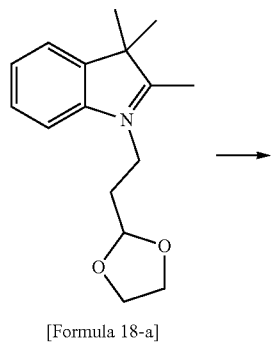

[Formula 18-a]

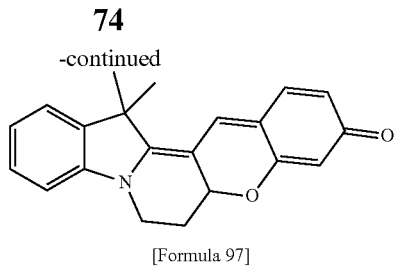

[Formula 97]

(2) The Compound Represented by Formula 97 was Synthesized by Reaction 18-2. The compound represented by Formula 18-a (5 g, 1.3 mmol), which was synthesized by Reaction 18-1, and 2,4-dihydroxybenzaldehyde (1.8 g, 1.3 mmol) were stirred under reflux in 10 ml of ethanol for 3 h. The reaction solution was cooled to room temperature, distilled under reduced pressure, and purified by silica gel column chromatography. To the crude product were added 500 ml of chloroform and 100 ml of a 50% aqueous solution of sulfuric acid. The mixture was stirred at room temperature for 20 min. The reaction mixture was adjusted to pH 7-8 with a 2 N sodium hydroxide solution, extracted with methylene chloride, distilled under reduced pressure, and purified by silica gel column chromatography.

Synthesis Example 19: Synthesis of the Compound Represented by Formula 98

[Reaction 18-3]

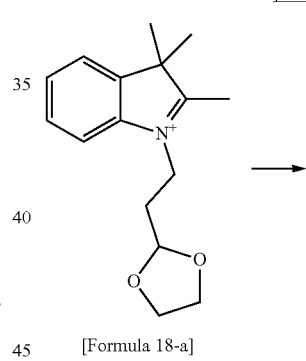

[Formula 18-a]

[Formula 98]

The compound represented by Formula 98 was synthesized by Reaction 18-3.

The compound represented by Formula 18-a (1 g, 4 mmol), which was synthesized by Reaction 18-1, and 4-dimethylaminosalicylaldehyde (0.7 g, 4 mmol) were stirred under reflux in 10 ml of ethanol for 2 h. The reaction solution was cooled to room temperature, distilled under reduced pressure, and purified by silica gel column chromatography. To the crude product were added 100 ml of chloroform and 10 ml of a 50% aqueous solution of sulfuric acid. The mixture was stirred at room temperature for 20 min. The reaction mixture was adjusted to pH 7-8 with a 2 N sodium hydroxide solution, extracted with methylene chloride, distilled under reduced pressure, and purified by silica gel column chromatography.

Synthesis Example 20: Synthesis of the Compound Represented by Formula 105

[Reaction 20-1]

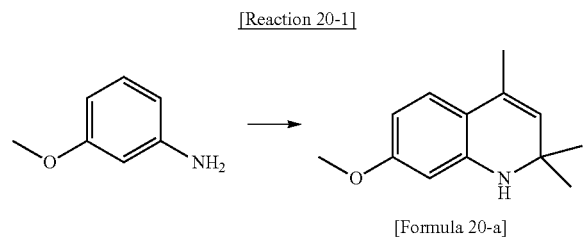

[Formula 20-a]

(1) In accordance with the known synthesis method described in Chem. Eur. J. 2012, 18, 16196-16202, the compound represented by Formula 20-a was synthesized by Reaction 20-1.

[Reaction 20-2]

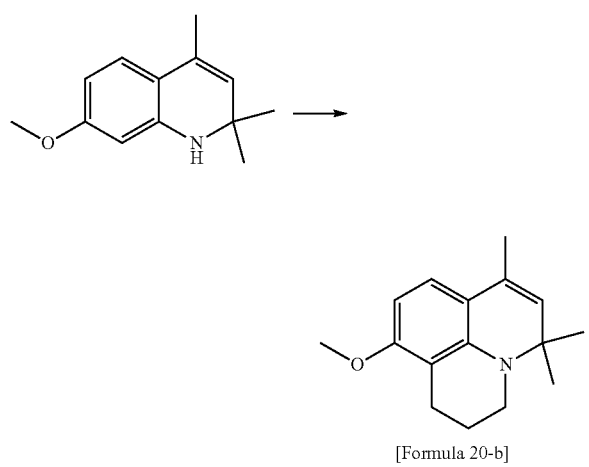

[Formula 20-b]

(2) In accordance with the known synthesis method described in Chem. Eur. J. 2010, 16, 158-166, the compound represented by Formula 20-b was synthesized by Reaction 20-2.

[Reaction 20-3]

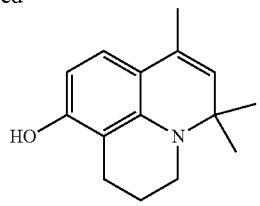

[Formula 20-c]

(3) In accordance with the known synthesis method described in Chem. Eur. J. 2010, 16, 158-166, the compound represented by Formula 20-c was synthesized by Reaction 20-3.

[Reaction 20-4]

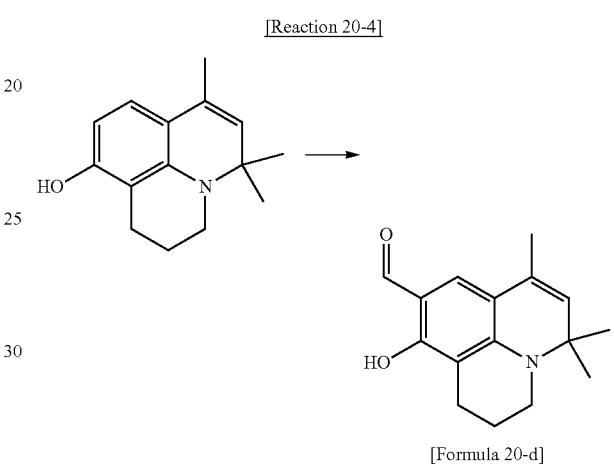

[Formula 20-d]

(4) The compound represented by Formula 20-d was synthesized by Reaction 20-4.

Phosphorus oxychloride was added dropwise to N-dimethylformamide cooled to 0° C. in a reactor. The mixture was stirred for 10 min. To the reaction mixture was added dropwise a dilute solution of the compound represented by Formula 4-c in N-dimethylformamide. The mixture was allowed to react at 50° C. for 12 h. After cooling to room temperature, the reaction mixture was poured into ice-water, neutralized with a 1 M aqueous solution of sodium hydroxide, extracted with ethyl acetate, concentrated under reduced pressure, and purified by silica gel column chromatography.

(5) The compound represented by Formula 105 was synthesized by the following reaction 20-5:

[Reaction 20-5]

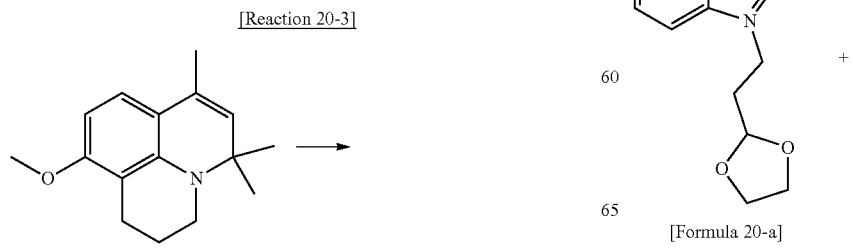

[Formula 20-a]

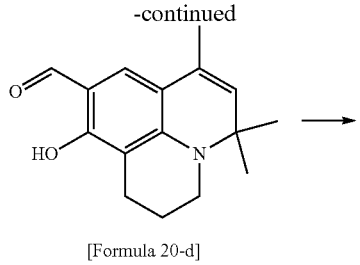

[Formula 20-d]

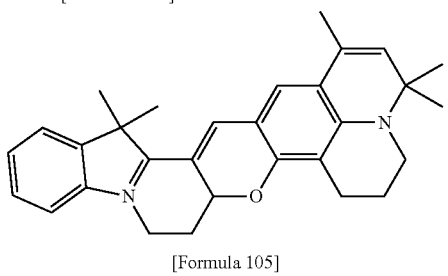

[Formula 105]

The compound represented by Formula 20-a (3 g, 0.0115 mol) was stirred in 30 ml of ethanol in a reactor at 40° C. To the reaction mixture was added a dilute solution of the compound represented by Formula 4-d (2.88 g, 0.0112 mol) in ethanol. The mixture was stirred under reflux for 12 h. The reaction solution was cooled to room temperature and concentrated under reduced pressure. The concentrate was diluted with 300 ml of chloroform and 30 ml of a 50% aqueous solution of sulfuric acid was added dropwise thereto at room temperature. The mixture was allowed to react for 2 h. The reaction mixture was neutralized with a 1 M aqueous solution of sodium hydroxide, extracted with methylene chloride, concentrated under reduced pressure, and purified by column chromatography (0.8 g, 16%).

Experimental Example 1

Absorption spectra ($\lambda_{abs}$), emission spectra ($\lambda_{em}$), molar extinction coefficients ($\varepsilon$), and quantum yields of the compounds of Formulae 1-7 were measured and the results are shown in Table 1.

[Comparative Compound]

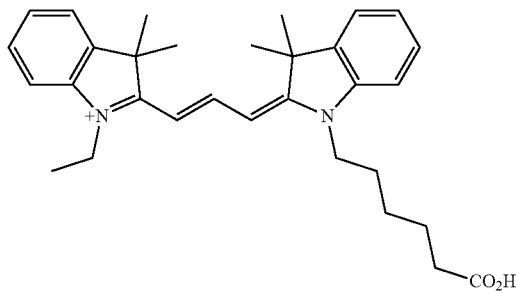 [SMILES: CC[N+]1=C(/C=C/C=C2/N(CCCCCC(=O)O)c3ccccc3C2(C)C)C(C)(C)c2ccccc21]

TABLE 1

| Compound | Solvent | $\lambda_{abs}$ (nm) | $\lambda_{em}$ (nm) | $\varepsilon$ ($M^{-1}cm^{-1}$) | Q.Y. |
| --- | --- | --- | --- | --- | --- |
| Comparative |  | 548 | 562 | 150,000 | 0.04 |
| Formula 1 | DMSO | 584 | 617 | 66,000 | 0.91 |
| Formula 2 | DMSO | 597 | 623 | 71,500 | 0.94 |

TABLE 1-continued

| Compound | Solvent | $\lambda_{abs}$ (nm) | $\lambda_{em}$ (nm) | $\varepsilon$ ($M^{-1}cm^{-1}$) | Q.Y. |
| --- | --- | --- | --- | --- | --- |
| Formula 3 | DMSO | 595 | 624 | 64,000 | 0.87 |
| Formula 4 | DMSO | 584 | 614 | 76,000 | 0.81 |
| Formula 5 | DMSO | 617 | 659 | 65,000 | 0.56 |
| Formula 6 | DMSO | 579 | 612 | 12,800 | 0.72 |
| Formula 7 | DMSO | 584 | 615 | 60,000 | 1.00 |

Experimental Example 2

Goat anti-mouse IgG was labeled with Alexa Fluor® 568 (Thermo Fisher Scientific) and the compound of Formula 1 and their absorption spectra and fluorescence emission spectra were recorded.

Figure 1B:
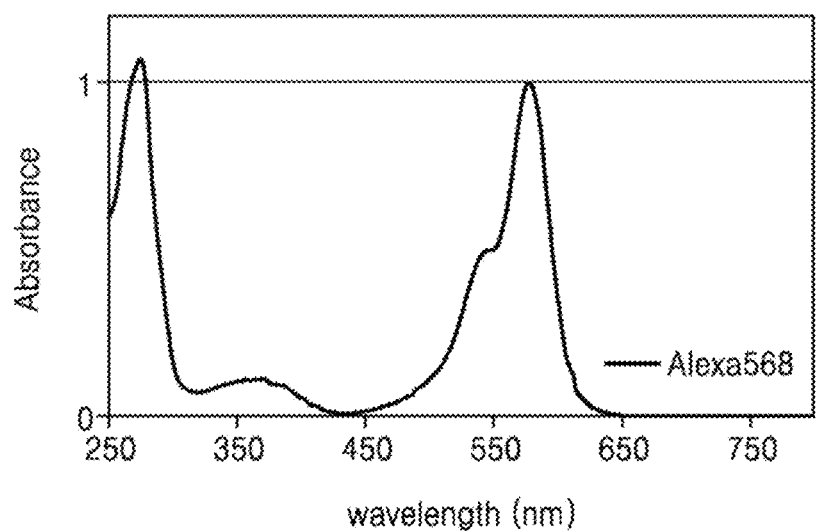
FIG. 1b is an absorption spectrum of goat anti-mouse IgG labeled with Alexa Fluor® 568.
Figure 1C:
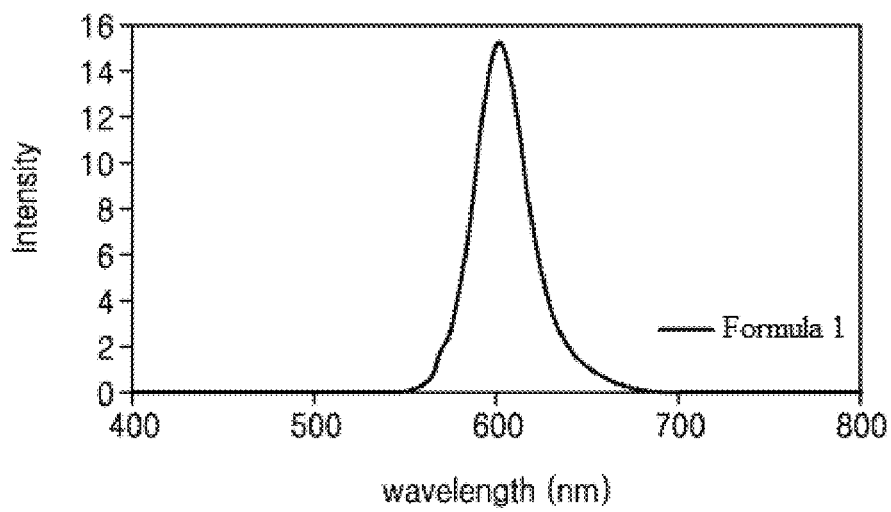
FIG. 1c is a fluorescence emission spectrum of goat anti-mouse IgG labeled with the compound of Formula 1.
Figure 1D:
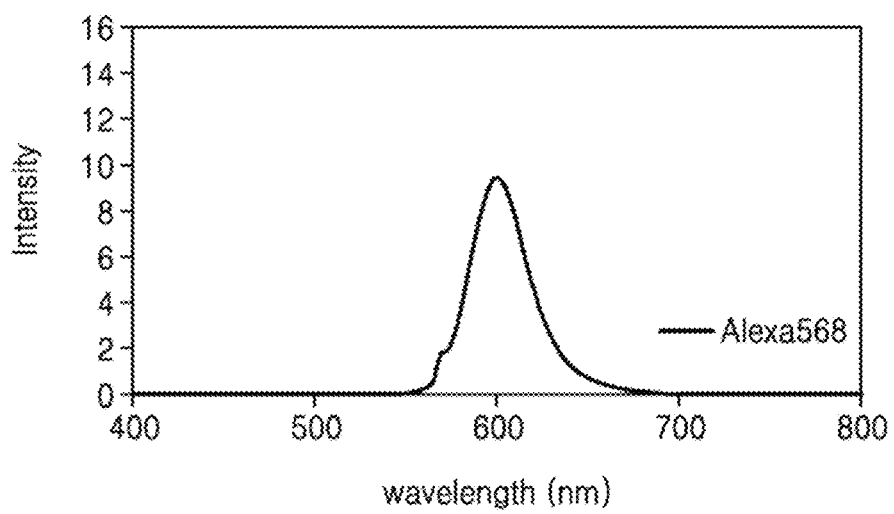
FIG. 1d is a fluorescence emission spectrum of goat anti-mouse IgG labeled with Alexa Fluor® 568.

FIG. 1a is an absorption spectrum of goat anti-mouse IgG labeled with the compound of Formula 1, FIG. 1b is an absorption spectrum of goat anti-mouse IgG labeled with Alexa Fluor® 568, FIG. 1c is a fluorescence emission spectrum of goat anti-mouse IgG labeled with the compound of Formula 1, and FIG. 1d is a fluorescence emission spectrum of goat anti-mouse IgG labeled with Alexa Fluor® 568.

The absorption wavelengths of the compound of Formula 1 were similar to those of Alexa Fluor® 568. The compound of Formula 1 was less aggregated than Alexa Fluor® 568. The fluorescence emission intensity of the compound of Formula 1 was found to be higher than that of Alexa Fluor® 568.

Experimental Example 3

1. Goat anti-mouse IgG was diluted with 0.1 M sodium bicarbonate buffer to prepare a 1 mg/ml protein solution.
2. Five tubes were prepared and the protein solutions (125 μl each) were placed therein.
3. Different amounts (1, 2, 3, 4, and 5 μl) of a dye solution (5 mg/ml) were placed into the tubes, followed by vortexing.
4. The tubes were shaken in a locker at room temperature for ~30 min.
5. The reaction solutions were transferred to Amicon centrifugal filters.
6. The reaction solutions were washed with PBS by centrifugation (14,000 rpm, 10 min, 5 cycles) until free dye was removed.
7. The centrifugal filters were inverted and coupled to the Amicon tubes, and the filtrates were collected (1,000 rpm, 2 min).
8. The filtrates were diluted with PBS (1 ml each).
9. UV, PL, and fluorescence were measured with a microplate reader.

After labeling, the absorbance of the dye and the absorbance of the protein at 280 nm were measured. The ratio of the dye to the protein in each sample was determined using the following equation:

$$\frac{D}{P} = \frac{A_{dye} \times E_{prot}}{(A_{280} \times XA_{dye}) \times E_{dye}}$$

The factor X in the denominator takes into account the maximum absorbance of the dye ($A_{dye}$) and the absorbance of the dye at 280 nm, which corresponds to a % of the maximum absorbance.

Figure 1E:
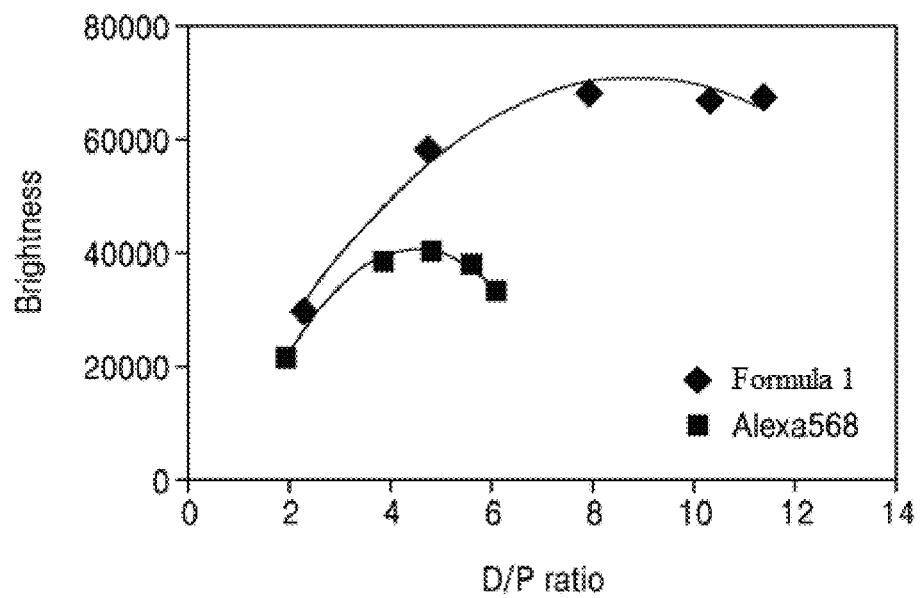
FIG. 1e shows changes in the brightness of goat anti-mouse IgG labeled with the compound of Formula 1 and goat anti-mouse IgG labeled with Alexa Fluor® 568 as a function of D/P ratio.

FIG. 1e shows changes in the brightness of goat anti-mouse IgG labeled with the compound of Formula 1 and goat anti-mouse IgG labeled with Alexa Fluor® 568 as a function of D/P ratio. The brightness values of the compound of Formula 1 were found to be higher than those of Alexa Fluor® 568.

Experimental Example 4

1. IgG from mouse serum (primary) was dissolved to a concentration of 10 μg/ml in coating buffer.
2. 100 μl of the solution was divided into each well of a FLISA H/B black corning plate.
3. After top sealing, the plate was incubated in the dark at room temperature for 2 h.
4. Each well was washed three times with 300 μl of washing buffer.
5. 300 μl of blocking buffer was placed into each well. After top sealing, the plate was incubated in the dark at room temperature for 1 h.
6. After removal of the blocking buffer, the wells were washed three times with washing buffer.
7. 100 μl of a dye-conjugated secondary antibody (10 μg/ml) was placed into each well. After top sealing, the plate was incubated in the dark at room temperature for 1 h.
8. After removal of the solution, each well was washed three times with 200 μl of washing buffer.
9. 100 μl of PBS was placed into each sample-containing well.
10. Fluorescence was measured with a microplate reader.

Figure 1F:
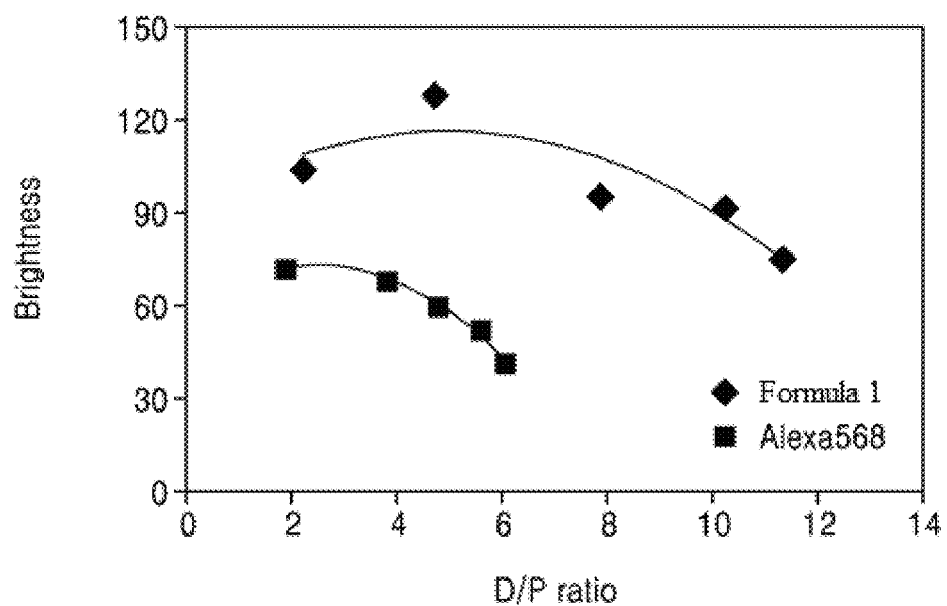
FIG. 1f compares the bioactivity of the compound of Formula 1 with that of Alexa Fluor® 568.

Table 2 shows the fluorescence values of the compound of Formula 1 and Alexa Fluor® 568 in different D/P ratios. FIG. 1f compares the bioactivity of the compound of Formula 1 with that of Alexa Fluor® 568.

TABLE 2

| Formula 1 | | Alexa Fluor® 568 | |
|---|---|---|---|
| D/P ratio | Fluorescence | D/P ratio | Fluorescence |
| 2.202771 | 104.026 | 2.12797 | 72.0106 |
| 4.888795 | 127.5422 | 5.465357 | 68.00017 |
| 8.141409 | 95.40485 | 7.760384 | 60.15061 |
| 11.30465 | 91.8519 | 9.118983 | 52.02349 |
| 12.45994 | 75.09808 | 9.673626 | 41.4303 |

As can be seen from the results in Table 2 and FIG. 1f, when the D/P ratio was ~4.8, the dye (Formula 1)-secondary body was conjugated to the primary antibody with the highest efficiency. In addition, the brightness values of the compound of Formula 1 were found to be much higher than those of Alexa Fluor® 568. The compound of Formula 1 was also found to have better bioactivity than Alexa Fluor® 568.

Experimental Example 5

Goat anti-mouse IgG was labeled with Alexa Fluor® 594 (Thermo Fisher Scientific) and the compound of Formula 3 and their absorption spectra and fluorescence emission spectra were recorded.

Figure 2A:
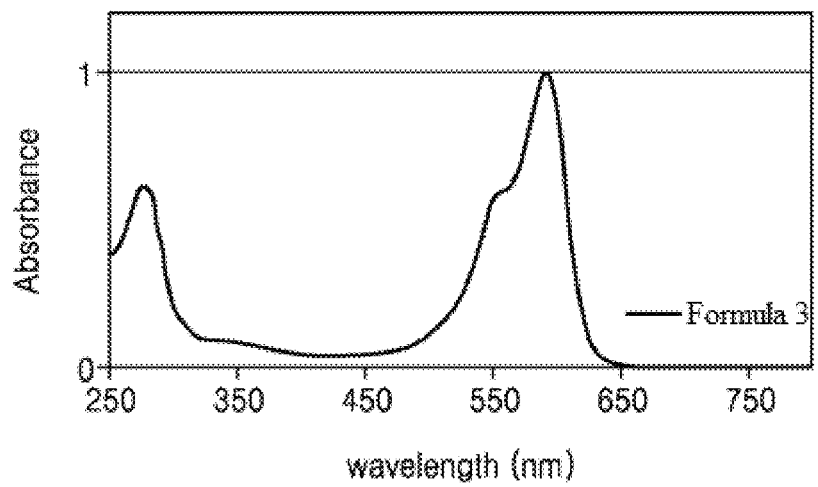
FIG. 2a is an absorption spectrum of goat anti-mouse IgG labeled with the compound of Formula 3.
Figure 2B:
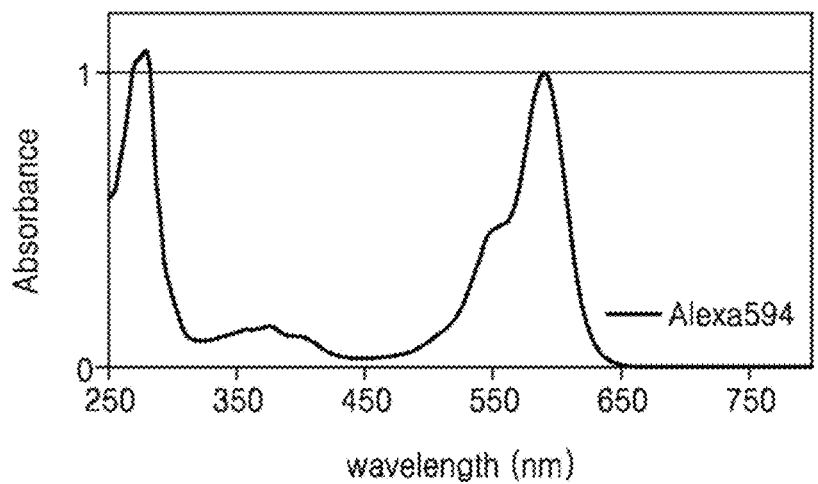
FIG. 2b is an absorption spectrum of goat anti-mouse IgG labeled with Alexa Fluor® 594.
Figure 2C:
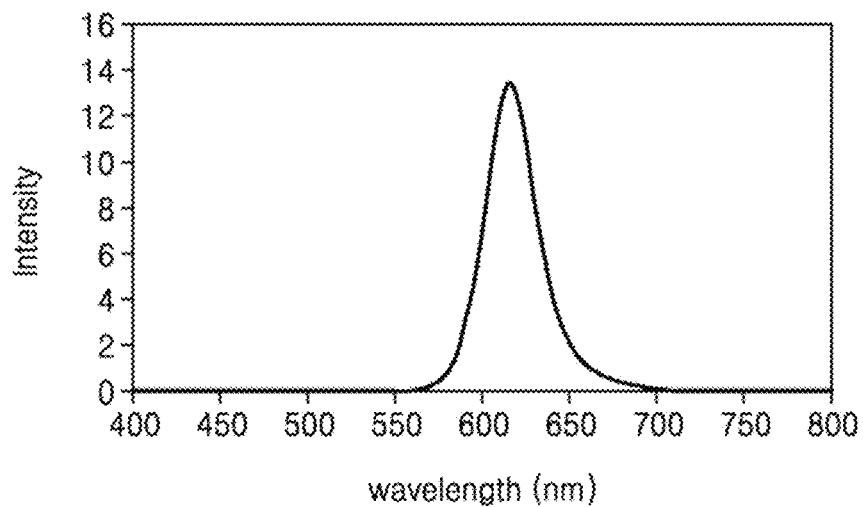
FIG. 2c is a fluorescence emission spectrum of goat anti-mouse IgG labeled with the compound of Formula 3.
Figure 2D:
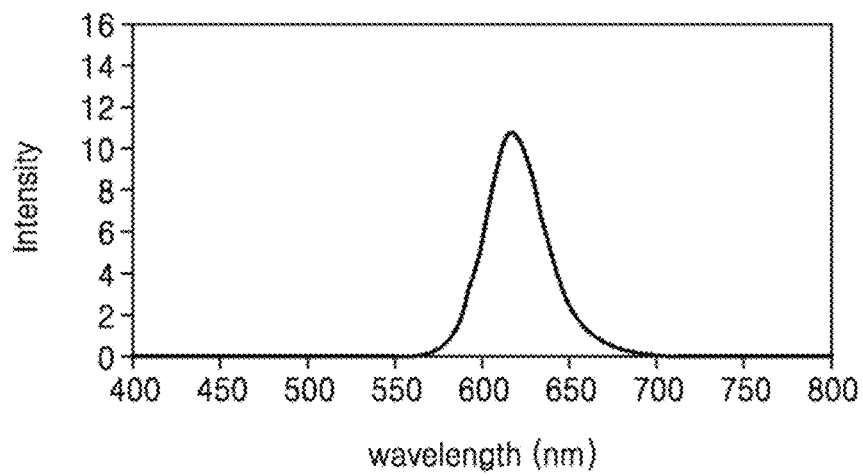
FIG. 2d is a fluorescence emission spectrum of goat anti-mouse IgG labeled with Alexa Fluor® 594.

FIG. 2a is an absorption spectrum of goat anti-mouse IgG labeled with the compound of Formula 3, FIG. 2b is an absorption spectrum of goat anti-mouse IgG labeled with Alexa Fluor® 594, FIG. 2c is a fluorescence emission spectrum of goat anti-mouse IgG labeled with the compound of Formula 3, and FIG. 2d is a fluorescence emission spectrum of goat anti-mouse IgG labeled with Alexa Fluor® 594.

The absorption wavelengths of the compound of Formula 3 were similar to those of Alexa Fluor® 594. In addition, the fluorescence emission intensity of the compound of Formula 3 was found to be higher than that of Alexa Fluor® 594.

Experimental Example 6

The procedure of Experimental Example 3 was repeated except that the compound of Formula 3 was used.

Figure 2E:
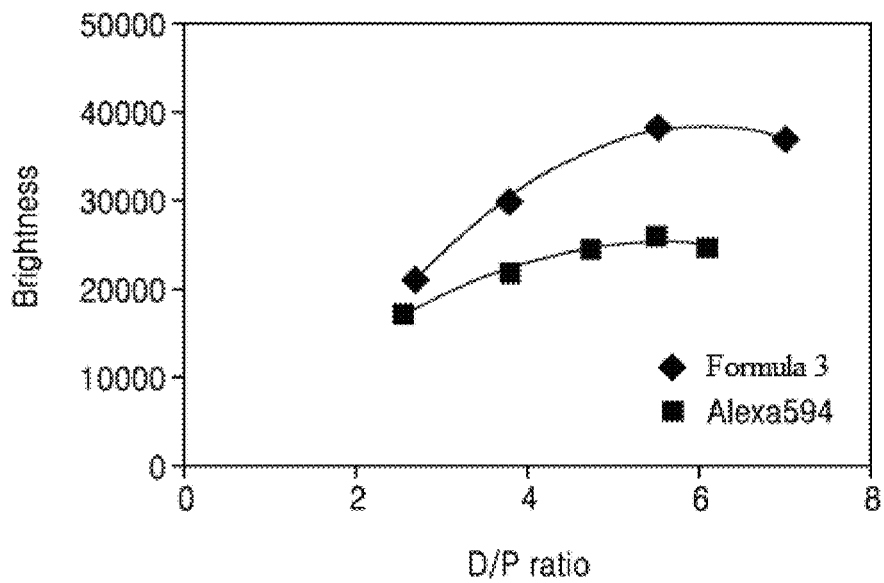
FIG. 2e shows changes in the brightness of goat anti-mouse IgG labeled with the compound of Formula 3 and goat anti-mouse IgG labeled with Alexa Fluor® 594 as a function of D/P ratio.

FIG. 2e shows changes in the brightness of goat anti-mouse IgG labeled with the compound of Formula 3 and goat anti-mouse IgG labeled with Alexa Fluor® 594 as a function of D/P ratio. The brightness values of the compound of Formula 3 were found to be higher than those of Alexa Fluor® 594. Particularly, the difference in brightness between the compound of Formula 3 and Alexa Fluor® 594 increased with increasing D/P ratio.

Experimental Example 7

The procedure of Experimental Example 4 was repeated except that the compound of Formula 3 was used.

Figure 2F:
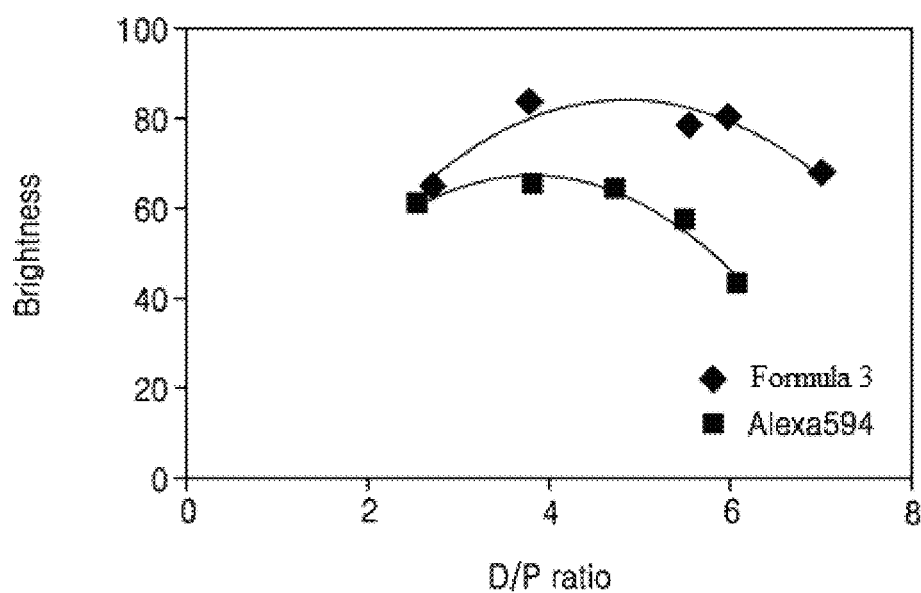
FIG. 2f compares the bioactivity of the compound of Formula 3 with that of Alexa Fluor® 594.

Table 3 shows the fluorescence values of the compound of Formula 3 and Alexa Fluor® 594 in different D/P ratios. FIG. 2f compares the bioactivity of the compound of Formula 3 with that of Alexa Fluor® 594.

TABLE 3

| Formula 3 | | Alexa Fluor® 594 | |
|---|---|---|---|
| D/P ratio | Fluorescence | D/P ratio | Fluorescence |
| 2.54 | 64.89 | 2.55 | 76.07 |
| 3.47 | 83.79 | 3.81 | 81.82 |
| 4.86 | 78.61 | 4.74 | 80.38 |
| 5.18 | 80.28 | 5.50 | 71.62 |
| 5.95 | 68.06 | 6.08 | 54.13 |

As can be seen from the results in Table 3 and FIG. 2f, when the D/P ratio was ~3.4, the dye (Formula 3)-secondary body was conjugated to the primary antibody with the highest efficiency. When the D/P ratio was ≥5, the brightness values of the compound of Formula 3 were found to be much higher than those of Alexa Fluor® 594. The compound of Formula 3 was also found to have better bioactivity than Alexa Fluor® 594.

Experimental Example 8

Absorption spectra ($\lambda_{abs}$), emission spectra ($\lambda_{em}$), molar extinction coefficients, and quantum yields of the compounds of Formulae 44-53 were measured and the results are shown in Table 4.

[Comparative Compound]

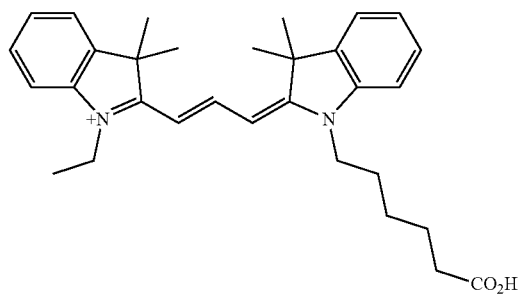 [SMILES: CC[N+]1=C(/C=C/C=C2/N(CCCCCC(=O)O)c3ccccc3C2(C)C)C(C)(C)c2ccccc21]

TABLE 4

| Compound | Solvent | $\lambda_{abs}$ (nm) | $\lambda_{em}$ (nm) | ε (M$^{-1}$cm$^{-1}$) | Quantum yield |
|---|---|---|---|---|---|
| Comparative |  | 548 | 562 | 150,000 | 0.04 |
| Formula 44 | PBS | 544 | 568 | 51,000 | 0.72 |
| Formula 45 | DMSO | 581 | 601 | 55,000 | 0.73 |
| Formula 47 | DMSO | 559 | 580 | 49,000 | 0.45 |
| Formula 48 | DMSO | 570 | 592 | 110,000 | 0.98 |
| Formula 49 | DMSO | 490 | 574 | 28,000 | 0.35 |
| Formula 50 | DMSO | 573 | 596 | 100,000 | 0.95 |
| Formula 51 | DMSO | 595 | 621 | 78,800 | 0.75 |
| Formula 52 | PBS | 541 | 564 |  | 0.61 |
| Formula 53 | DMSO | 546 | 570 | 33,000 | 0.95 |

Experimental Example 9

The procedure of Experimental Example 3 was repeated except that the compound of Formula 50 was used.

Figure 3A:
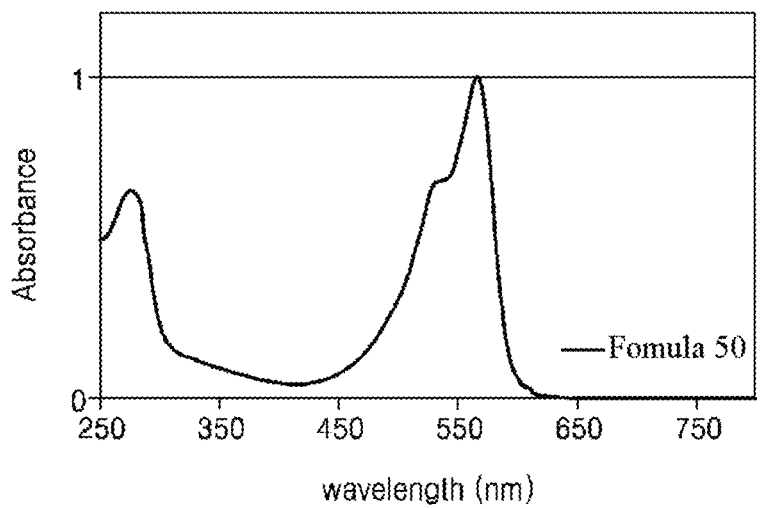
FIG. 3a is an absorption spectrum of goat anti-mouse IgG labeled with the compound of Formula 50.

FIG. 3a is an absorption spectrum of goat anti-mouse IgG labeled with the compound of Formula 50.

Figure 3B:
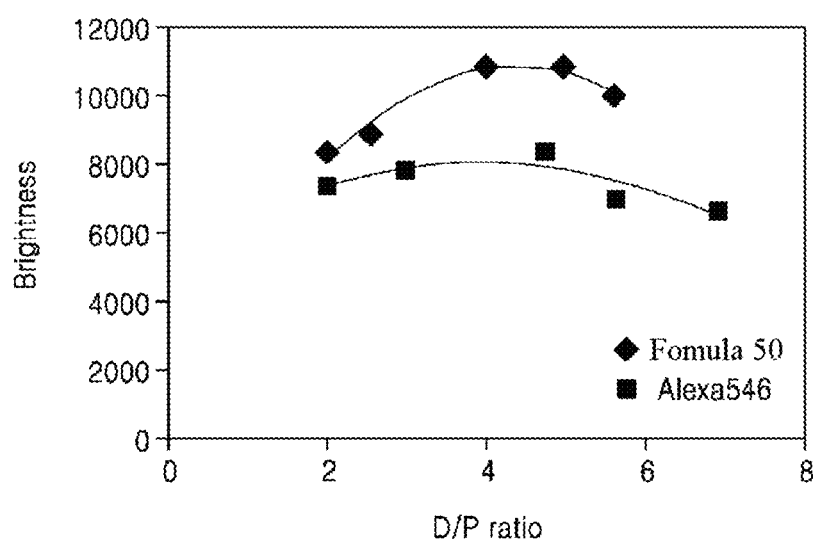
FIG. 3b shows changes in the brightness of goat anti-mouse IgG labeled with the compound of Formula 50 and goat anti-mouse IgG labeled with Alexa Fluor® 546.

FIG. 3b shows changes in the brightness of goat anti-mouse IgG labeled with the compound of Formula 50 and goat anti-mouse IgG labeled with Alexa Fluor® 546. The brightness values of the compound of Formula 50 were found to be higher than those of Alexa Fluor® 546.

Experimental Example 10

The procedure of Experimental Example 4 was repeated except that the compound of Formula 50 was used.

Figure 3C:
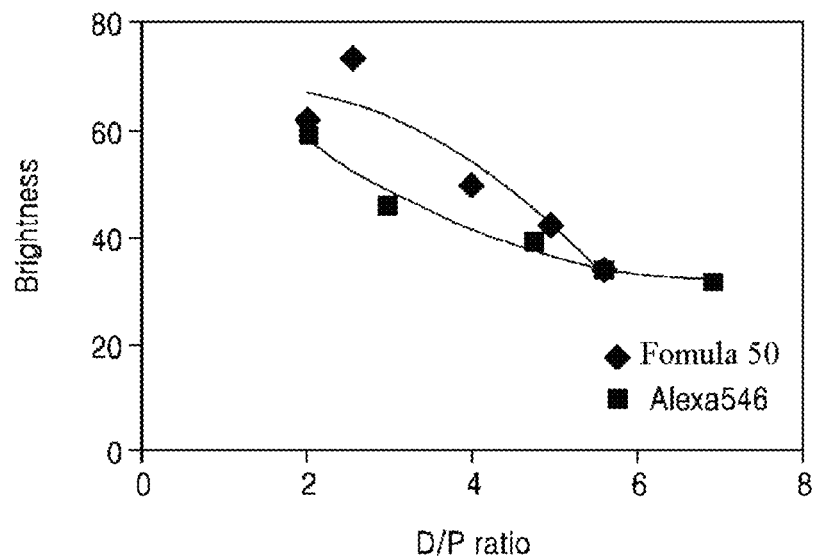
FIG. 3c compares the bioactivity of the compound of Formula 4450 with that of Alexa Fluor® 546.

Table 5 shows the fluorescence values of the compound of Formula 50 and Alexa Fluor® 546 in different D/P ratios. FIG. 3c compares the bioactivity of the compound of Formula 50 with that of Alexa Fluor® 546.

TABLE 5

Formula 50

| D/P ratio | Fluorescence |
|---|---|
| 1.995678 | 59.97054 |
| 2.536109 | 69.32306 |
| 3.981585 | 50.97775 |
| 4.954446 | 43.58956 |
| 5.593174 | 36.24333 |

As can be seen from the results in Table 5 and FIG. 3c, when the D/P ratio was ~2.5, the dye (Formula 50)-secondary body was conjugated to the primary antibody with the highest efficiency. In addition, the brightness values of the compound of Formula 50 were found to be much higher than those of Alexa Fluor® 546.

Experimental Example 11: Evaluation of Optical Properties of the Inventive Compounds The inventive dye compounds showed much higher fluorescence quantum yields than conventional cyanine dye compounds. As shown in Table 6, the inventive dye compounds had lower molar extinction coefficients but showed much higher fluorescence quantum yields than the following comparative compound.

Comparative Compound

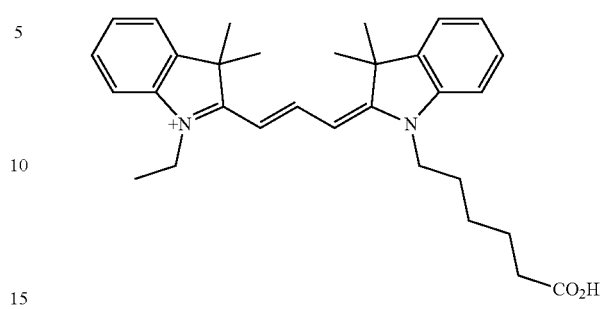

The products of the two factors (molar extinction coefficient×fluorescence quantum yield) for the inventive dye compounds were much greater than that for the comparative compound.

TABLE 6

| Compound | Solvent | $\lambda_{abs}$ (nm) | $\lambda_{em}$ (nm) | ε (M$^{-1}$cm$^{-1}$) | Quantum yield |
|---|---|---|---|---|---|
| Formula 97 | PBS | 541 | 565 | 14,000 | 0.63 |
|  | DMSO | 551 | 568 | 35,000 | 0.94 |
|  | EtOH | 555 | 567 | 47,000 | 0.90 |
| Formula 98 | PBS | 565 | 595 | 57,000 | 0.51 |
|  | DMSO | 570 | 601 | 57,000 | 0.77 |
|  | EtOH | 570 | 596 | 64,000 | 0.78 |
| Formula 99 | PBS | 463 | 558 | 30,000 | 0.42 |
|  | DMSO | 467 | 563 | 21,000 | 0.65 |
|  | EtOH | 474 | 558 | 22,000 | 0.52 |
| Formula100 | PBS | 589 | 608 | 54,000 | 0.80 |
|  | DMSO | 594 | 618 | 65,000 | 0.90 |
|  | EtOH | 592 | 612 | 75,000 | 0.90 |
| Formula101 | PBS | 578 | 619 | 49,000 | 0.61 |
|  | DMSO | 584 | 630 | 54,000 | 0.70 |
|  | EtOH | 585 | 623 | 66,000 | 0.87 |
| Formula102 | PBS | 524 | 571 | 7,100 | 0.70 |
|  | DMSO | 570 | 586 | 23,000 | 0.99 |
|  | EtOH | 557 | 578 | 6,800 | 0.78 |
| Formula103 | PBS | 516 | 563 | 48,000 | 0.79 |
|  | DMSO | 566 | 586 | 108,000 | 0.88 |
|  | EtOH | 547 | 574 | 70,000 | 0.84 |
| Formula104 | PBS | 559 | 572 | 28,000 | 0.09 |
|  | DMSO | 646 | 685 | 52,000 | 0.38 |
| Formula105 | PBS | 604 | 643 | 35,000 | 0.28 |
|  | DMSO | 613 | 649 | 37,000 | 0.70 |
|  | EtOH | 611 | 645 | 44,000 | 0.50 |
| Formula106 | PBS | 616 | 652 | 29,000 | 0.21 |
|  | DMSO | 620 | 660 | 55,000 | 0.72 |
|  | EtOH | 620 | 657 | 70,000 | 0.59 |
| Formula107 | PBS | 624 | 655 | 37,000 | 0.29 |
|  | DMSO | 629 | 664 | 40,000 | 0.70 |
|  | EtOH | 628 | 659 | 50,000 | 0.52 |
| Formula108 | PBS | 630 | 651 | 74,000 | 0.37 |
|  | DMSO | 627 | 650 | 64,000 | 0.52 |
| Formula109 | PBS | 559 | 582 | 47,000 | 0.46 |
|  | DMSO | 569 | 590 | 73,000 | 0.93 |
| Formula110 | PBS | 550 | 579 | 37,000 | 0.78 |
|  | DMSO | 561 | 597 | 37,000 | 0.86 |
|  | EtOH | 558 | 584 | 50,000 | 0.80 |
| Formula111 | PBS (pH 7.4) | 530 | 585 | 55,000 | 0.53 |
| Comparative |  | 548 | 562 | 150,000 | 0.04 |

Experimental Example 12: Selectivity of the Inventive Compound for Mitochondria

The specific selectivity of the compound of Formula 110 for mitochondria was investigated. To this end, Raw 264.7 cells were co-localized with the compound of Formula 110 and a commercially available mitochondrial marker (MTG, 1 µM MitoTracker Green FM for mitochondria).

Figure 4A:
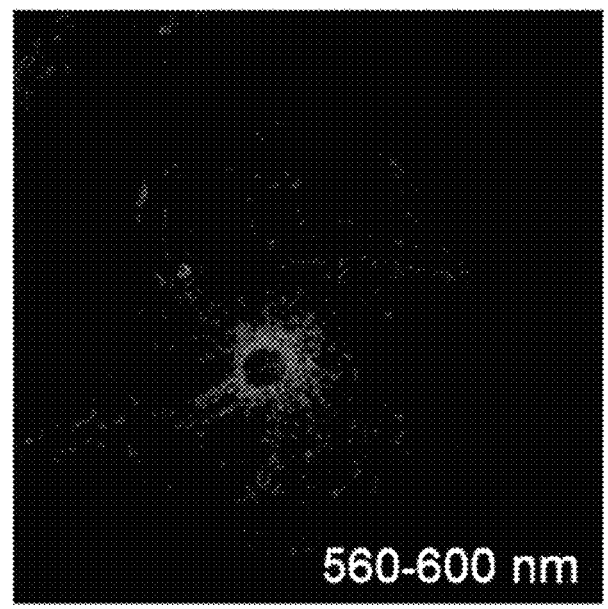
FIG. 4a is an image of Raw 264.7 cells labeled with the compound of Formula 110, which was acquired at an excitation wavelength of 552 nm and an emission wavelength of 560-600 nm.
Figure 4B:
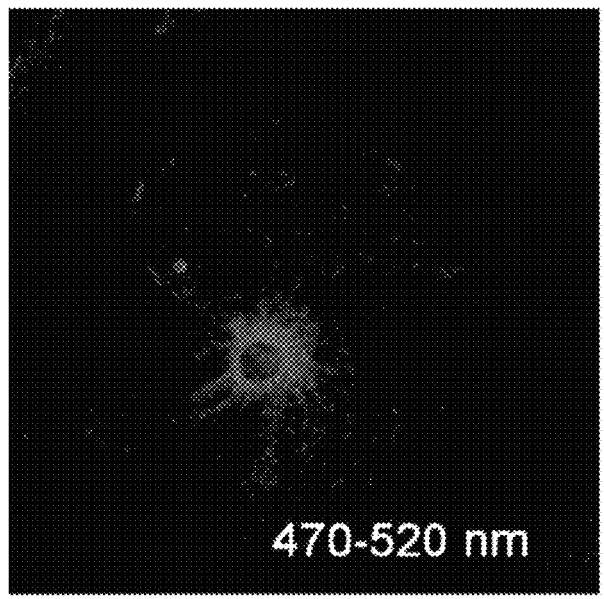
FIG. 4b is an image of Raw 264.7 cells labeled with Mitotracker Green FM (MTG), which was acquired at an excitation wavelength of 488 nm and an emission wavelength of 470-520 nm.
Figure 4C:
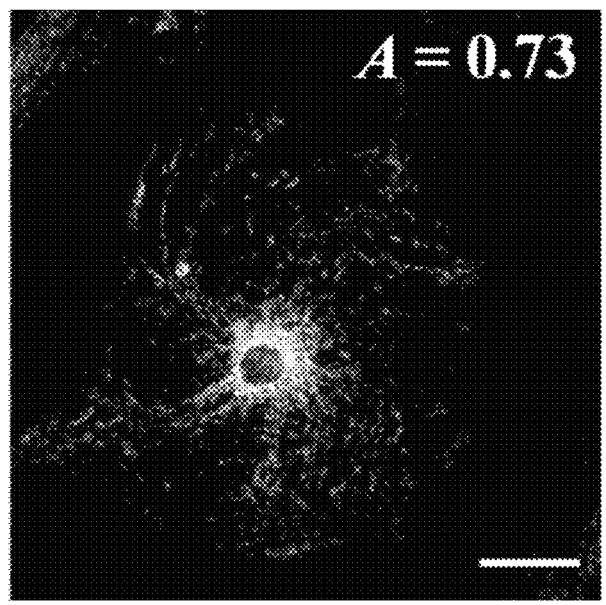
FIG. 4c is a merged image of FIGS. 4a and 4b. The Pearson's co-localization coefficient (A=0.73) was calculated using the LAS AF software.

The structure of MitoTracker Green FM (Thermo Fisher Scientific) is as follows:

OPM images were acquired at 560-600 nm (Formula 110, $\lambda_{ex}$=552 nm) and 470-520 nm (MTG, $\lambda_{ex}$=488 nm) and are shown in FIGS. 4a and 4b, respectively. FIG. 4c is a merged image of FIGS. 4a and 4b. The Pearson's co-localization coefficient (A) was calculated using the LAS AF software.

[MTG]=1µM for 30 min incubation,$\lambda_{ex}$=488 nm

[Formula 110]=1µM for 30 min incubation,$\lambda_{ex}$=552 nm

The degree of overlapping (A) of the two images stained with Mitotracker Green FM (MTG) and the compound of Formula 110 was 0.73, confirming that mitochondria were predominantly stained. These results demonstrate the ability of the dye of Formula 110 to more selectively stain and more accurately image mitochondria than other intracellular organelles.

Experimental Example 13

The fluorescence intensities of three areas A, B, and C of HeLa A431 cells stained with the compound of Formula 110 (1.0 µM) were measured at 2-sec intervals for 3500 sec. The results are shown in FIG. 5.

Figure 5:
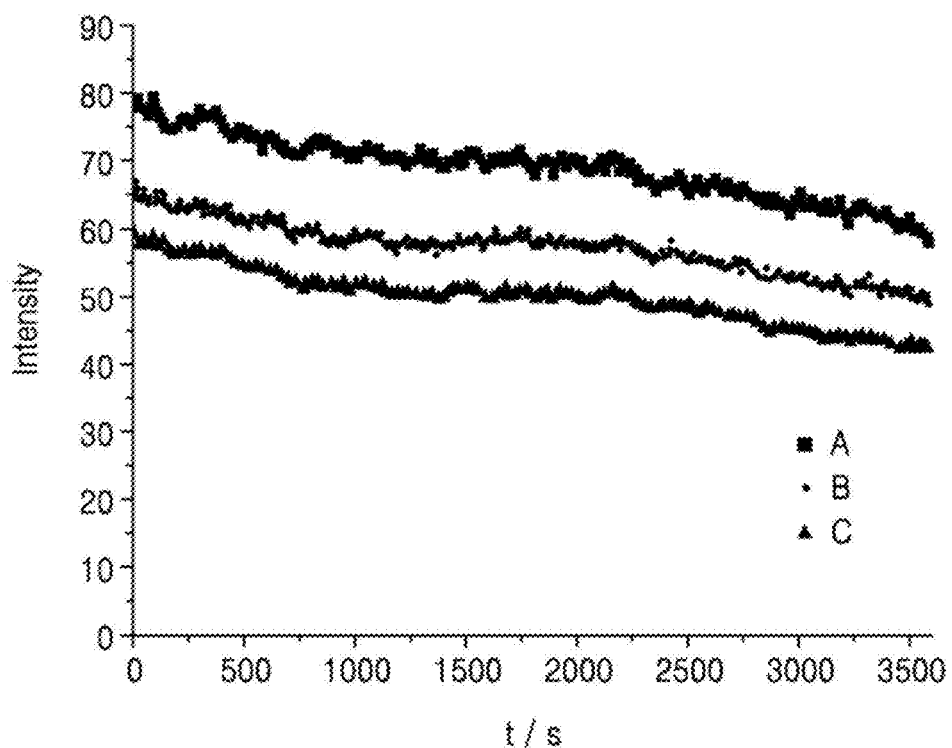
FIG. 5 shows fluorescence intensities of three areas A, B, and C of HeLa A431 cells stained with the compound of Formula 110 (1.0 μM), which were measured at 2-sec intervals for 3500 sec.

As shown in FIG. 5, there were no substantial decreases in fluorescence intensity for 1 h, indicating good photostability of the compound of Formula 110.

Experimental Example 14: Selectivity of the Inventive Compound for Mitochondria

The specific selectivity of the compound of Formula 97 for mitochondria was investigated. To this end, HeLa A431 cells were co-localized with the compound of Formula 97 and a commercially available mitochondrial marker (MTG, 0.2 µM MitoTracker Green FM for mitochondria).

Figure 6A:
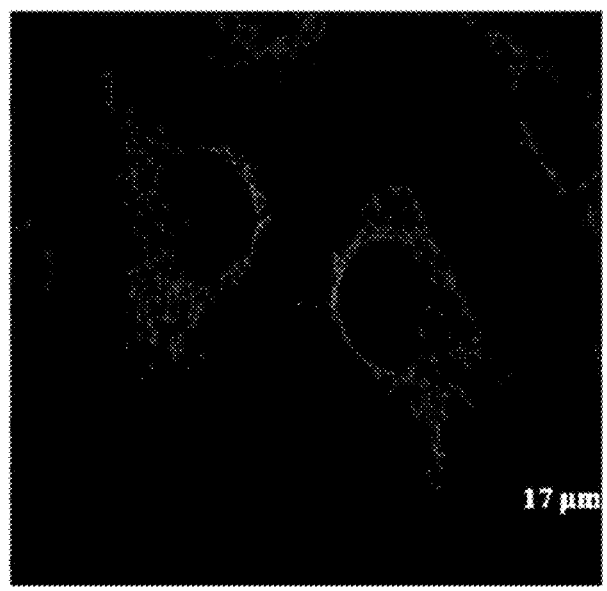
FIG. 6a is an image of HeLa A431 cells labeled with the compound of Formula 97, which was acquired at an excitation wavelength of 552 nm and an emission wavelength of 571-650 nm.
Figure 6B:
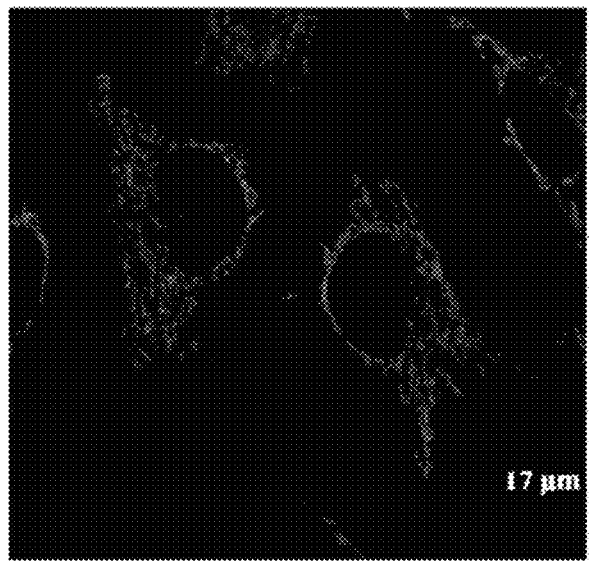
FIG. 6b is an image of HeLa A431 cells labeled with Mitotracker Green FM (MTG), which was acquired at an excitation wavelength of 488 nm and an emission wavelength of 498-540 nm.
Figure 6C:
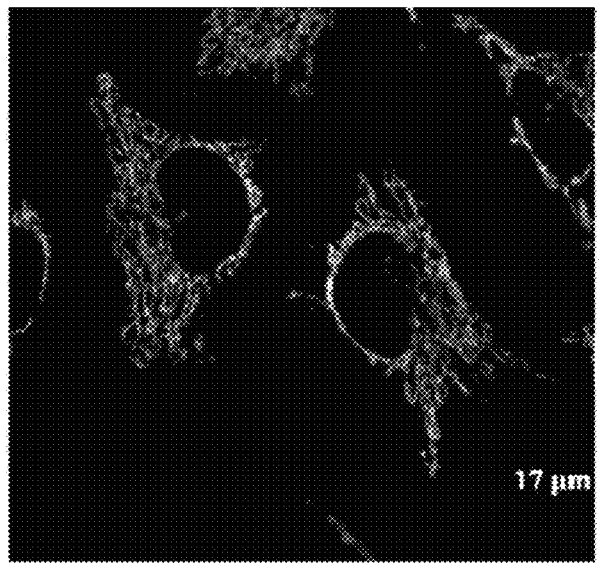
FIG. 6c is a merged image of FIGS. 6a and 6b.

OPM images were acquired at 571-650 nm (Formula 97, $\lambda_{ex}$=552 nm) and 498-540 nm (MTG, $\lambda_{ex}$=488 nm) and are shown in FIGS. 6a and 6b, respectively. FIG. 6c is a merged image of FIGS. 6a and 6b. The Pearson's co-localization coefficient (A) was calculated using the LAS AF software.

[MTG]=0.2µM for 30 min incubation,$\lambda_{ex}$=488 nm

[Formula 97]=0.5µM for 30 min incubation,$\lambda_{ex}$=552 nm

The degree of overlapping (A) of the two images stained with Mitotracker Green FM (MTG) and the compound of Formula 97 was 0.74, confirming that mitochondria were predominantly stained. These results demonstrate the ability of the dye of Formula 97 to more selectively stain and more accurately image mitochondria than other intracellular organelles.

Experimental Example 15

The fluorescence intensities of four areas A, B, C, and D of HeLa A431 cells stained with the compound of Formula 98 (1.0 µM) were measured at 2-sec intervals for 3500 sec. The results are shown in FIG. 7.

Figure 7:
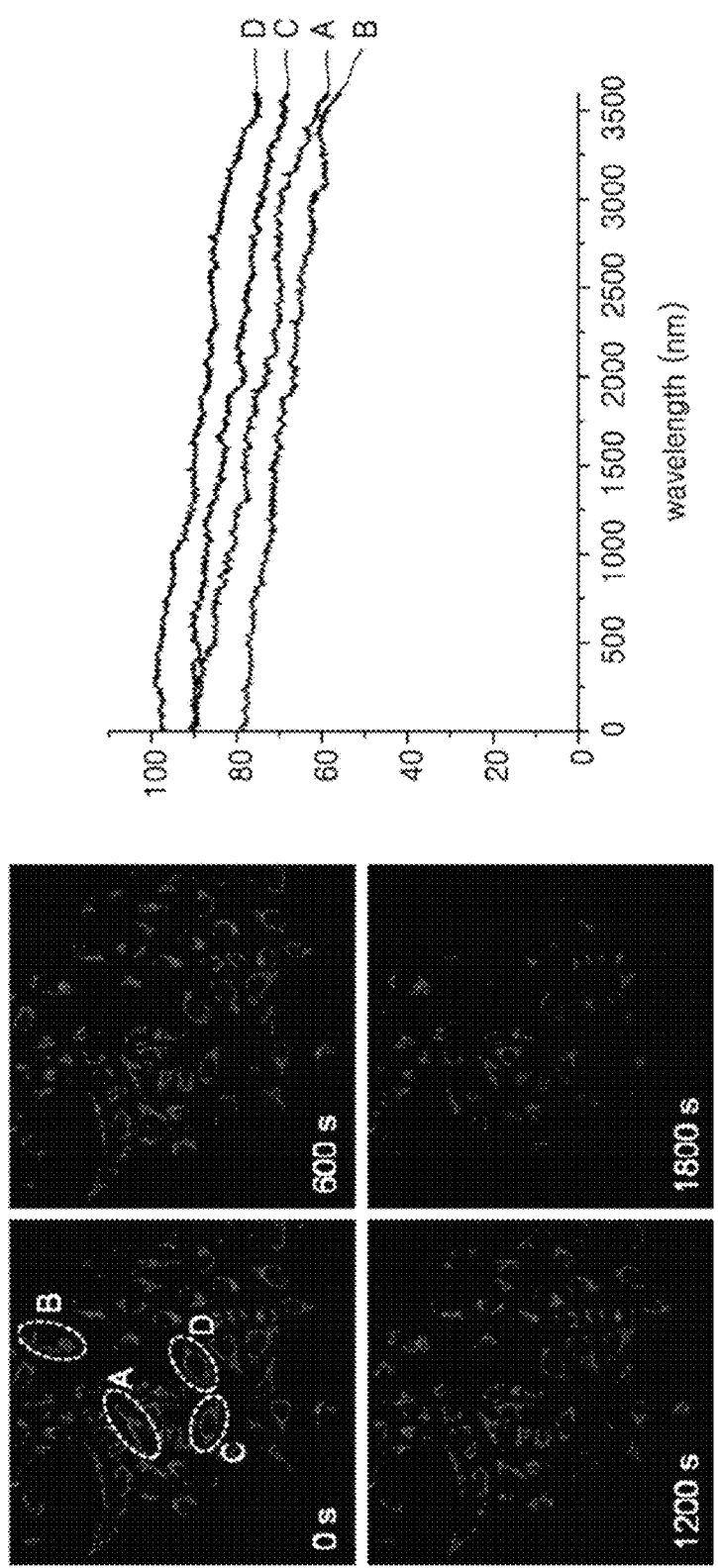
FIG. 7 shows fluorescence intensities of four areas A, B, C, and D of HeLa A431 cells stained with the compound of Formula 98 (1.0 μM), which were measured at 2-sec intervals for 3500 sec.

As shown in FIG. 7, there were no substantial decreases in fluorescence intensity for 1 h, indicating good photostability of the compound of Formula 98.

Comparative Experimental Example 1

The fluorescence intensities of two areas A and B of HeLa A431 cells stained with Cy3B (1.0 µM) were measured at intervals of 2 s for 2000 s. The results are shown in FIG. 8.

Cy3B™

Figure 8:
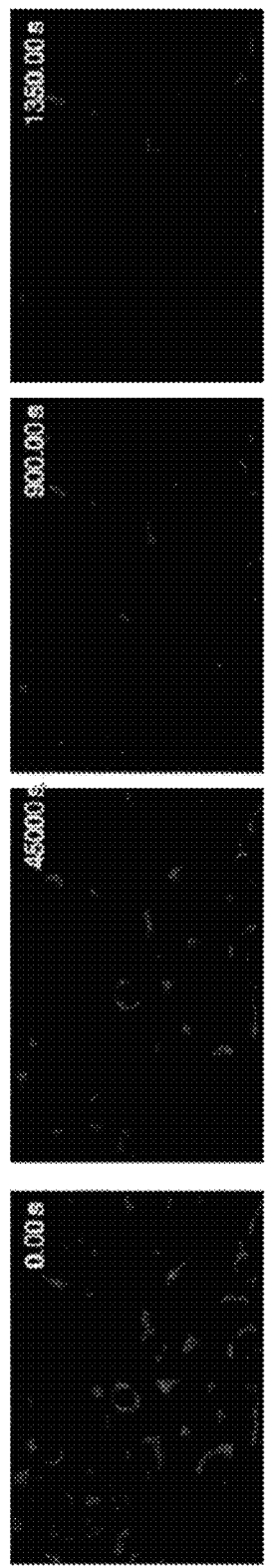
FIG. 8 shows fluorescence intensities of two areas A and B of HeLa A431 cells stained with Cy3B (1.0 μM), which were measured at 2-sec intervals for 2000 sec in Comparative Experimental Example 1.
Figure 8:
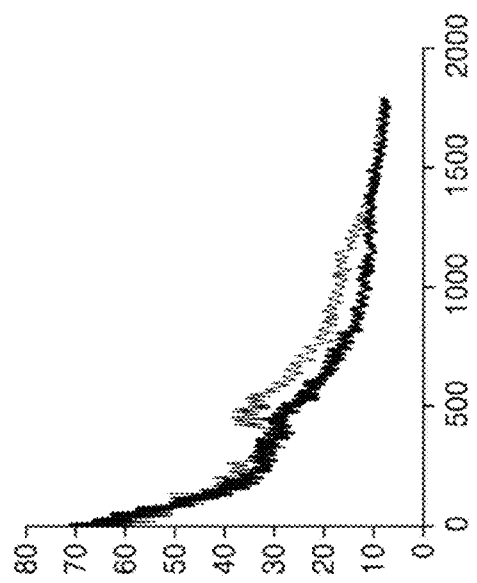

As shown in FIG. 8, the fluorescence intensities were greatly reduced for 1500 s, indicating poor photostability of Cy3B over the inventive dye compounds.

Figure 9:
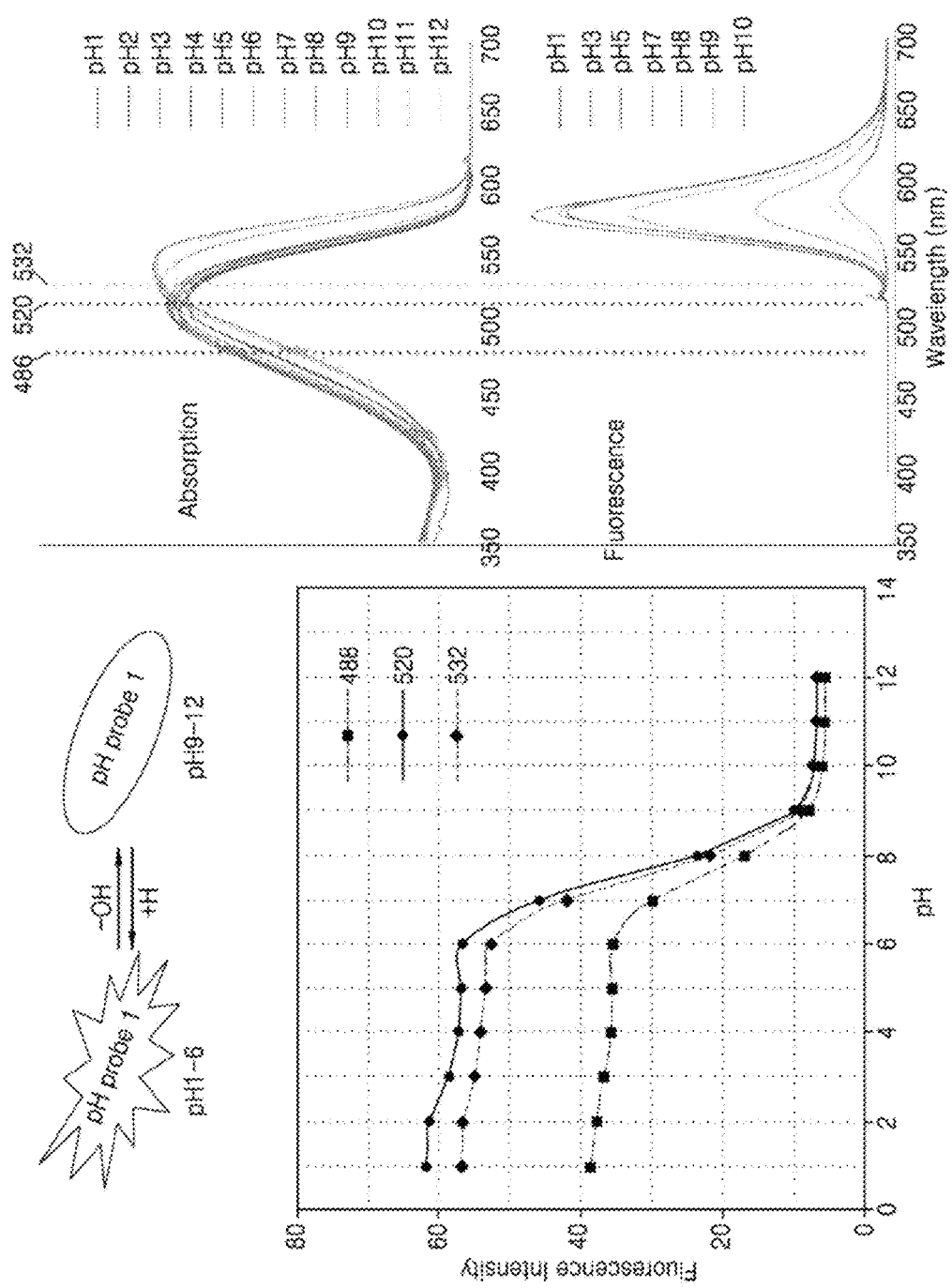
FIGS. 9 and 10 show the characteristics of the compounds of Formulae 111 and 97 as pH probes, respectively.
Figure 10:
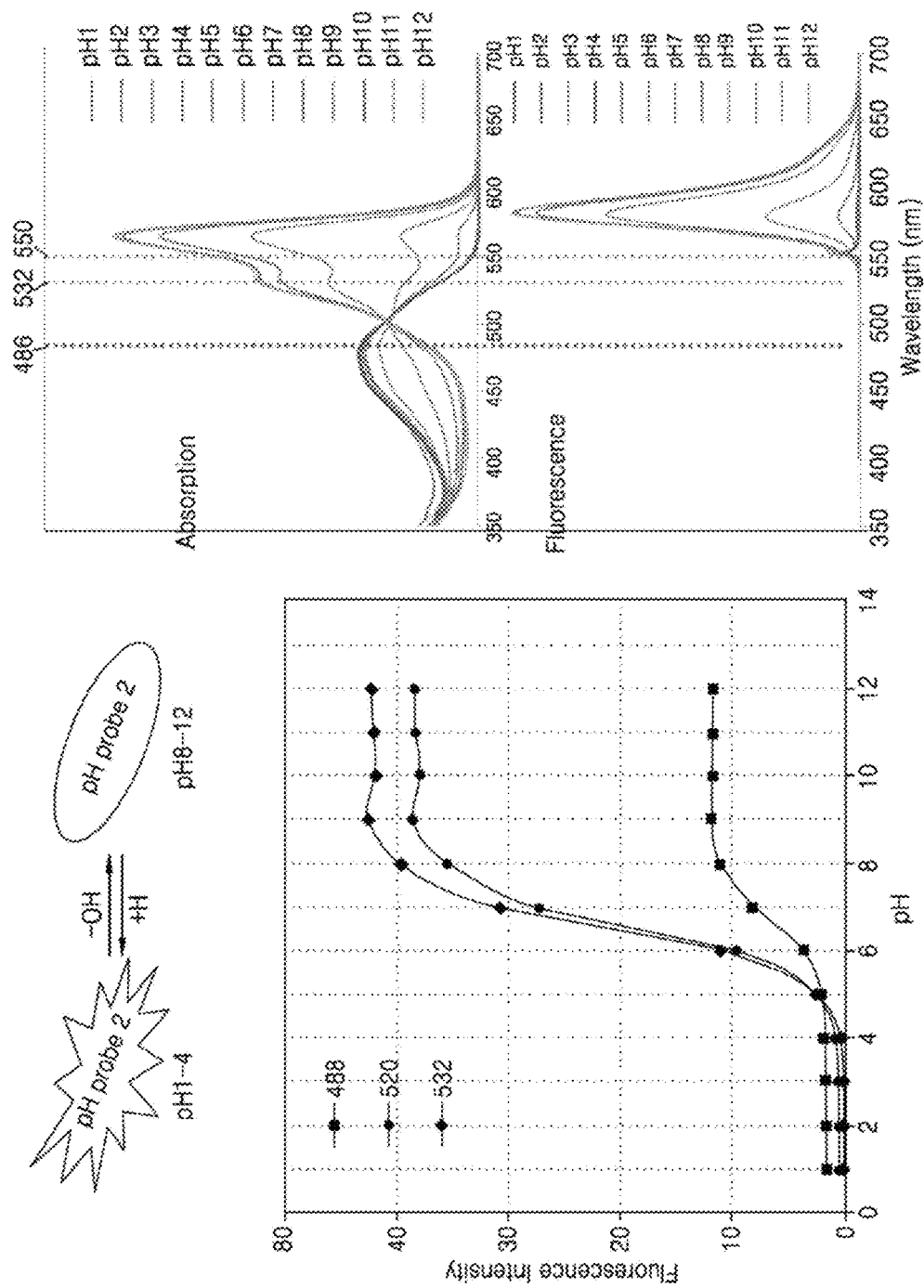

Experimental Examples 16-17: Characterization of the Inventive Compounds as pH Probes As shown in FIGS. 9 and 10, the fluorescence intensity of the compound of Formula 111 increased under acidic conditions (pH 1-6) but decreased under basic conditions (pH 9-12), indicating that the compound of Formula 111 is suitable for use as a probe capable of labeling acidic organelles in live cells due to its high selectivity for cellular organelles under acid conditions. In contrast, the fluorescence intensity of the compound of Formula 97 decreased under acidic conditions (pH 1-6) but increased under basic conditions (pH 9-12), indicating that the compound of Formula 97 is suitable for use as a probe. In addition, the absorption and fluorescence wavelengths of the compound of Formula 97 well match currently available laser lines (488 nm, 532 nm, and 550 nm).

That is, the compound of Formula 111 as a pH probe emitted strong fluorescence at pH 2-6 and the compound of Formula 97 as a pH probe emitted strong fluorescence at pH 8-12. In conclusion, the two types of dyes can be selectively used according to their purpose of use.

The fluorescence intensities of the inventive dye compounds vary in response to pH change. Based on this pH-dependent behavior, the inventive dye compounds can be used as pH probes for measuring the pH of live cells. In addition, the inventive dye compounds can be used in various application fields where pH measurement is required, including not only methods for pH measurement through cell staining but also recent methods for cellular pH measurement using plate readers.

Experimental Example 18

The photophysical properties of the compounds of Formulae 97 and 100-102 were evaluated and the results are shown in Table 7. All measurements were performed in DMSO, ethanol, and PBS buffer. Two-photon cross-sections (δ) were measured using a femtosecond (fs) fluorescence measurement technique.

Figure 11:
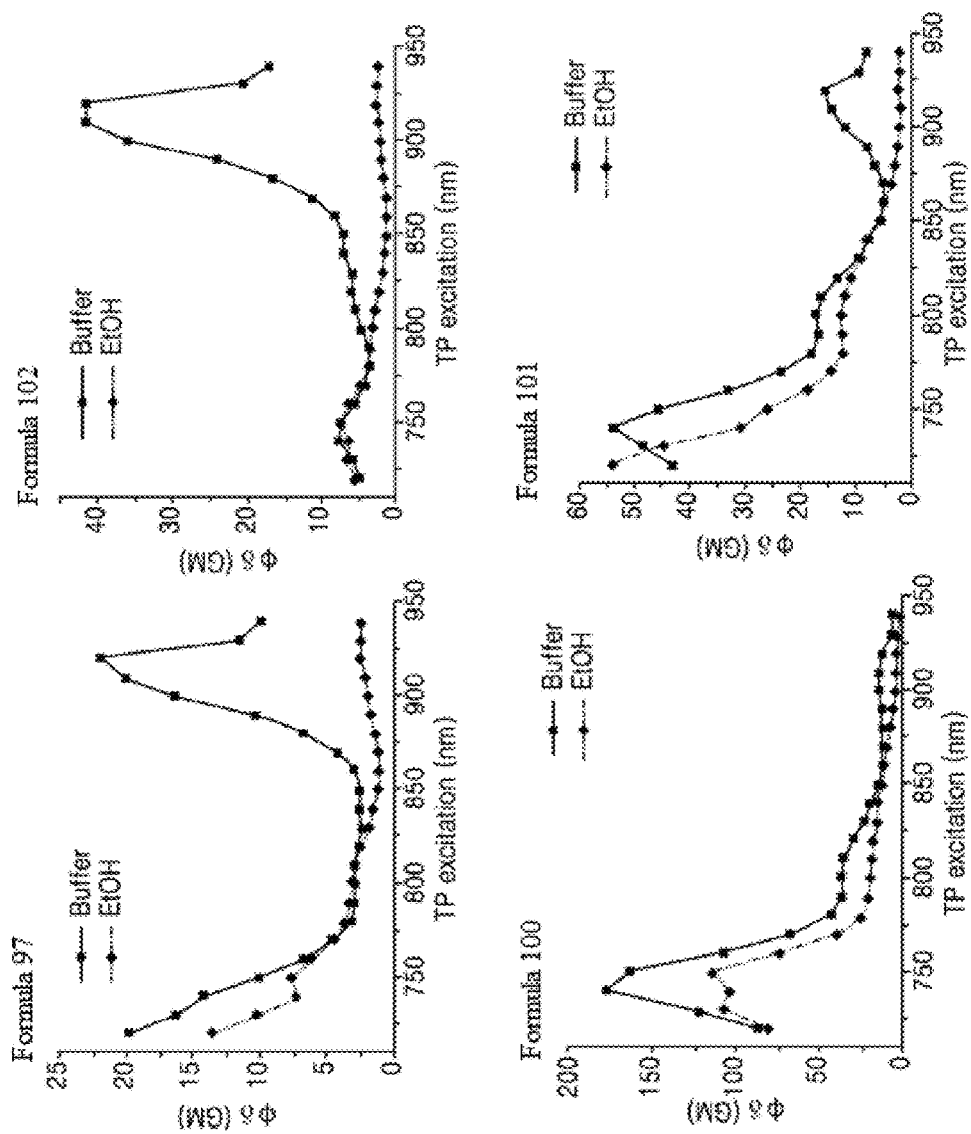
FIG. 11 shows two-photon action spectra of the compounds of Formulae 97, 100, 101, and 102 in PBS buffer and ethanol.

FIG. 11 shows two-photon action spectra of the compounds of Formulae 97, 100, 101, and 102 in PBS buffer and ethanol.

TABLE 7

| Compound | Solvent | $\lambda_{max}^{abs}$ | $\lambda_{max}^{fl}$ | Φ | eΦ | $\lambda^{(2)}{}_{max}^{abs}$ | d | dΦ |
|---|---|---|---|---|---|---|---|---|
| Formula 97 | Buffer | 541 | 565 | 0.63 | 8820 | 920 | 35 | 22 |
| | EtOH | | | | | 720 | | 14 |
| | DMSO | 551 | 567 | 0.94 | | | | |
| Formula 102 | Buffer | 524 | 571 | 0.70 | 4970 | 910 | 60 | 42 |
| | EtOH | | | | | 750 | | 7.6 |
| | DMSO | 570 | 586 | 1.00 | | | | |
| Formula 100 | Buffer | 589 | 611 | 0.65 | 61750 | 740 | 272 | 177 |
| | EtOH | | | | | 750 | | 114 |
| | DMSO | 594 | 618 | 0.90 | | | | |
| Formula 101 | Buffer | 578 | 619 | 0.61 | 29890 | 740 | 89 | 54 |
| | EtOH | | | | | 720 | | 54 |
| | DMSO | 584 | 630 | 0.70 | | | | |

$\lambda_{max}^{abs}$: Maximum wavelength (nm) in single-photon absorption spectrum
$\lambda_{max}^{fl}$: Maximum wavelength (nm) in single-photon emission spectrum
Φ: Fluorescence quantum yield
eΦ: Molar extinction coefficient × fluorescence quantum yield
$\lambda^{(2)}{}_{max}^{abs}$: Maximum wavelength (nm) in two-photon absorption spectrum
d: Peak two-photon cross-section in $10^{-50}$ cm$^4$s per photon (GM)
dΦ: Two-photon action cross-section

INDUSTRIAL APPLICABILITY

As is apparent from the foregoing, the dye compounds of the present invention have markedly improved quantum yields and emit strong fluorescence compared to existing cyanine dyes. Due to these advantages, the dye compounds of the present invention can find applications in various fields, for example, as probes for various biological systems where optical imaging is required.

Particularly, the dye compounds of the present invention can be used as mitotrackers capable of labeling and tracking mitochondria. Therefore, the dye compounds of the present invention can be used to quantitatively image mitochondria in live tissues and cells. Furthermore, the dye compounds of the present invention can be applied as pH probes for measuring the pH of live cells.

What is claimed is:
1. A dye compound represented by Formula I or II:

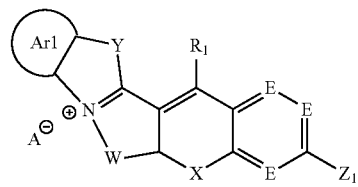

[Formula I]

wherein $Ar_1$ is $C_6$-$C_{20}$ aryl or $C_2$-$C_{20}$ heteroaryl which is optionally substituted with one or more substituents selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, hydroxyl, aldehyde, amino, amide, hydrazine, thiol, acetal, ketal, phosphoryl, phosphate, phosphonate, sulfohydroxyl, sulfonate, sulfate, carboxylate, azido, aminothiocarbonyl, carboxyl, carboxylic acid, ketone, sulfhydryl, acyl chloride, sulfonic acid, polyalkylene oxide, and polyethylene glycol, the alkyl, alkenyl, alkynyl, aryl, heteroaryl, arylalkyl, aryloxy, aryloxyalkyl, alkoxy, and alkoxyalkyl being optionally further substituted with one or more substituents selected from halogen, cyano, nitro, amine, hydroxyl, aldehyde, amino, amide, hydrazine, thiol, acetal, ketal, phosphoryl, phosphate, phosphonate, sulfohydroxyl, sulfonate, sulfate, carboxylate, azido, aminothiocarbonyl, carboxyl, carboxylic acid, ketone, sulfhydryl, acyl chloride, sulfonic acid, polyalkylene oxide, and polyethylene glycol,
each E is $CR_1$ or N,
$Z_1$ is $NR_2R_3$, $OR_4$ or $SR_5$,
X is O, S, $NR_8$, $SiR_{10}R_{11}$, $CR_{12}R_{13}$ or Se,
Y is $CR_{14}R_{15}$, $NR_{16}$, O, S, Se, $SiR_{17}R_{18}$ or $CR_{19}R_{20}$=$CR_{21}R_{22}$, W is $CR_{23}R_{24}$, $CR_{25}R_{26}=CR5_{27}R_{28}$, O, —[$CR_{29}R_{30}$—$CR_{31}R_{32}$]— or —[$CR_{33}R_{34}$—O]—, $R_{23}$ to $R_{34}$ are identical to or different from each other and are each independently hydrogen, deuterium, alkyl or acryloxy, or two adjacent substituents are optionally linked to each other to form an alicyclic hydrocarbon, two of $R_1$ to $R_3$ optionally form an alicyclic hydrocarbon ring or a monocyclic or polycyclic aromatic hydrocarbon ring with two of the adjacent substituents, and carbon atom of the alicyclic or aromatic hydrocarbon ring is optionally replaced by a substituent selected from N, S, O, Se, Te, Po, $NR_{35}$, $SiR_{36}R_{37}$, $GeR_{38}R_{39}$, $PR_{40}$, and $BR_{41}$, or $R_1$ to $R_8$, $R_{10}$ to $R_{22}$ and $R_{35}$ to $R_{41}$ are identical to or different from each other and are each independently selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, hydroxyl, aldehyde, amino, amide, hydrazine, thiol, acetal, ketal, phosphoryl, phosphate, phosphonate, sulfohydroxyl, sulfonate, sulfate, carboxylate, azido, aminothiocarbonyl, carboxyl, carboxylic acid, ketone, sulfhydryl, acyl chloride, sulfonic acid, polyalkylene oxide, and polyethylene glycol, the alkyl, alkenyl, alkynyl, aryl, heteroaryl, arylalkyl, aryloxy, aryloxyalkyl, alkoxy, and alkoxyalkyl being optionally further substituted with one or more substituents selected from halogen, cyano, nitro, amine, hydroxyl, aldehyde, amino, amide, hydrazine, thiol, acetal, ketal, phosphoryl, phosphate, phosphonate, sulfohydroxyl, sulfonate, sulfate, carboxylate, azido, aminothiocarbonyl, carboxyl, carboxylic acid, ketone, sulfhydryl, acyl chloride, sulfonic acid, polyalkylene oxide, and polyethylene glycol, and $A^-$ is an anion or a cation represented by $A^+$ as an organic or inorganic ion and is optionally absent; or

[Formula II]

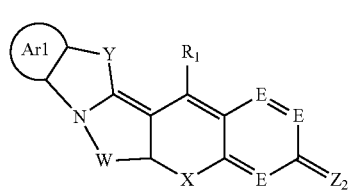

wherein $Ar_1$, E, X, Y, W, and $R_1$ are as defined in Formula I, $Z_2$ is $NR_6$, O, S or $O^+R_7$, and $R_6$ and $R_7$ are as defined in Formula I.

2. The dye compound according to claim 1, wherein one or more of $R_1$ to $R_8$, $R_{10}$ to $R_{22}$, $R_{35}$ to $R_{41}$, and the substituents thereof, are further substituted with a reactive substituent $R_x$ binding to a target substance to be labeled with the dye compound; the reactive substituents $R_x$ are selected from activated esters, carboxyl, amides, acrylamides, azides, acyl azides, acyl halides, alkynes, amines, aldehydes, ketones, alkyl halides, alkyl sulfonates, aryl halides, aziridines, boronates, diazoalkanes, epoxides, haloplatinates, halotriazines, imidoesters, isocyanates, silyl halides, sulfonate esters, sulfonyl halides, succinimidyl esters, sulpho-succinimidyl esters, anhydrides, acid halides, isothiocyanates, vinylsulphones, dichlorotriazines, haloacetamides, maleimides, carbodiimides, phosphoramidites, hydrazines, and hydrazides; and the activated esters are represented by —COR' where R' is succinimidyloxy (—$OC_4H_4O_2$), sulfosuccinimidyloxy (—$OC_4H_3O_2$—$SO_3H$), -1-oxybenzotriazolyl (—$OC_6H_4N_8$), aryloxy optionally containing one or more groups selected from nitro, halogen, cyano, and haloalkyl, or a carboxylic acid.

3. The dye compound according to claim 2, wherein the reactive substituents $R_x$ are covalently bonded to linkers L to form $R_X$-L-structures; the linkers are single bonds or straight or branched chains containing 1 to 20 linked atoms selected from the group consisting of carbon (C), nitrogen (N), oxygen (O), and sulfur (S) atoms, or are selected aliphatic hydrocarbon rings, aromatic hydrocarbon rings, heteroaliphatic rings and heteroaromatic rings; and the linkers are positively (+) or negatively (−) charged.

4. The dye compound according to claim 2, wherein the target substance is selected from biomolecules, nanoparticles, and organic compounds comprising one or more amino, sulfhydryl, carbonyl, hydroxyl, carboxyl, thiol, phosphoric acid, and thiophosphoric acid groups or is selected from the group consisting of: antibodies; antigens; lipids; proteins; peptides; carbohydrates; dextrans; fatty acids; phospholipids; lipopolysaccharides; nucleotides or oligonucleotides comprising or derivatized to comprise one or more amino, sulfhydryl, carbonyl, hydroxyl, carboxyl, thiol, phosphoric acid, and thiophosphoric acid groups; oxypolynucleotides or deoxypolynucleotides comprising or derivatized to comprise one or more amino, sulfhydryl, carbonyl, hydroxyl, carboxyl, thiol, phosphate, and thiophosphate groups; microbes; drugs; hormones; cells; cell membranes; toxins; and combinations thereof.

5. A dye compound selected from:

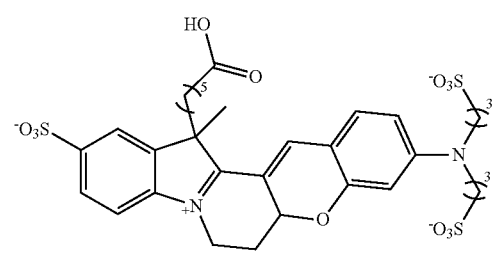

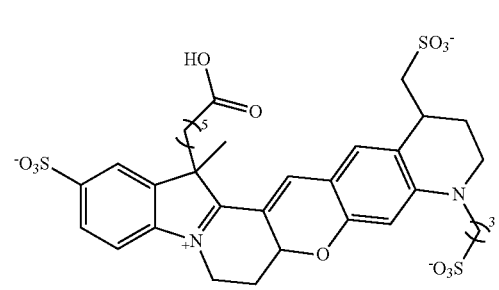

89
4
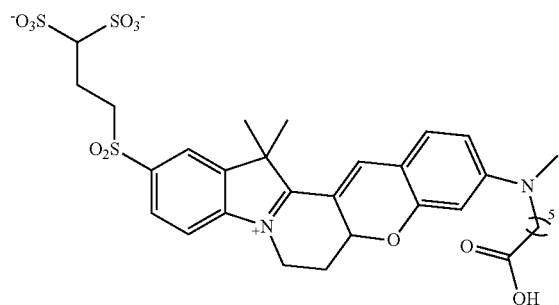
5
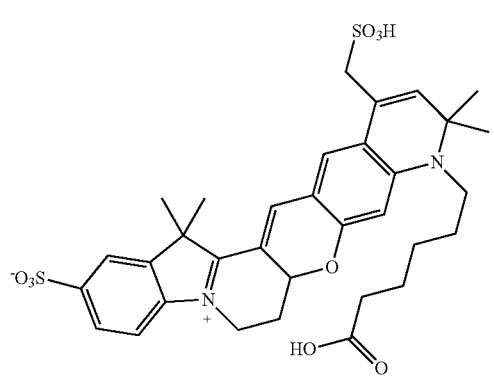
6
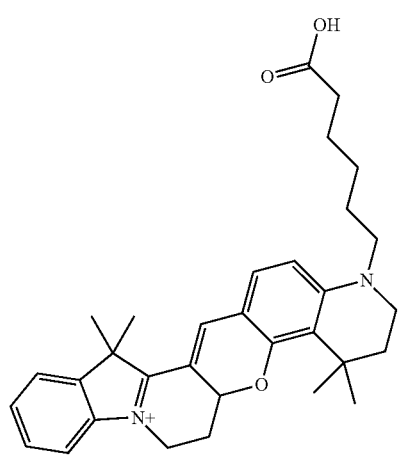
7
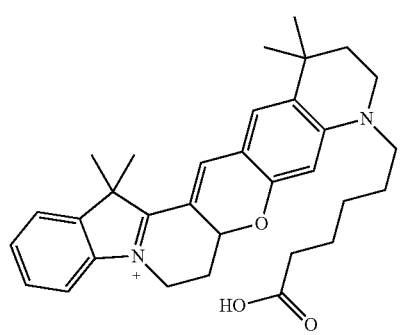
90
8
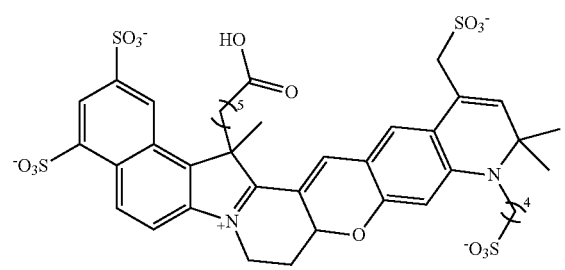
9
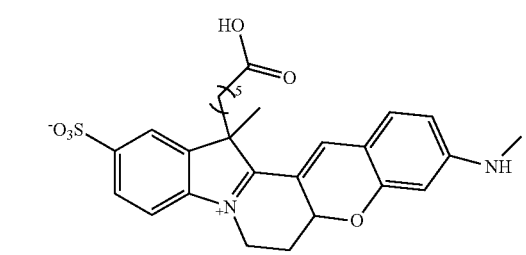
10
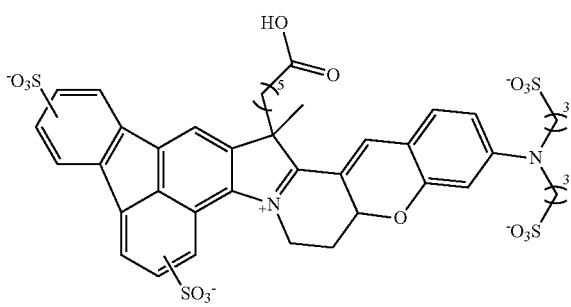
13
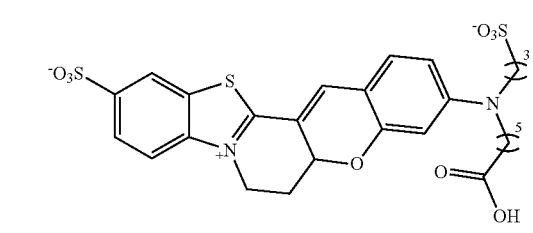
14
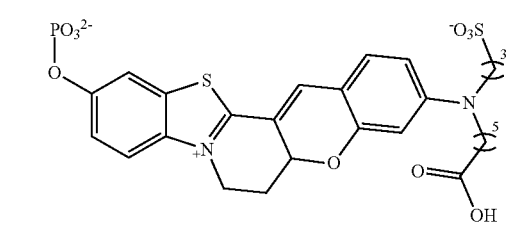
15
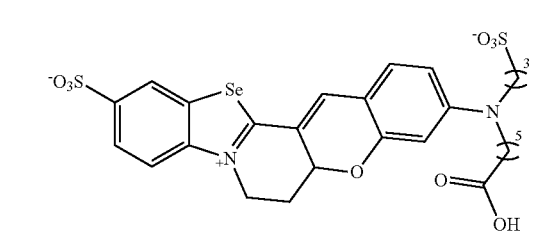

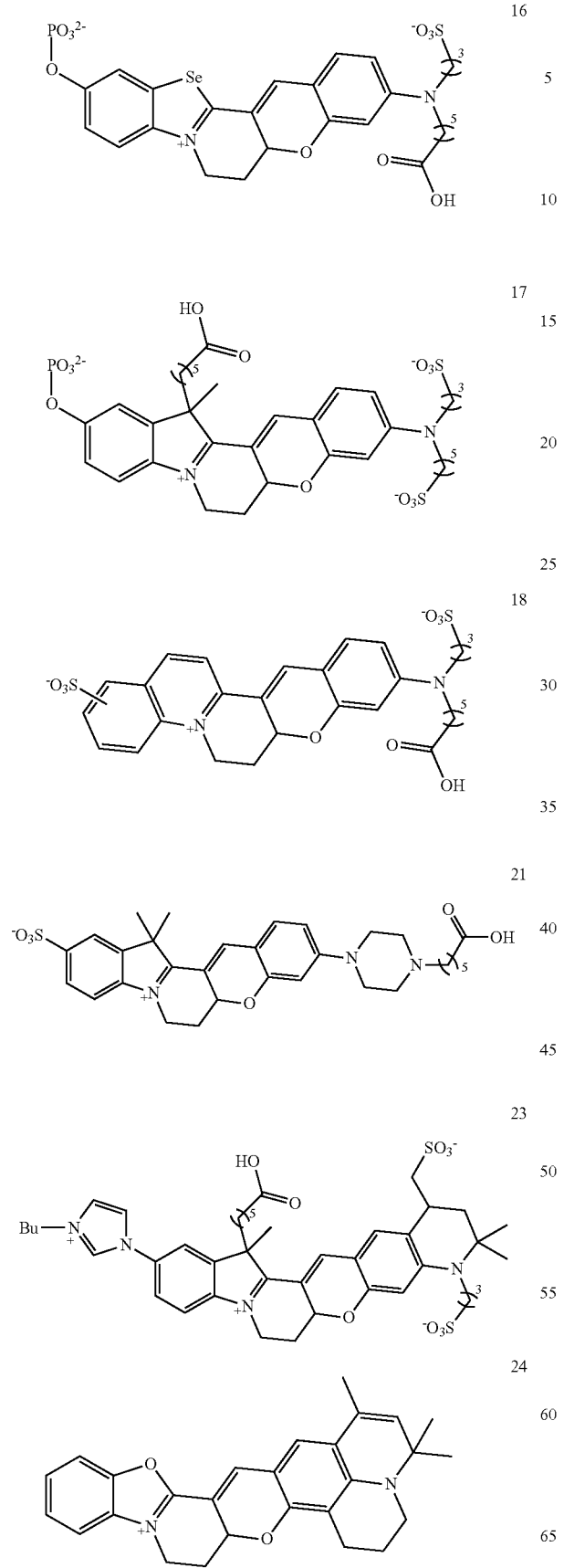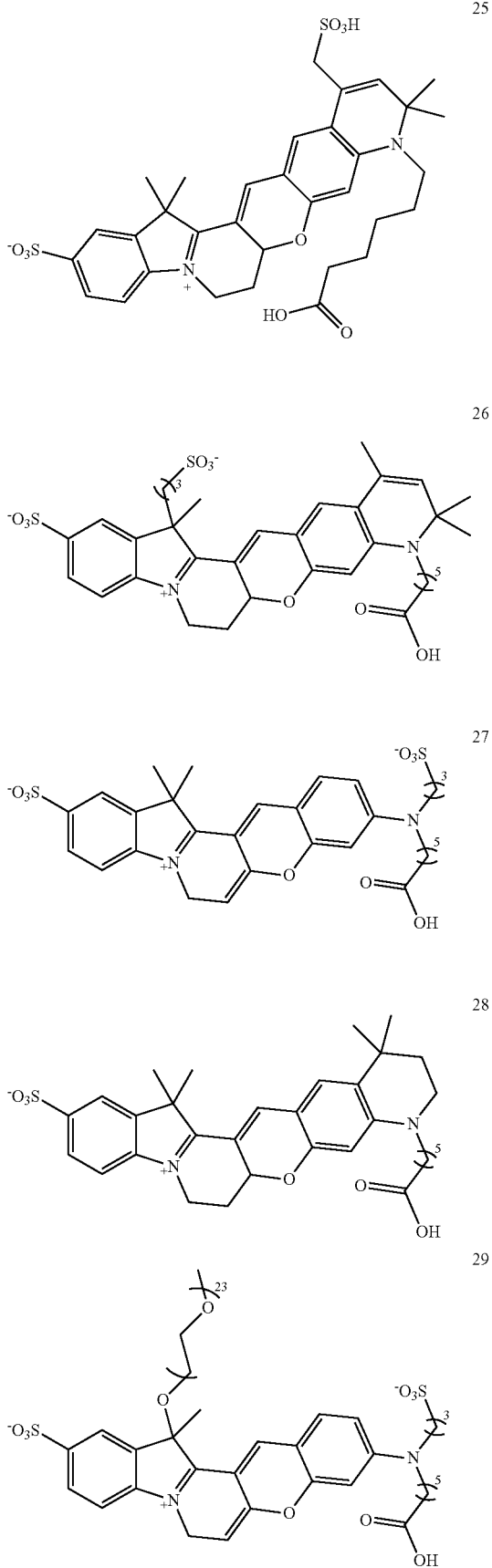

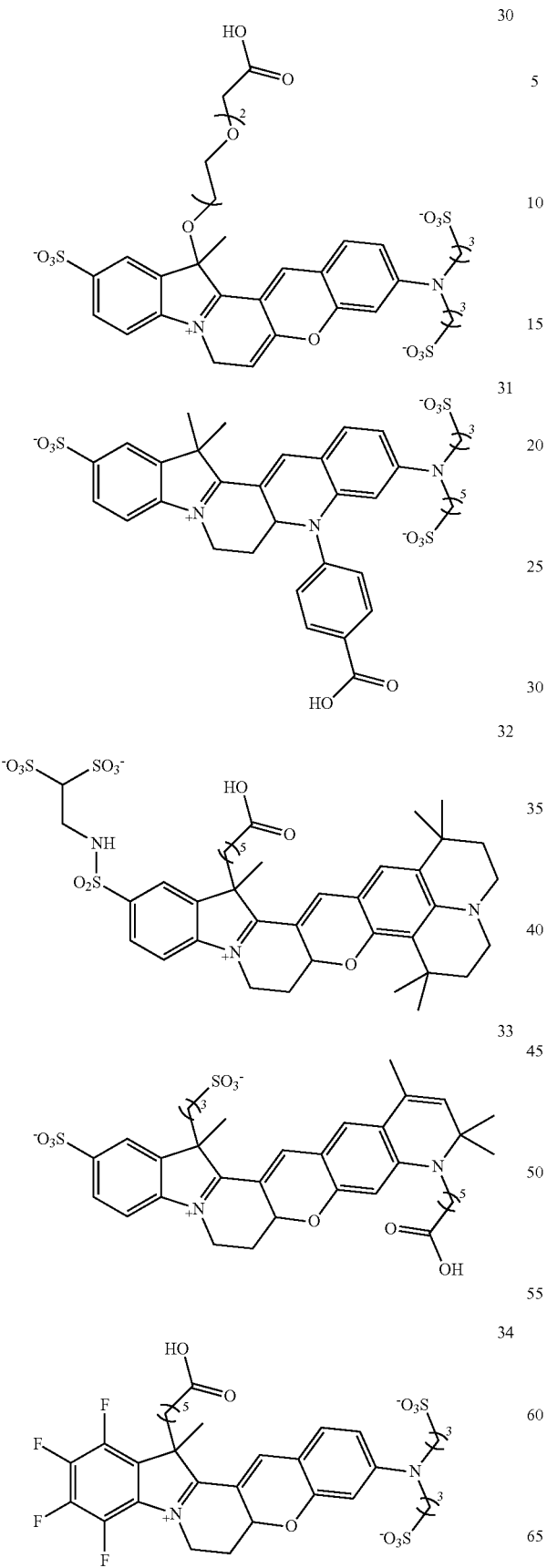
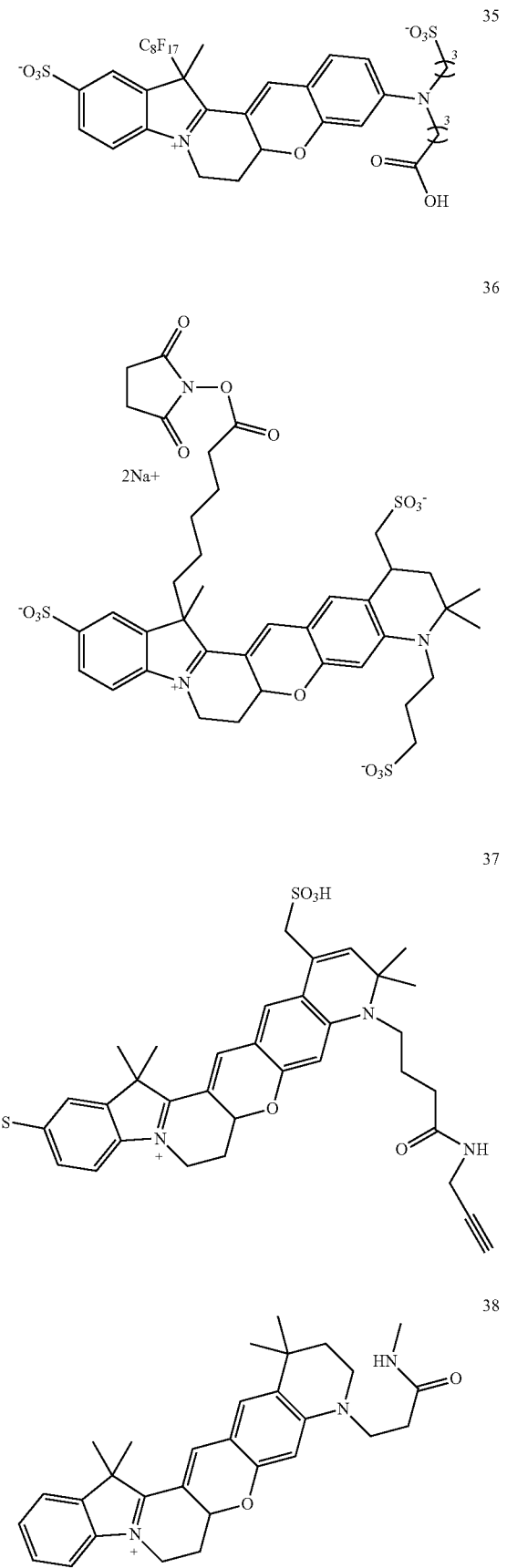

-continued
39
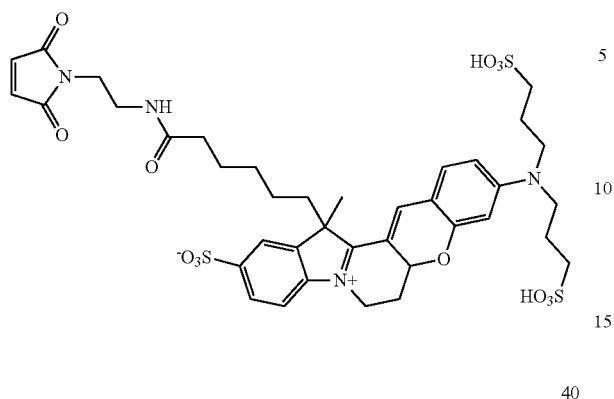
40
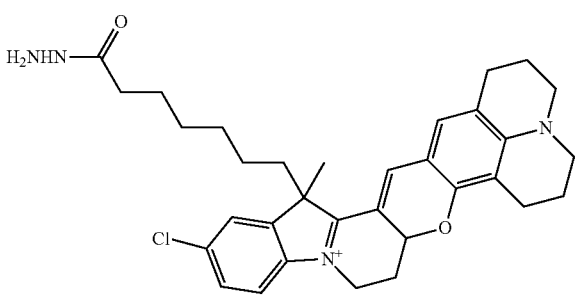
41
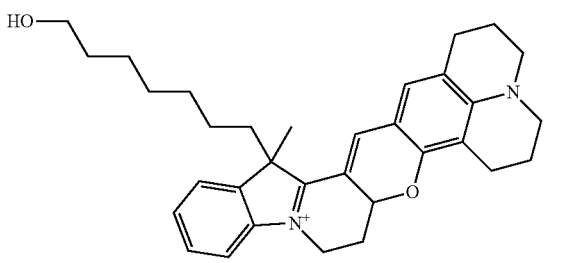
42
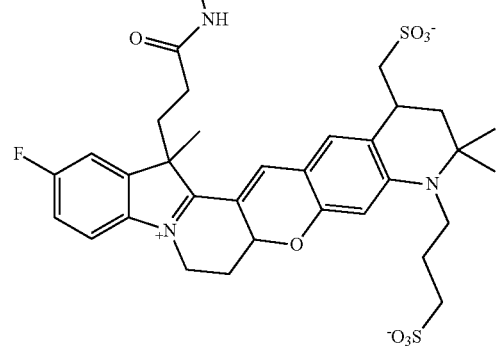
-continued
43
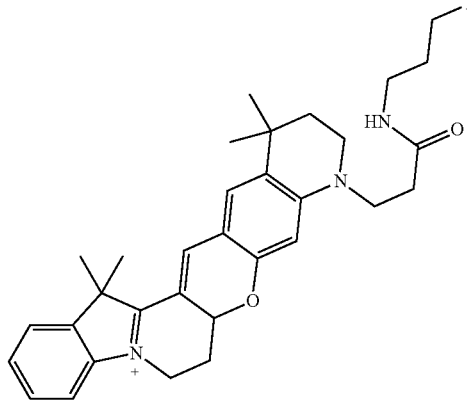
44
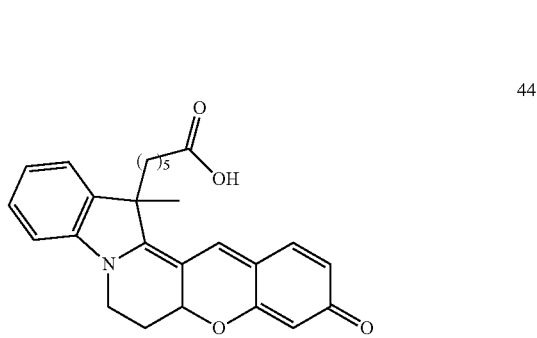
45
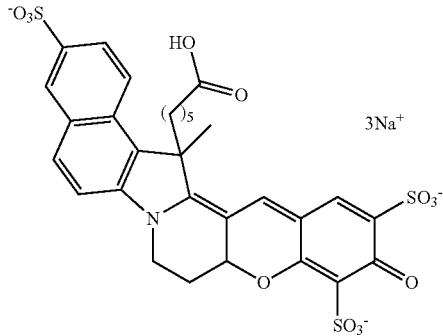
46
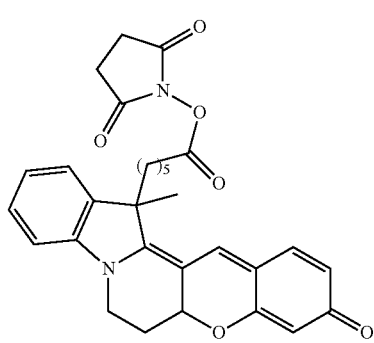

47
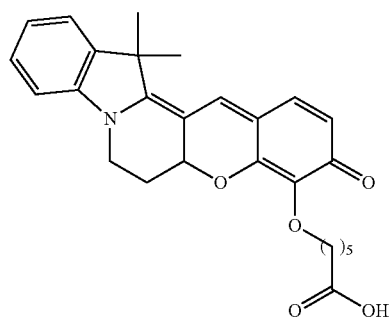
48
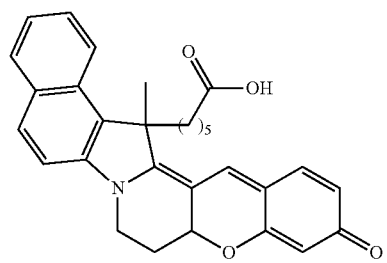
49
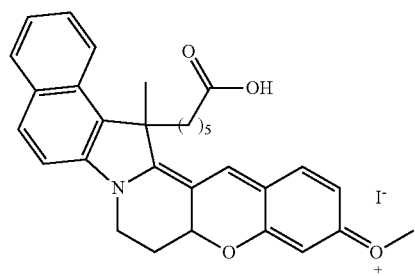
50
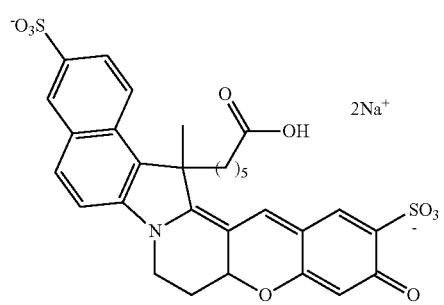
51
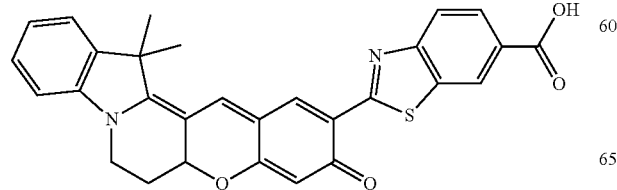
52
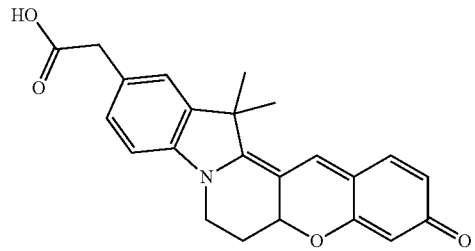
53
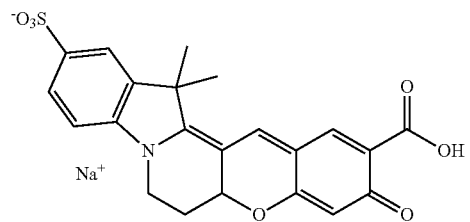
54
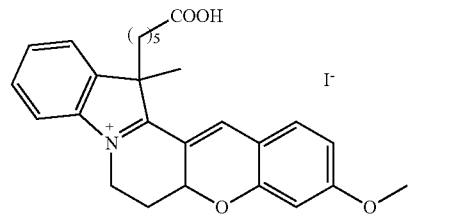
55
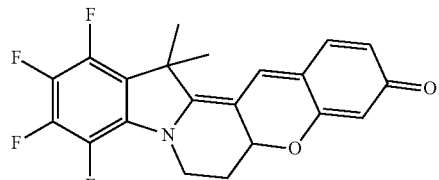
57
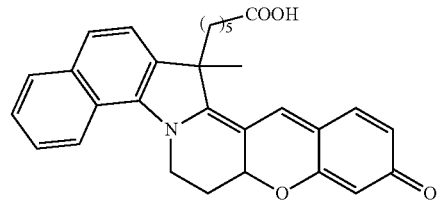
58
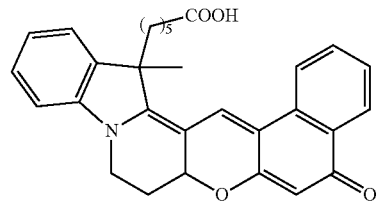
59
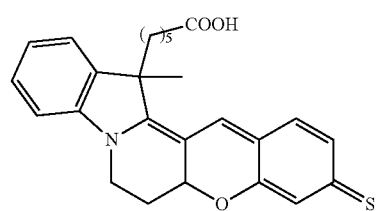

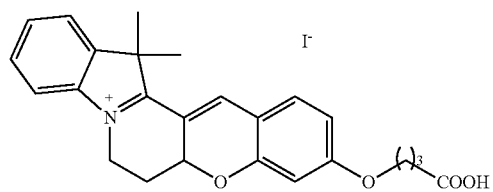
61
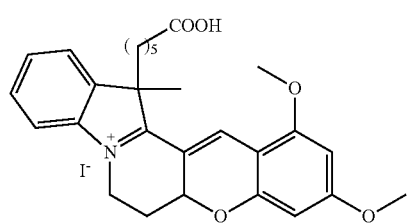
62
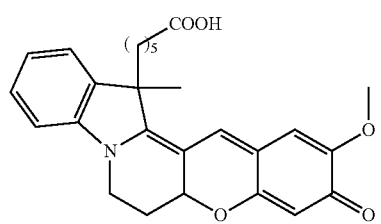
63
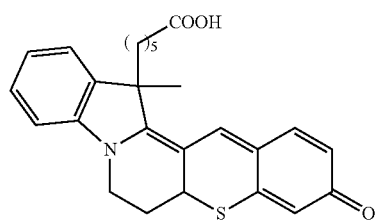
64
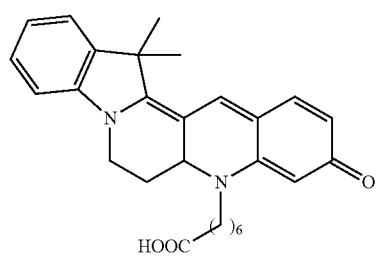
65
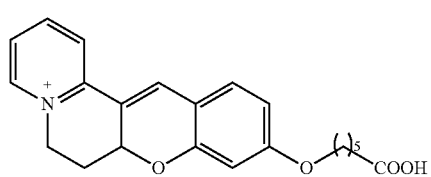
66
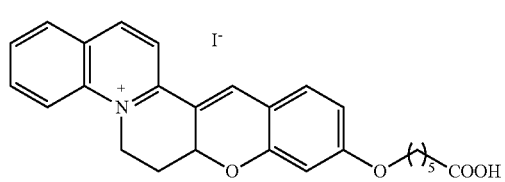
67
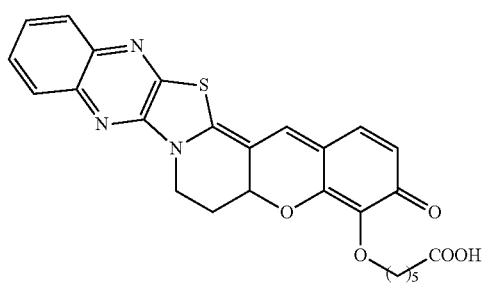
68
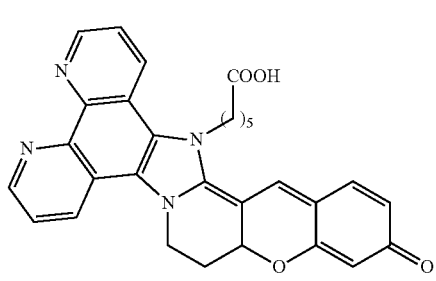
69
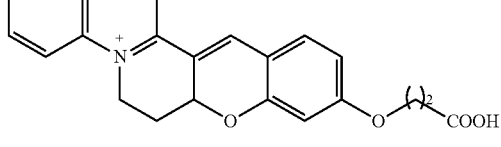
70
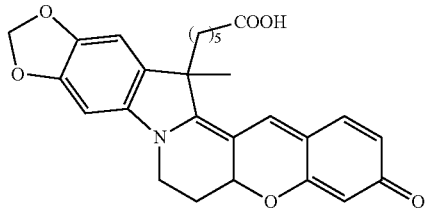
71
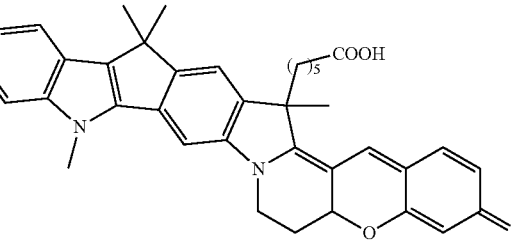
72
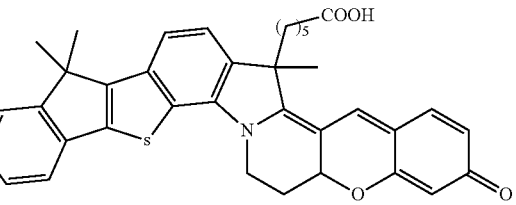
73

74 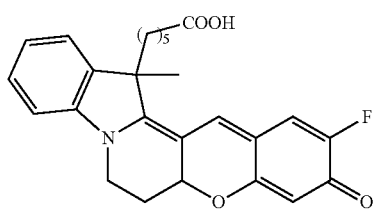
75 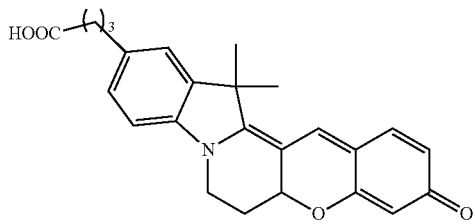
76 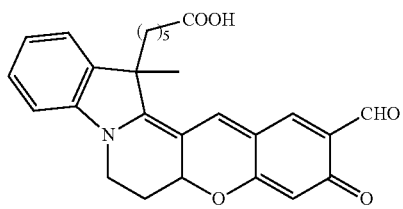
77 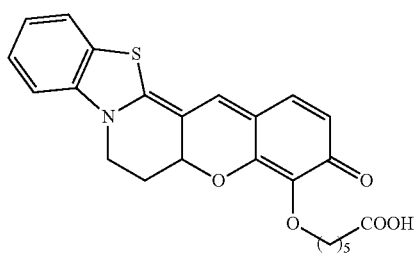
78 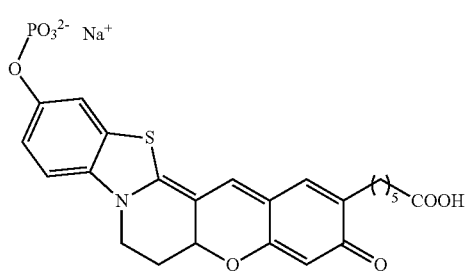
79 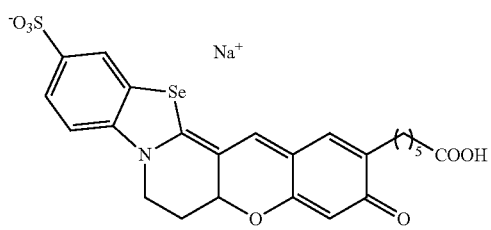
80 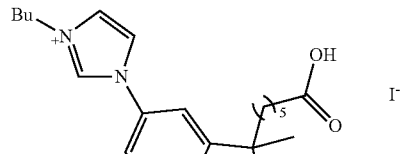
81 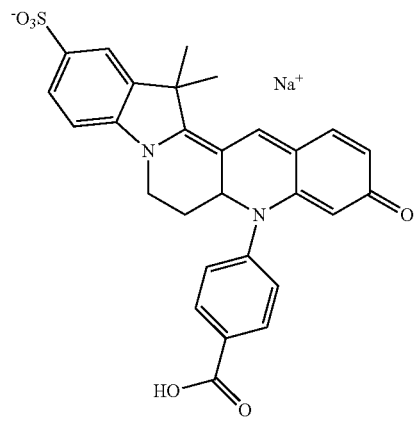
82 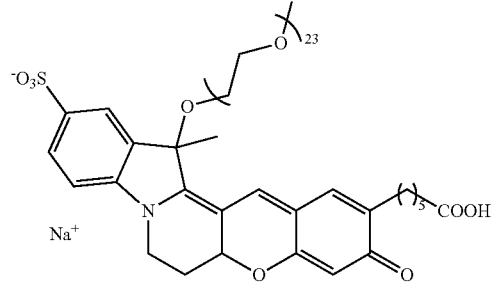
83 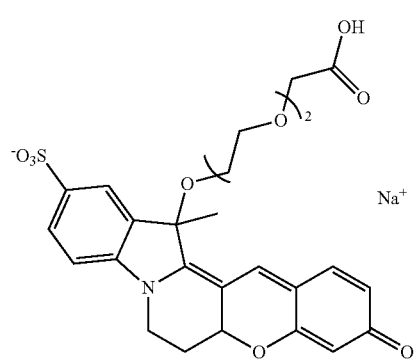
84 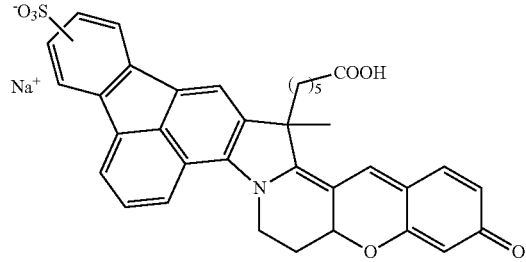

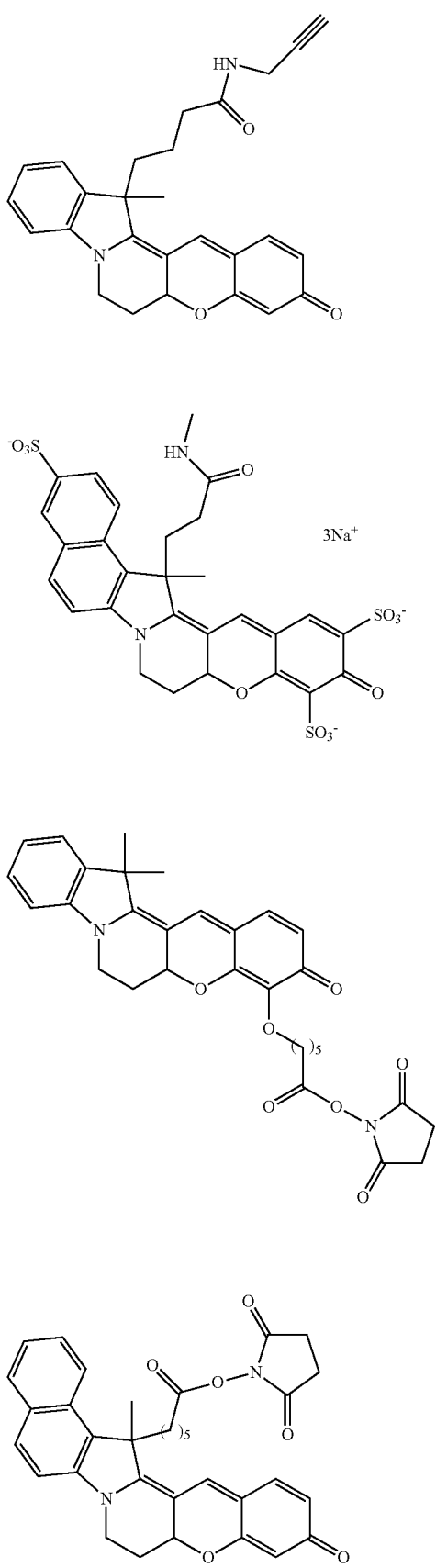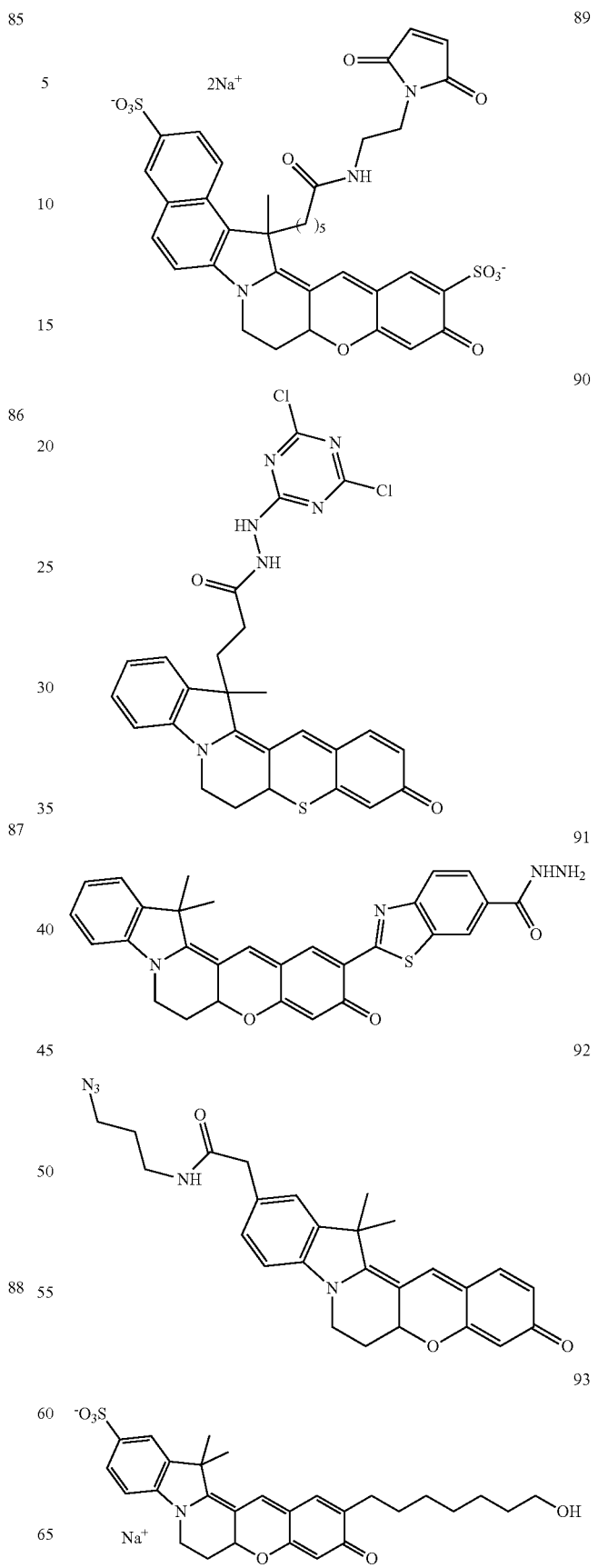

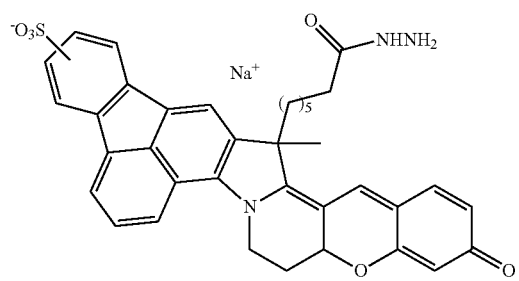
94
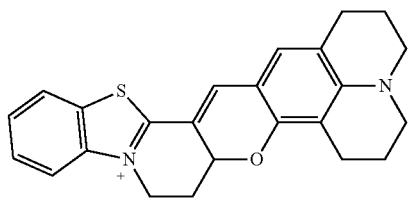
101
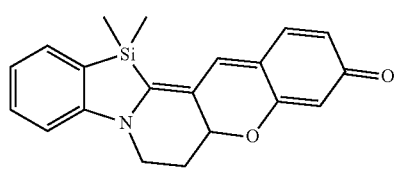
95
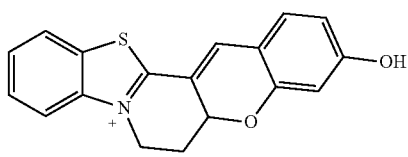
102
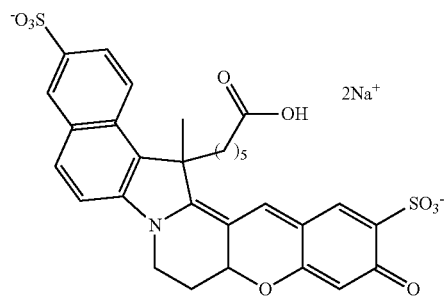
96
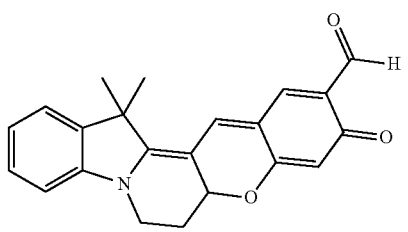
103
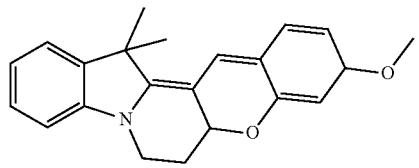
97
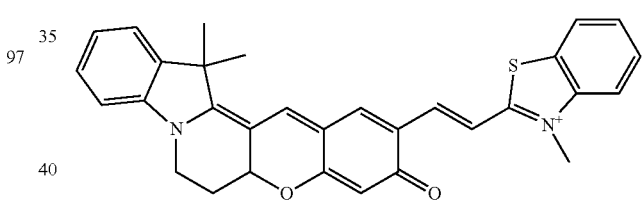
104
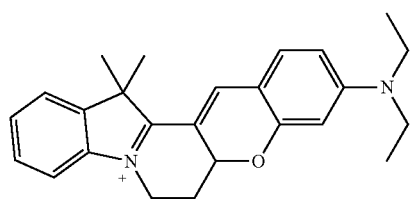
98
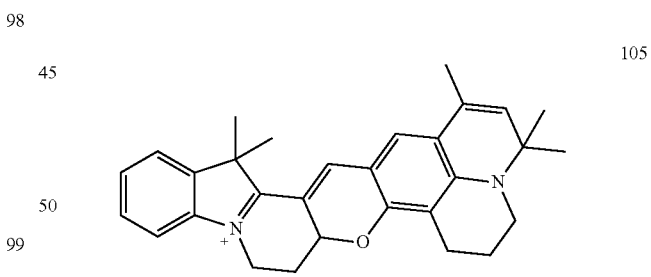
105
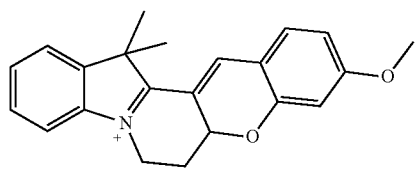
99
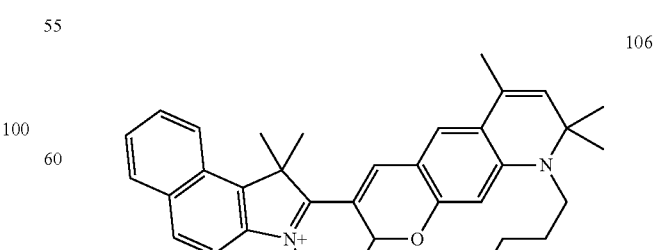
106
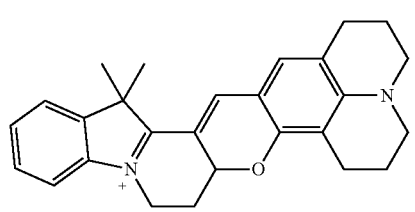
100

107

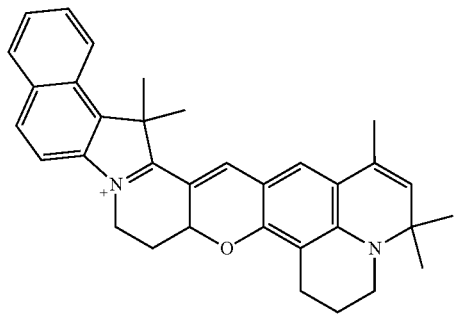

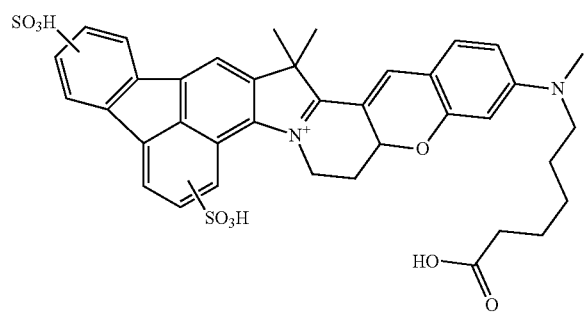

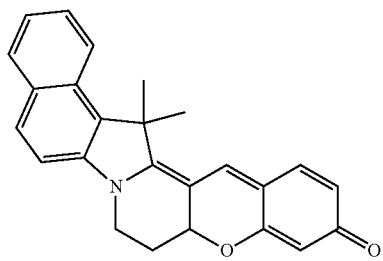

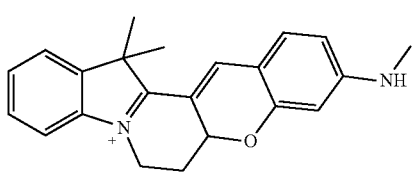

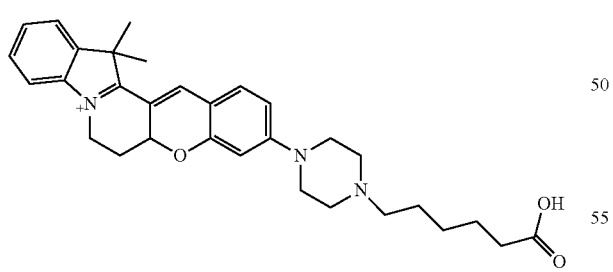

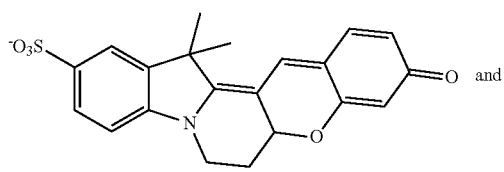

108

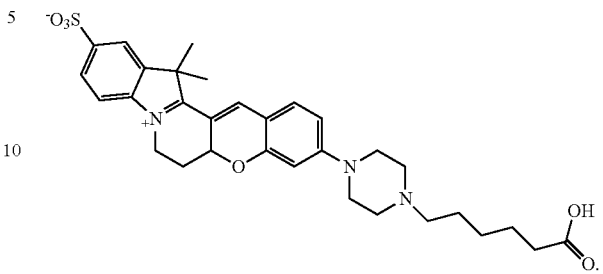

6. The dye compound according to claim 1, wherein the dye compound selectively stains intracellular mitochondria.

7. The dye compound according to claim 1, wherein a fluorescence intensity of the dye compound varies in response to intracellular pH change.

8. A method for labeling a target substance with the dye compound according to claim 1, comprising:
   introducing the dye compound into a sample comprising a target substance, followed by incubation.

9. The method according to claim 8, further comprising (b) measuring fluorescence of the dye compound bound to the target substance to quantify the target substance from the fluorescence intensity.

10. A compound selected from the group consisting of:

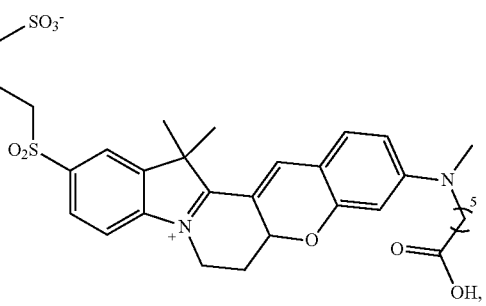

-continued
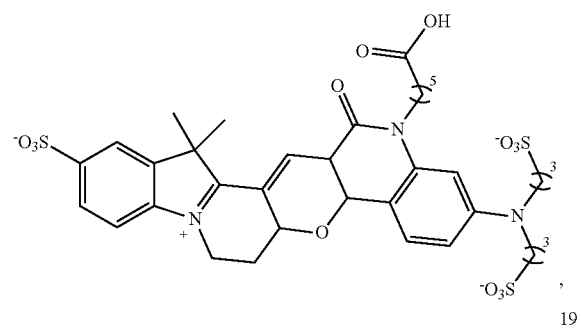
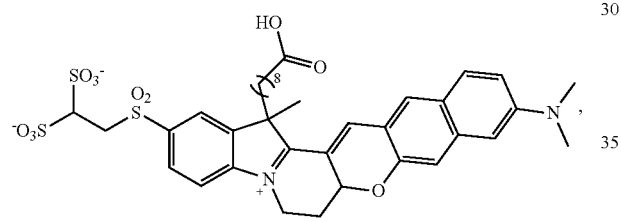
-continued
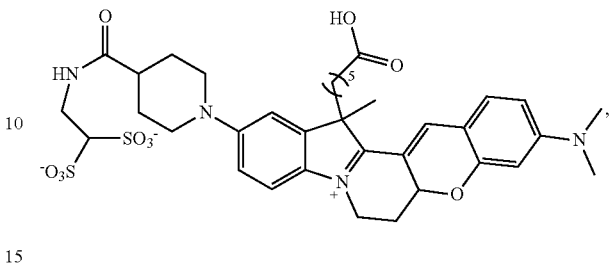
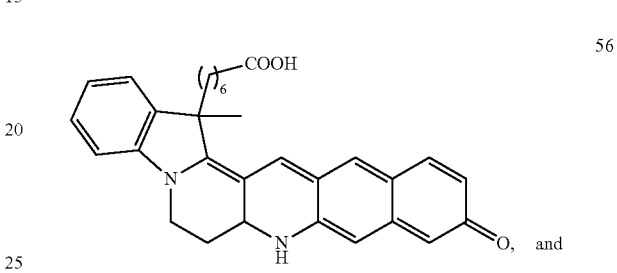
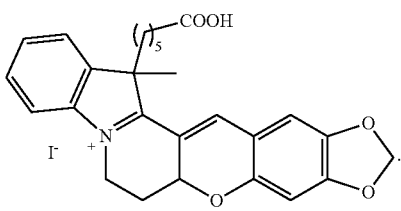
* * * * *